(12) United States Patent
Shalev et al.

(10) Patent No.: US 9,668,892 B2
(45) Date of Patent: Jun. 6, 2017

(54) MULTI-COMPONENT STENT-GRAFT SYSTEM FOR AORTIC DISSECTIONS

(71) Applicant: ENDOSPAN LTD., Herzilyia Pituach (IL)

(72) Inventors: Alon Shalev, Ra'anana (IL); Yaniv Marmur, Yokneam Moshava (IL)

(73) Assignee: ENDOSPAN LTD., Herzilyia Pituach (IL)

( * ) Notice: Subject to any disclaimer, the term of this patent is extended or adjusted under 35 U.S.C. 154(b) by 90 days.

(21) Appl. No.: 14/772,016

(22) PCT Filed: Feb. 18, 2014

(86) PCT No.: PCT/IL2014/050174
§ 371 (c)(1),
(2) Date: Sep. 1, 2015

(87) PCT Pub. No.: WO2014/141232
PCT Pub. Date: Sep. 18, 2014

(65) Prior Publication Data
US 2016/0030209 A1    Feb. 4, 2016

Related U.S. Application Data

(60) Provisional application No. 61/775,964, filed on Mar. 11, 2013.

(51) Int. Cl.
*A61F 2/07* (2013.01)
*A61F 2/856* (2013.01)
(Continued)

(52) U.S. Cl.
CPC ............... *A61F 2/856* (2013.01); *A61F 2/07* (2013.01); *A61F 2/89* (2013.01);
(Continued)

(58) Field of Classification Search
None
See application file for complete search history.

(56) References Cited

U.S. PATENT DOCUMENTS 4,180,613 A    12/1979    Vassiliou
4,355,426 A    10/1982    MacGregor
(Continued)

FOREIGN PATENT DOCUMENTS

CA    2 497 704        3/2004
CN    1194577 A        9/1998
(Continued)

OTHER PUBLICATIONS

"E-vita® open plus" product brochure (JOTEC GmbH, Hechingen, Germany), 2010.
(Continued)

*Primary Examiner* — Christian Sevilla
*Assistant Examiner* — Megan Wolf
(74) *Attorney, Agent, or Firm* — Sughrue Mion, PLLC

(57) ABSTRACT

A generally tubular stent-graft (24) has distal and proximal stent-graft ends (36, 38) and includes a generally tubular support element (30) and a covering element (32). When the stent-graft (24) is unconstrained in a radially-expanded state: (1) the covering and support elements (32, 30) are shaped so as to together define a lateral fenestration (34) having distal and proximal fenestration ends (35, 37), (2) a perimeter (P1) of the distal stent-graft end (36) equals at least 200% of a perimeter (P2) of the proximal stent-graft end (38), and (3) the stent-graft (24) includes a dissection-reinforcement axial portion (48), which (a) has a proximal dissection-reinforcement end (52) that is disposed no more than 20 mm proximal to the proximal fenestration end (37), (b) extends along the stent-graft for a distance equal to between 5% and 32% of a greatest perimeter of the stent-graft (24) distally to the
(Continued)

distal fenestration end (35), and (c) has a radial strength that is at least 10% greater than an average radial strength of the entire stent-graft (24). Other embodiments are also described.

29 Claims, 12 Drawing Sheets

(51) Int. Cl.
*A61F 2/89* (2013.01)
*A61F 2/06* (2013.01)

(52) U.S. Cl.
CPC ... *A61F 2002/061* (2013.01); *A61F 2002/075* (2013.01); *A61F 2230/0013* (2013.01); *A61F 2230/0069* (2013.01); *A61F 2250/006* (2013.01); *A61F 2250/0039* (2013.01)

(56) References Cited

U.S. PATENT DOCUMENTS

| | | | |
|---|---|---|---|
| 4,505,767 A | 3/1985 | Quin |
| 4,562,596 A | 1/1986 | Kornberg |
| 4,577,631 A | 3/1986 | Kreamer |
| 4,617,932 A | 10/1986 | Kornberg |
| 4,665,906 A | 5/1987 | Jervis |
| 4,739,762 A | 4/1988 | Palmaz |
| 4,787,899 A | 11/1988 | Lazarus |
| 4,816,339 A | 3/1989 | Tu et al. |
| 4,878,906 A | 11/1989 | Lindemann et al. |
| 4,886,062 A | 12/1989 | Wiktor |
| 4,938,740 A | 7/1990 | Melbin |
| 4,969,458 A | 11/1990 | Wiktor |
| 5,042,707 A | 8/1991 | Taheri |
| 5,064,435 A | 11/1991 | Porter |
| 5,104,404 A | 4/1992 | Wolff |
| 5,122,136 A | 6/1992 | Guglielmi et al. |
| 5,133,732 A | 7/1992 | Wiktor |
| 5,192,286 A | 3/1993 | Phan et al. |
| 5,234,448 A | 8/1993 | Wholey et al. |
| 5,425,739 A | 6/1995 | Jessen |
| 5,425,765 A | 6/1995 | Tiefenbrun et al. |
| 5,439,446 A | 8/1995 | Barry |
| 5,486,183 A | 1/1996 | Middleman et al. |
| 5,507,769 A | 4/1996 | Marin et al. |
| 5,509,923 A | 4/1996 | Middleman et al. |
| 5,522,880 A | 6/1996 | Barone et al. |
| 5,527,322 A | 6/1996 | Klein et al. |
| 5,549,662 A | 8/1996 | Fordenbacher |
| 5,554,181 A | 9/1996 | Das |
| 5,556,413 A | 9/1996 | Lam |
| 5,562,724 A | 10/1996 | Vorwerk et al. |
| 5,575,818 A | 11/1996 | Pinchuk |
| 5,607,445 A | 3/1997 | Summers |
| 5,613,974 A | 3/1997 | Andreas et al. |
| 5,632,746 A | 5/1997 | Middleman et al. |
| 5,632,763 A | 5/1997 | Glastra |
| 5,632,772 A | 5/1997 | Alcime et al. |
| 5,639,278 A | 6/1997 | Dereume et al. |
| 5,643,340 A | 7/1997 | Nunokawa |
| 5,653,743 A | 8/1997 | Martin |
| 5,676,696 A | 10/1997 | Marcade |
| 5,676,697 A | 10/1997 | McDonald |
| 5,728,134 A | 3/1998 | Barak |
| 5,749,825 A | 5/1998 | Fischell et al. |
| 5,749,879 A | 5/1998 | Middleman et al. |
| 5,755,770 A | 5/1998 | Ravenscroft |
| 5,755,771 A | 5/1998 | Penn et al. |
| 5,755,774 A | 5/1998 | Pinchuk |
| 5,755,777 A | 5/1998 | Chuter |
| 5,755,781 A | 5/1998 | Jayaraman |
| 5,769,882 A | 6/1998 | Fogarty et al. |
| 5,769,884 A | 6/1998 | Solovay |
| 5,782,903 A | 7/1998 | Wiktor |
| 5,782,906 A | 7/1998 | Marshall et al. |
| 5,824,040 A | 10/1998 | Cox et al. |
| 5,827,321 A | 10/1998 | Roubin |
| 5,843,120 A | 12/1998 | Israel et al. |
| 5,843,170 A | 12/1998 | Ahn |
| 5,855,600 A | 1/1999 | Alt |
| 5,860,991 A | 1/1999 | Klein et al. |
| 5,876,432 A | 3/1999 | Lau et al. |
| 5,906,641 A | 5/1999 | Thompson et al. |
| 5,921,994 A | 7/1999 | Andreas et al. |
| 5,944,750 A | 8/1999 | Tanner et al. |
| 5,976,178 A | 11/1999 | Goldsteen et al. |
| 5,980,552 A | 11/1999 | Pinchasik |
| 6,015,431 A | 1/2000 | Thornton et al. |
| 6,016,810 A | 1/2000 | Ravenscroft |
| 6,030,414 A | 2/2000 | Taheri |
| 6,033,435 A | 3/2000 | Penn et al. |
| 6,036,725 A | 3/2000 | Avellanet |
| 6,059,824 A | 5/2000 | Taheri |
| 6,077,298 A | 6/2000 | Tu et al. |
| 6,099,497 A | 8/2000 | Adams et al. |
| 6,117,145 A | 9/2000 | Wood et al. |
| 6,152,956 A | 11/2000 | Pierce |
| 6,156,064 A | 12/2000 | Chouinard |
| 6,168,615 B1 | 1/2001 | Ken et al. |
| 6,200,339 B1 | 3/2001 | Leschinsky et al. |
| 6,206,893 B1 | 3/2001 | Klein et al. |
| 6,270,524 B1 | 8/2001 | Kim |
| 6,283,991 B1 | 9/2001 | Cox et al. |
| 6,290,720 B1 | 9/2001 | Khosravi et al. |
| 6,312,458 B1 | 11/2001 | Golds |
| 6,319,287 B1 | 11/2001 | Frimberger |
| 6,325,823 B1 | 12/2001 | Horzewski et al. |
| 6,344,056 B1 | 2/2002 | Dehdashtian |
| 6,395,018 B1 | 5/2002 | Castaneda |
| 6,406,420 B1 | 6/2002 | McCarthy |
| 6,428,565 B1 | 8/2002 | Wisselink |
| 6,451,048 B1 | 9/2002 | Berg et al. |
| 6,506,211 B1 | 1/2003 | Skubitz et al. |
| 6,565,597 B1 | 5/2003 | Fearnot et al. |
| 6,613,075 B1 | 9/2003 | Healy et al. |
| 6,613,078 B1 | 9/2003 | Barone |
| 6,613,079 B1 | 9/2003 | Wolinsky et al. |
| 6,635,083 B1 | 10/2003 | Cheng et al. |
| 6,645,242 B1 | 11/2003 | Quinn |
| 6,648,901 B2 | 11/2003 | Fleischman et al. |
| 6,648,911 B1 | 11/2003 | Sirhan |
| 6,652,567 B1 | 11/2003 | Deaton |
| 6,656,214 B1 | 12/2003 | Fogarty et al. |
| 6,673,080 B2 | 1/2004 | Reynolds et al. |
| 6,692,520 B1 | 2/2004 | Gambale et al. |
| 6,695,833 B1 | 2/2004 | Frantzen |
| 6,730,117 B1 | 5/2004 | Tseng et al. |
| 6,743,195 B2 | 6/2004 | Zucker |
| 6,748,953 B2 | 6/2004 | Sherry et al. |
| 6,752,826 B2 | 6/2004 | Holloway et al. |
| 6,776,794 B1 | 8/2004 | Hong et al. |
| 6,814,749 B2 | 11/2004 | Cox et al. |
| 6,814,752 B1 | 11/2004 | Chuter |
| 6,824,560 B2 | 11/2004 | Pelton |
| 6,846,321 B2 | 1/2005 | Zucker |
| 6,907,285 B2 | 6/2005 | Denker et al. |
| 6,908,477 B2 | 6/2005 | McGuckin, Jr. et al. |
| 6,929,660 B1 | 8/2005 | Ainsworth et al. |
| 6,942,691 B1 | 9/2005 | Chuter |
| 6,953,469 B2 | 10/2005 | Ryan |
| 6,964,679 B1 | 11/2005 | Marcade et al. |
| 6,986,774 B2 | 1/2006 | Middleman et al. |
| 7,008,441 B2 | 3/2006 | Zucker |
| 7,022,131 B1 | 4/2006 | DeRowe et al. |
| 7,044,962 B2 | 5/2006 | Elliott |
| 7,083,822 B2 | 8/2006 | Brightbill |
| 7,105,020 B2 | 9/2006 | Greenberg et al. |
| 7,112,217 B1 | 9/2006 | Kugler et al. |
| 7,115,127 B2 | 10/2006 | Lindenbaum et al. |
| 7,122,052 B2 | 10/2006 | Greenhalgh |
| 7,144,421 B2 | 12/2006 | Carpenter et al. |
| 7,175,651 B2 | 2/2007 | Kerr |
| 7,198,638 B2 | 4/2007 | Dong |

(56) References Cited

U.S. PATENT DOCUMENTS

| | | |
|---|---|---|
| 7,201,772 B2 | 4/2007 | Schwammenthal et al. |
| 7,223,266 B2 | 5/2007 | Lindenbaum et al. |
| 7,261,733 B1 | 8/2007 | Brown et al. |
| 7,279,003 B2 | 10/2007 | Berra et al. |
| 7,294,145 B2 | 11/2007 | Ward |
| 7,306,623 B2 | 12/2007 | Watson |
| 7,341,598 B2 | 3/2008 | Davidson et al. |
| 7,399,313 B2 | 7/2008 | Brown et al. |
| 7,407,509 B2 | 8/2008 | Greenberg et al. |
| 7,413,573 B2 | 8/2008 | Hartley et al. |
| 7,429,269 B2 | 9/2008 | Schwammenthal et al. |
| 7,442,204 B2 | 10/2008 | Schwammenthal et al. |
| 7,473,272 B2 | 1/2009 | Pryor |
| 7,537,609 B2 | 5/2009 | Davidson et al. |
| 7,540,881 B2 | 6/2009 | Meyer et al. |
| 7,544,160 B2 | 6/2009 | Gross |
| 7,616,997 B2 | 11/2009 | Kieval et al. |
| 7,632,303 B1 | 12/2009 | Stalker et al. |
| 7,637,939 B2 | 12/2009 | Tischler |
| 7,645,298 B2 | 1/2010 | Hartley et al. |
| 7,655,037 B2 | 2/2010 | Fleming, III et al. |
| 7,662,161 B2 | 2/2010 | Briganti et al. |
| 7,662,168 B2 | 2/2010 | McGuckin, Jr. et al. |
| 7,670,369 B2 | 3/2010 | Schaeffer |
| 7,678,141 B2 | 3/2010 | Greenan et al. |
| 7,708,704 B2 | 5/2010 | Mitelberg |
| 7,722,626 B2 | 5/2010 | Middleman et al. |
| 7,731,732 B2 | 6/2010 | Ken |
| 7,803,178 B2 | 9/2010 | Whirley |
| 7,806,923 B2 | 10/2010 | Moloney |
| 7,815,673 B2 | 10/2010 | Bloom et al. |
| 7,833,259 B2 | 11/2010 | Boatman |
| 7,887,575 B2 | 2/2011 | Kujawski |
| 7,914,572 B2 | 3/2011 | Hartley et al. |
| 7,955,374 B2 | 6/2011 | Erickson et al. |
| 7,959,662 B2 | 6/2011 | Erbel et al. |
| 8,016,853 B2 | 9/2011 | Griffen et al. |
| 8,021,419 B2 | 9/2011 | Hartley et al. |
| 8,043,365 B2 | 10/2011 | Thramann |
| 8,048,140 B2 | 11/2011 | Purdy |
| 8,052,741 B2 | 11/2011 | Bruszewski et al. |
| 8,066,755 B2 | 11/2011 | Zacharias |
| 8,080,026 B2 | 12/2011 | Konstantino et al. |
| 8,080,053 B2 | 12/2011 | Satasiya |
| 8,100,960 B2 | 1/2012 | Bruszewski |
| 8,157,810 B2 | 4/2012 | Case et al. |
| 8,157,852 B2 | 4/2012 | Bloom et al. |
| 8,167,926 B2 | 5/2012 | Hartley et al. |
| 8,172,892 B2 | 5/2012 | Chuter |
| 8,197,475 B2 | 6/2012 | Bruszewski et al. |
| 8,211,158 B2 | 7/2012 | Wolf |
| 8,216,298 B2 | 7/2012 | Wright et al. |
| 8,221,494 B2 | 7/2012 | Schreck et al. |
| 8,226,706 B2 | 7/2012 | Hartley et al. |
| 8,251,963 B2 | 8/2012 | Chin et al. |
| 8,262,719 B2 | 9/2012 | Erickson et al. |
| 8,273,115 B2 | 9/2012 | Hamer et al. |
| 8,292,951 B2 | 10/2012 | Muzslay |
| 8,333,800 B2 | 12/2012 | Bruszewski et al. |
| 8,353,898 B2 | 1/2013 | Lutze et al. |
| 8,394,136 B2 | 3/2013 | Hartley et al. |
| 8,506,622 B2 | 8/2013 | Bruszewski et al. |
| 8,728,148 B2 | 5/2014 | Roeder et al. |
| 8,808,355 B2 | 8/2014 | Barrand |
| 8,945,203 B2 | 2/2015 | Shalev et al. |
| 8,968,384 B2 | 3/2015 | Pearson et al. |
| 9,101,457 B2 | 8/2015 | Benary |
| 9,168,123 B2 | 10/2015 | Barrand |
| 9,254,209 B2 | 2/2016 | Shalev |
| 2001/0000188 A1 | 4/2001 | Lenker et al. |
| 2001/0004705 A1 | 6/2001 | Killion |
| 2001/0010006 A1 | 7/2001 | Bachinski et al. |
| 2001/0014823 A1 | 8/2001 | Ressemann et al. |
| 2001/0034550 A1 | 10/2001 | Buirge |
| 2001/0044647 A1 | 11/2001 | Pinchuk et al. |
| 2001/0044651 A1 | 11/2001 | Steinke |
| 2001/0044652 A1 | 11/2001 | Moore |
| 2001/0047198 A1 | 11/2001 | Drasler |
| 2001/0049550 A1 | 12/2001 | Martin et al. |
| 2001/0053930 A1 | 12/2001 | Kugler et al. |
| 2002/0040236 A1 | 4/2002 | Lau |
| 2002/0052644 A1 | 5/2002 | Shaolian et al. |
| 2002/0099441 A1 | 7/2002 | Dehdashtian |
| 2002/0107564 A1 | 8/2002 | Cox |
| 2002/0123791 A1 | 9/2002 | Harrison |
| 2002/0156495 A1 | 10/2002 | Brenneman et al. |
| 2002/0156517 A1 | 10/2002 | Prouse et al. |
| 2003/0040791 A1 | 2/2003 | Oktay |
| 2003/0040804 A1 | 2/2003 | Stack et al. |
| 2003/0057156 A1 | 3/2003 | Peterson et al. |
| 2003/0065345 A1 | 4/2003 | Weadock |
| 2003/0074055 A1 | 4/2003 | Haverkost |
| 2003/0093145 A1 | 5/2003 | Lawrence-Brown et al. |
| 2003/0114061 A1 | 6/2003 | Matsuda et al. |
| 2003/0130720 A1 | 7/2003 | DePalma et al. |
| 2003/0139802 A1 | 7/2003 | Wulfman et al. |
| 2003/0139805 A1 | 7/2003 | Holmberg et al. |
| 2003/0153944 A1 | 8/2003 | Phung et al. |
| 2003/0153968 A1 | 8/2003 | Geis et al. |
| 2003/0163187 A1 | 8/2003 | Weber |
| 2003/0191523 A1 | 10/2003 | Hojeibane |
| 2003/0199967 A1 | 10/2003 | Hartley et al. |
| 2003/0204236 A1 | 10/2003 | Letort |
| 2003/0204242 A1 | 10/2003 | Zarins et al. |
| 2003/0208192 A1 | 11/2003 | Truckai et al. |
| 2003/0212449 A1 | 11/2003 | Cox |
| 2003/0236567 A1 | 12/2003 | Elliot |
| 2004/0015227 A1 | 1/2004 | Vardi et al. |
| 2004/0015229 A1 | 1/2004 | Fulkerson |
| 2004/0098091 A1 | 5/2004 | Erbel |
| 2004/0106972 A1 | 6/2004 | Deaton |
| 2004/0106978 A1 | 6/2004 | Greenberg et al. |
| 2004/0117003 A1 | 6/2004 | Ouriel et al. |
| 2004/0133266 A1 | 7/2004 | Clerc et al. |
| 2004/0171978 A1 | 9/2004 | Shalaby |
| 2004/0176832 A1 | 9/2004 | Hartley et al. |
| 2004/0181149 A1 | 9/2004 | Langlotz et al. |
| 2004/0215319 A1 | 10/2004 | Berra et al. |
| 2004/0215320 A1 | 10/2004 | Machek |
| 2004/0215327 A1 | 10/2004 | Doig et al. |
| 2005/0033406 A1 | 2/2005 | Barnhart et al. |
| 2005/0049678 A1 | 3/2005 | Cocks et al. |
| 2005/0065545 A1 | 3/2005 | Wallace |
| 2005/0070995 A1 | 3/2005 | Zilla et al. |
| 2005/0085900 A1 | 4/2005 | Case |
| 2005/0102018 A1 | 5/2005 | Carpenter et al. |
| 2005/0102021 A1 | 5/2005 | Osborne |
| 2005/0131512 A1 | 6/2005 | Vonderwalde |
| 2005/0131517 A1 | 6/2005 | Hartley et al. |
| 2005/0143802 A1 | 6/2005 | Soykan et al. |
| 2005/0149166 A1 | 7/2005 | Schaeffer et al. |
| 2005/0154448 A1 | 7/2005 | Cully |
| 2005/0171598 A1 | 8/2005 | Schaeffer et al. |
| 2005/0177132 A1 | 8/2005 | Lentz et al. |
| 2005/0177222 A1 | 8/2005 | Mead |
| 2005/0177228 A1 | 8/2005 | Solem et al. |
| 2005/0203606 A1 | 9/2005 | VanCamp |
| 2005/0216018 A1 | 9/2005 | Sennett et al. |
| 2005/0222649 A1 | 10/2005 | Capuano |
| 2005/0222667 A1 | 10/2005 | Hunt |
| 2005/0222668 A1 | 10/2005 | Schaeffer et al. |
| 2005/0222669 A1 | 10/2005 | Purdy |
| 2005/0234542 A1 | 10/2005 | Melsheimer |
| 2005/0266042 A1 | 12/2005 | Tseng |
| 2006/0015170 A1 | 1/2006 | Jones et al. |
| 2006/0030911 A1 | 2/2006 | Letort |
| 2006/0052799 A1 | 3/2006 | Middleman et al. |
| 2006/0069426 A1 | 3/2006 | Weinberger |
| 2006/0095104 A1 | 5/2006 | Magers et al. |
| 2006/0095114 A1 | 5/2006 | Hartley et al. |
| 2006/0100684 A1 | 5/2006 | Elliott |
| 2006/0106406 A1 | 5/2006 | Weinberger |
| 2006/0149360 A1 | 7/2006 | Schwammenthal et al. |
| 2006/0155358 A1 | 7/2006 | LaDuca et al. |

(56) References Cited

U.S. PATENT DOCUMENTS

| | | |
|---|---|---|
| 2006/0155359 A1 | 7/2006 | Watson |
| 2006/0155366 A1 | 7/2006 | LaDuca et al. |
| 2006/0167476 A1 | 7/2006 | Burdulis, Jr. et al. |
| 2006/0173530 A1 | 8/2006 | Das |
| 2006/0178733 A1 | 8/2006 | Pinchuk et al. |
| 2006/0190070 A1 | 8/2006 | Dieck et al. |
| 2006/0193892 A1 | 8/2006 | Furst et al. |
| 2006/0229709 A1 | 10/2006 | Morris et al. |
| 2006/0241740 A1 | 10/2006 | Vardi et al. |
| 2006/0281966 A1 | 12/2006 | Peacock, III |
| 2007/0021822 A1 | 1/2007 | Boatman |
| 2007/0027526 A1 | 2/2007 | Demetriades et al. |
| 2007/0043425 A1 | 2/2007 | Hartley et al. |
| 2007/0050011 A1 | 3/2007 | Klein |
| 2007/0055350 A1 | 3/2007 | Erickson et al. |
| 2007/0055358 A1 | 3/2007 | Krolik et al. |
| 2007/0060989 A1 | 3/2007 | Deem et al. |
| 2007/0061002 A1 | 3/2007 | Paul, Jr. |
| 2007/0067014 A1 | 3/2007 | Ke et al. |
| 2007/0073373 A1 | 3/2007 | Bonsignore |
| 2007/0088425 A1 | 4/2007 | Schaeffer |
| 2007/0106368 A1 | 5/2007 | Vonderwalde |
| 2007/0112344 A1 | 5/2007 | Keilman |
| 2007/0135677 A1 | 6/2007 | Miller et al. |
| 2007/0142896 A1 | 6/2007 | Anderson et al. |
| 2007/0150051 A1 | 6/2007 | Arnault De La Menardiere et al. |
| 2007/0156167 A1 | 7/2007 | Connors et al. |
| 2007/0167898 A1 | 7/2007 | Peters et al. |
| 2007/0168018 A1 | 7/2007 | Amplatz |
| 2007/0179598 A1 | 8/2007 | Duerig |
| 2007/0185565 A1 | 8/2007 | Schwammenthal et al. |
| 2007/0208410 A1 | 9/2007 | Berra et al. |
| 2007/0213805 A1 | 9/2007 | Schaeffer et al. |
| 2007/0213807 A1 | 9/2007 | Roubin |
| 2007/0219610 A1 | 9/2007 | Israel |
| 2007/0219614 A1 | 9/2007 | Hartley |
| 2007/0219627 A1 | 9/2007 | Chu |
| 2007/0233229 A1 | 10/2007 | Berra et al. |
| 2007/0237973 A1 | 10/2007 | Purdy et al. |
| 2007/0239256 A1 | 10/2007 | Weber et al. |
| 2007/0244542 A1 | 10/2007 | Greenan et al. |
| 2007/0244543 A1 | 10/2007 | Mitchell |
| 2007/0244547 A1 | 10/2007 | Greenan |
| 2007/0250154 A1 | 10/2007 | Greenberg |
| 2007/0255388 A1 | 11/2007 | Rudakov et al. |
| 2008/0002871 A1 | 1/2008 | Gunzert-Marx et al. |
| 2008/0015673 A1 | 1/2008 | Chuter |
| 2008/0015682 A1 | 1/2008 | Majercak et al. |
| 2008/0033527 A1 | 2/2008 | Nunez et al. |
| 2008/0058918 A1 | 3/2008 | Watson |
| 2008/0064957 A1 | 3/2008 | Spence |
| 2008/0086193 A1 | 4/2008 | Thramann |
| 2008/0109058 A1 | 5/2008 | Greenberg et al. |
| 2008/0109066 A1 | 5/2008 | Quinn |
| 2008/0114444 A1 | 5/2008 | Yu |
| 2008/0114445 A1 | 5/2008 | Melsheimer et al. |
| 2008/0114446 A1 | 5/2008 | Hartley et al. |
| 2008/0140178 A1 | 6/2008 | Rasmussen et al. |
| 2008/0147173 A1 | 6/2008 | McIff et al. |
| 2008/0167704 A1 | 7/2008 | Wright et al. |
| 2008/0176271 A1 | 7/2008 | Silver et al. |
| 2008/0195191 A1 | 8/2008 | Luo |
| 2008/0249598 A1 | 10/2008 | Sherry |
| 2008/0262595 A1 | 10/2008 | Chu et al. |
| 2008/0262598 A1 | 10/2008 | Elmaleh |
| 2008/0269789 A1 | 10/2008 | Eli |
| 2008/0275540 A1 | 11/2008 | Wen |
| 2008/0275542 A1 | 11/2008 | LaDuca et al. |
| 2008/0288044 A1 | 11/2008 | Osborne |
| 2008/0294234 A1 | 11/2008 | Hartley et al. |
| 2008/0300665 A1 | 12/2008 | Lootz |
| 2008/0312732 A1 | 12/2008 | Hartley et al. |
| 2008/0319528 A1 | 12/2008 | Yribarren et al. |
| 2009/0012597 A1 | 1/2009 | Doig et al. |
| 2009/0012602 A1 | 1/2009 | Quadri |
| 2009/0030497 A1 | 1/2009 | Metcalf et al. |
| 2009/0030502 A1 | 1/2009 | Sun et al. |
| 2009/0048663 A1 | 2/2009 | Greenberg |
| 2009/0054967 A1 | 2/2009 | Das |
| 2009/0062899 A1 | 3/2009 | Dang |
| 2009/0069881 A1 | 3/2009 | Chalekian et al. |
| 2009/0069882 A1 | 3/2009 | Venturelli |
| 2009/0082841 A1 | 3/2009 | Zacharias |
| 2009/0099640 A1 | 4/2009 | Weng |
| 2009/0099647 A1 | 4/2009 | Glimsdale et al. |
| 2009/0099648 A1 | 4/2009 | Yu |
| 2009/0099649 A1 | 4/2009 | Chobotov et al. |
| 2009/0099650 A1 | 4/2009 | Bolduc et al. |
| 2009/0105809 A1 | 4/2009 | Lee et al. |
| 2009/0112233 A1 | 4/2009 | Xiao |
| 2009/0125096 A1 | 5/2009 | Chu et al. |
| 2009/0138067 A1 | 5/2009 | Pinchuk et al. |
| 2009/0149877 A1 | 6/2009 | Hanson et al. |
| 2009/0157014 A1 | 6/2009 | Osborne et al. |
| 2009/0164001 A1 | 6/2009 | Biggs et al. |
| 2009/0171437 A1 | 7/2009 | Brocker et al. |
| 2009/0182270 A1 | 7/2009 | Nanavati |
| 2009/0227997 A1 | 9/2009 | Wang |
| 2009/0240316 A1 | 9/2009 | Bruszewski |
| 2009/0248134 A1 | 10/2009 | Dierking et al. |
| 2009/0254170 A1 | 10/2009 | Hartley et al. |
| 2009/0259290 A1 | 10/2009 | Bruszewski et al. |
| 2009/0287145 A1 | 11/2009 | Cragg et al. |
| 2009/0319022 A1 | 12/2009 | Hartley et al. |
| 2010/0004728 A1 | 1/2010 | Rao |
| 2010/0029608 A1 | 2/2010 | Finley |
| 2010/0057186 A1 | 3/2010 | West et al. |
| 2010/0063575 A1 | 3/2010 | Shalev |
| 2010/0070019 A1 | 3/2010 | Shalev |
| 2010/0082091 A1 | 4/2010 | Berez |
| 2010/0161025 A1 | 6/2010 | Kuppurathanam et al. |
| 2010/0161026 A1 | 6/2010 | Brocker et al. |
| 2010/0161028 A1 | 6/2010 | Chuter et al. |
| 2010/0168838 A1 | 7/2010 | Hartley et al. |
| 2010/0174358 A1 | 7/2010 | Rabkin et al. |
| 2010/0211159 A1 | 8/2010 | Schmid |
| 2010/0249899 A1 | 9/2010 | Chuter et al. |
| 2010/0256725 A1 | 10/2010 | Rasmussen |
| 2010/0268327 A1 | 10/2010 | Bruszewski et al. |
| 2010/0274187 A1 | 10/2010 | Argentine |
| 2010/0274345 A1 | 10/2010 | Rust |
| 2010/0312326 A1 | 12/2010 | Chuter et al. |
| 2010/0318171 A1 | 12/2010 | Porter |
| 2010/0318180 A1 | 12/2010 | Porter |
| 2011/0022149 A1 | 1/2011 | Cox et al. |
| 2011/0022153 A1 | 1/2011 | Schreck et al. |
| 2011/0040366 A1 | 2/2011 | Goetz et al. |
| 2011/0093002 A1 | 4/2011 | Rucker et al. |
| 2011/0125251 A1 | 5/2011 | Cottone |
| 2011/0152998 A1 | 6/2011 | Berez et al. |
| 2011/0208289 A1 | 8/2011 | Shalev |
| 2011/0208296 A1 | 8/2011 | Duffy et al. |
| 2011/0208297 A1 | 8/2011 | Tuval et al. |
| 2011/0208298 A1 | 8/2011 | Tuval et al. |
| 2011/0218607 A1 | 9/2011 | Arbefeuille et al. |
| 2011/0218609 A1 | 9/2011 | Chobotov et al. |
| 2011/0218617 A1 | 9/2011 | Nguyen et al. |
| 2011/0257720 A1 | 10/2011 | Peterson et al. |
| 2011/0257725 A1 | 10/2011 | Argentine |
| 2011/0262684 A1 | 10/2011 | Wintsch et al. |
| 2011/0264184 A1 | 10/2011 | Heltai |
| 2011/0264192 A1 | 10/2011 | Hartley et al. |
| 2011/0270385 A1 | 11/2011 | Muzslay |
| 2011/0301702 A1 | 12/2011 | Rust et al. |
| 2011/0319983 A1 | 12/2011 | Zhu et al. |
| 2012/0143317 A1 | 6/2012 | Cam et al. |
| 2012/0158038 A1 | 6/2012 | Leschinsky |
| 2012/0172965 A1 | 7/2012 | Kratzberg |
| 2012/0179236 A1 | 7/2012 | Benary |
| 2012/0185031 A1 | 7/2012 | Ryan et al. |
| 2012/0271401 A1 | 10/2012 | Bruszewski et al. |
| 2013/0013050 A1 | 1/2013 | Shalev et al. |
| 2013/0116773 A1 | 5/2013 | Roeder et al. |
| 2013/0116775 A1 | 5/2013 | Roeder et al. |

(56) References Cited

U.S. PATENT DOCUMENTS

| | | |
|---|---|---|
| 2013/0158646 A1 | 6/2013 | Roeder |
| 2013/0197454 A1 | 8/2013 | Shibata et al. |
| 2013/0204311 A1 | 8/2013 | Kunis |
| 2013/0274866 A1 | 10/2013 | Cox et al. |
| 2013/0338753 A1 | 12/2013 | Geusen |
| 2014/0148888 A1 | 5/2014 | Barrand |
| 2014/0180378 A1 | 6/2014 | Roeder |
| 2014/0316510 A1 | 10/2014 | Berra |
| 2014/0350658 A1 | 11/2014 | Benary et al. |
| 2014/0364930 A1 | 12/2014 | Strauss et al. |
| 2015/0073534 A1 | 3/2015 | Roeder et al. |
| 2015/0196301 A1 | 7/2015 | Bodewadt et al. |
| 2015/0374383 A1 | 12/2015 | Bodewadt et al. |
| 2016/0262880 A1 | 9/2016 | Li et al. |

FOREIGN PATENT DOCUMENTS

| | | |
|---|---|---|
| CN | 1354641 A | 6/2002 |
| CN | 1748660 A | 3/2006 |
| CN | 101045022 A | 10/2007 |
| CN | 201058061 | 5/2008 |
| CN | 101998845 A | 3/2011 |
| DE | 102 103 055 A1 | 9/2002 |
| EP | 0893108 | 1/1999 |
| EP | 1 177 779 | 2/2002 |
| EP | 1 177 780 | 2/2002 |
| EP | 1 325 716 | 7/2003 |
| EP | 1759666 | 3/2007 |
| EP | 2298248 | 3/2011 |
| JP | 2000-279533 | 10/2000 |
| JP | 2002-253682 | 9/2002 |
| WO | 96/39104 A1 | 12/1996 |
| WO | 98/06355 | 2/1998 |
| WO | 99/13808 | 3/1999 |
| WO | 99/25273 | 5/1999 |
| WO | 99/34748 | 7/1999 |
| WO | 99/51165 A1 | 10/1999 |
| WO | 00/28923 | 5/2000 |
| WO | 00/74595 A1 | 12/2000 |
| WO | 00/76423 A | 12/2000 |
| WO | 01/52776 A1 | 7/2001 |
| WO | 02/083038 | 10/2002 |
| WO | 03/034948 | 5/2003 |
| WO | 03/099108 | 12/2003 |
| WO | 2004/017868 | 3/2004 |
| WO | 2004/045463 | 6/2004 |
| WO | 1470797 | 10/2004 |
| WO | 2004/100836 A1 | 11/2004 |
| WO | 2005/002466 | 1/2005 |
| WO | 2005/034809 | 4/2005 |
| WO | 2005/037138 | 4/2005 |
| WO | 2005/041781 | 5/2005 |
| WO | 2005/041783 | 5/2005 |
| WO | 2005/046524 | 5/2005 |
| WO | 2005/046526 A1 | 5/2005 |
| WO | 2006/007389 | 1/2006 |
| WO | 2006/028925 | 3/2006 |
| WO | 2006/036690 A | 4/2006 |
| WO | 2006/070372 | 7/2006 |
| WO | 2006/088905 A1 | 8/2006 |
| WO | 2006/130755 A2 | 12/2006 |
| WO | 2007/084547 | 7/2007 |
| WO | 2007/115017 A1 | 10/2007 |
| WO | 2007/144782 | 12/2007 |
| WO | 2008/008291 | 1/2008 |
| WO | 2008/021557 A1 | 2/2008 |
| WO | 2008/035337 | 3/2008 |
| WO | 2008/042266 | 4/2008 |
| WO | 2008/047092 | 4/2008 |
| WO | 2008/047354 | 4/2008 |
| WO | 2008/051704 A1 | 5/2008 |
| WO | 2008/053469 | 5/2008 |
| WO | 2008/066923 | 6/2008 |
| WO | 2008/107885 | 9/2008 |
| WO | 2008/140796 | 11/2008 |
| WO | 2009/078010 | 6/2009 |
| WO | 2009/104000 A1 | 8/2009 |
| WO | 2009/116041 | 9/2009 |
| WO | 2009/116042 | 9/2009 |
| WO | 2009/118733 | 10/2009 |
| WO | 2010/024869 | 3/2010 |
| WO | 2010/024879 | 3/2010 |
| WO | 2010/031060 | 3/2010 |
| WO | 2010/042210 A1 | 4/2010 |
| WO | 2010/045238 | 4/2010 |
| WO | 2010/062355 | 6/2010 |
| WO | 2010/088776 | 8/2010 |
| WO | 2010/111583 A1 | 9/2010 |
| WO | 2010/128162 | 11/2010 |
| WO | 2010/150208 | 12/2010 |
| WO | 2011/004374 | 1/2011 |
| WO | 2011/007354 | 1/2011 |
| WO | 2011/055364 | 5/2011 |
| WO | 2011/064782 | 6/2011 |
| WO | 2011/067764 | 6/2011 |
| WO | 2011/070576 | 6/2011 |
| WO | 2011/080738 | 7/2011 |
| WO | 2011/095979 | 8/2011 |
| WO | 2011/100290 A1 | 8/2011 |
| WO | 2011/106532 | 9/2011 |
| WO | 2011/106533 | 9/2011 |
| WO | 2011/106544 | 9/2011 |
| WO | 2011/116307 A1 | 9/2011 |
| WO | 2011/136930 | 11/2011 |
| WO | 2012/039748 | 3/2012 |
| WO | 2012/104842 | 8/2012 |
| WO | 2012/176187 | 12/2012 |
| WO | 2013/005207 | 1/2013 |
| WO | 2013/030818 | 3/2013 |
| WO | 2013/030819 | 3/2013 |
| WO | 2013/065040 | 5/2013 |
| WO | 2013/084235 | 6/2013 |
| WO | 2013/171730 | 11/2013 |
| WO | 2014/020609 | 2/2014 |
| WO | 2014/108895 | 7/2014 |
| WO | 2014/141232 | 9/2014 |
| WO | 2014/188412 | 11/2014 |
| WO | 2015/075708 | 5/2015 |

OTHER PUBLICATIONS

Fonseca A et al., "Intravascular ultrasound assessment of the novel AngioSculpt scoring balloon catheter for the treatment of complex coronary lesions," J Invasive Cardiol 20(1):21-7 (Jan. 2008).

Khlif H et al., "Contribution to the Improvement of Textile Vascular Prostheses Crimping," Trends in Applied Sciences Research 6(9):1019-1027 (2011).

An International Search Report dated Sep. 29, 2008, which issued during the prosecution of Applicant's PCT/IL08/000287.

A Written Opinion dated Sep. 29, 2008, which issued during the prosecution of Applicant's PCT/IL08/000287.

An Office Action dated Mar. 28, 2014, which issued during the prosecution of U.S. Appl. No. 13/519,971.

An International Search Report dated Feb. 4, 2011, which issued during the prosecution of Applicant's PCT/IB2010/052861.

A Written Opinion dated Feb. 4, 2011, which issued during the prosecution of Applicant's PCT/IB2010/052861.

An International Search Report dated Dec. 3, 2010, which issued during the prosecution of Applicant's PCT/IL2010/000564.

A Written Opinion dated Dec. 3, 2010, which issued during the prosecution of Applicant's PCT/IL2010/000564.

An International Search Report dated Nov. 5, 2010, which issued during the prosecution of Applicant's PCT/IL2010/000549.

A Written Opinion dated Nov. 5, 2010, which issued during the prosecution of Applicant's PCT/IL2010/000549.

An International Search Report dated Oct. 6, 2011, which issued during the prosecution of Applicant's PCT/IL2010/000999.

An International Search Report dated Mar. 10, 2011, which issued during the prosecution of Applicant's PCT/IL2010/000917.

An International Search Report dated Mar. 30, 2011, which issued during the prosecution of Applicant's PCT/IL2010/001018.

(56) References Cited

OTHER PUBLICATIONS

An International Search Report dated Apr. 18, 2011, which issued during the prosecution of Applicant's PCT/IL2010/001037.
An International Search Report dated Jul. 7, 2011, which issued during the prosecution of Applicant's PCT/IL2010/001087.
An International Search Report dated Aug. 11, 2011, which issued during the prosecution of Applicant's PCT/IL2011/000135.
An International Search Report dated Jun. 30, 2009, which issued during the prosecution of Applicant's PCT/IL2008/001621.
A Written Opinion dated Jun. 30, 2009, which issued during the prosecution of Applicant's PCT/IL2008/001621.
An International Search Report dated Mar. 11, 2009, which issued during the prosecution of Applicant's PCT/IL2007/001312.
A Written Opinion dated Mar. 11, 2009, which issued during the prosecution of Applicant's PCT/IL2007/001312.
An English translation of an Office Action dated Aug. 25, 2011, which issued during the prosecution of Chinese Patent Application No. 200880014919.9.
An Office Action dated Nov. 12, 2010, which issued during the prosecution of U.S. Appl. No. 12/447,684.
An Office Action dated Apr. 27, 2011, which issued during the prosecution of U.S. Appl. No. 12/447,684.
An Office Action dated Feb. 25, 2013, which issued during the prosecution of U.S. Appl. No. 13/031,871.
An Office Action dated Feb. 27, 2013, which issued during the prosecution of.US Patent Application No. 12/808,037.
An Extended European Search Report dated Dec. 13, 2012, which issued during the prosecution of Applicant's European App No. 08719912.1.
An International Search Report together with Written Opinion both dated Sep. 6, 2012, which issued during the prosecution of Applicant's PCT/IL2012/000190.
An International Search Report together with Written Opinion both dated Aug. 31. 2012, which issued during the prosecution of Applicant's PCT/IL2012/000148.
An Office Action dated Oct. 11, 2012, which issued during the prosecution of U.S. Appl. No. 13/031,871.
An Office Action dated Jun. 19, 2012, which issued during the prosecution of U.S. Appl. No. 12/808,037.
An International Search Report together with Written Opinion both dated Sep. 24, 2012, which issued during the prosecution of Applicant's PCT/IL2012/000060.
An International Search Report together with Written Opinion both dated Oct. 1, 2012, which issued during the prosecution of Applicant's PCT/IL2012/000241.
An International Search Report together with Written Opinion both dated Oct. 4, 2012, which issued during the prosecution of Applicant's PCT/IL2012/000269.
An International Search Report together with Written Opinion both dated Nov. 27, 2012, which issued during the prosecution of Applicant's PCT/IL2012/000300.
U.S. Appl. No. 61/264,861, filed Nov. 30, 2009.
An Office Action dated Jun. 18, 2013, which issued during the prosecution of U.S. Appl. No. 13/512,778.
An Office Action dated Feb. 28, 2014, which issued during the prosecution of U.S. Appl. No. 13/512,778.
An Interview Summary dated Sep. 25, 2014, which issued during the prosecution of U.S. Appl. No. 13/512,778.
An Interview Summary dated Apr. 24, 2014, which issued during the prosecution of U.S. Appl. No. 13/512,778.
An Office Action dated Aug. 15, 2014, which issued during the prosecution of U.S. Appl. No. 13/512,778.
Notice of Allowance dated Oct. 8, 2014, which issued during the prosecution of U.S. Appl. No. 13/512,778.
Notice of Allowance dated Nov. 7, 2014, which issued during the prosecution of U.S. Appl. No. 13/512,778.
An English Translation of an Office Action dated Jan. 16, 2015, which issued during the prosecution of Chinese Patent Application No. 201080062714.5. (the relevant part only).
An Office Action dated Feb. 5, 2015, which issued during the prosecution of U.S. Appl. No. 13/384,075.
An Office Action dated Feb. 23, 2015, which issued during the prosecution of U.S. Appl. No. 13/513,397.
European Search Report dated Feb. 26, 2015, which issued during the prosecution of Applicant's European App No. 12806964.8.
An International Search Report and a Written Opinion both dated Mar. 18, 2015, which issued during the prosecution of Applicant's PCT/IL2014/050973.
An English translation of an Office Action dated Mar. 19, 2015, which issued during the prosecution of Chinese Patent Application No. 201080036970.7.
An Office Action dated Feb. 3, 2015, which issued during the prosecution of U.S. Appl. No. 12/447,684.
Notice of Allowance dated Dec. 19, 2014, which issued during the prosecution of U.S. Appl. No. 13/512,778.
An Office Action dated Mar. 26, 2015, which issued during the prosecution of U.S. Appl. No. 13/514,240.
European Search Report dated Mar. 20, 2015, which issued during the prosecution of Applicant's European App No. 08861980.4.
An Office Action dated Jul. 30, 2015, which issued during the prosecution of U.S. Appl. No. 14/240,600.
An Office Action dated Aug. 12, 2015, which issued during the prosecution of U.S. Appl. No. 13/513,397.
An International Search Report and a Written Opinion both dated Jul. 30, 2014, which issued during the prosecution of Applicant's PCT/IL2014/050174.
European Search Report dated Jun. 12, 2014, which issued during the prosecution of Applicant's European App No. 12855964.8.
An Office Action dated Sep. 11, 2015, which issued during the prosecution of U.S. Appl. No. 14/001,641.
An Office Action dated Sep. 23, 2015, which issued during the prosecution of U.S. Appl. No. 13/384,075.
An Office Action dated Oct. 2, 2015, which issued during the prosecution of U.S. Appl. No. 13/577,161.
An Office Action dated May 15, 2015, which issued during the prosecution of U.S. Appl. No. 13/577,161.
An Office Action dated May 28, 2015, which issued during the prosecution of U.S. Appl. No. 14/240,600.
European Search Report dated Apr. 22, 2015, which issued during the prosecution of Applicant's European App No. 12828495.7.
An Office Action dated Apr. 14, 2015, which issued during the prosecution of U.S. Appl. No. 14/130,213.
Invitation to Pay Additional Fees dated May 13, 2014, which issued during the prosecution of Applicant's PCT/IL2014/050019.
Invitation to Pay Additional Fees dated May 8, 2014, which issued during the prosecution of Applicant's PCT/IL2014/050174.
An Advisory Action dated Feb. 13, 2014, which issued during the prosecution of U.S. Appl. No. 13/807,880.
An Office Action dated Apr. 28, 2014, which issued during the prosecution of U.S. Appl. No. 13/939,798.
An Office Action dated Apr. 24, 2014, which issued during the prosecution of U.S. Appl. No. 13/380,278.
An Office Action dated Apr. 10, 2014, which issued during the prosecution of U.S. Appl. No. 13/807,906.
An English translation of an Office Action dated Jan. 28, 2014, which issued during the prosecution of Chinese Patent Application No. 201080036970.7.
European Search Report dated Feb. 17, 2014, which issued during the prosecution of Applicant's European App No. 12803376.
An Office Action dated Jul. 24, 2014, which issued during the prosecution of Canadian Patent Application No. 2,768,228.
European Search Report dated Jan. 18, 2016 which issued during the prosecution of Applicant's European App No. 10799521.9.
European Search Report dated Oct. 27, 2015 which issued during the prosecution of Applicant's European App No. 10835608.0.
An Office Action dated Feb. 23, 2016, which issued during the prosecution of U.S. Appl. No. 14/416,236.
An Office Action dated Mar. 7. 2016, which issued during the prosecution of U.S. Appl. No. 14/240,600.
An Office Action dated Feb. 1, 2016, which issued during the prosecution of U.S. Appl. No. 14/241,793.

(56) References Cited

OTHER PUBLICATIONS

An Office Action dated Feb. 19, 2016, which issued during the prosecution of U.S. Appl. No. 13/807,880.
An International Search Report and a Written Opinion both dated Feb. 17, 2016, which issued during the prosecution of Applicant's PCT/IL2015/051221.
European Search Report dated Mar. 11, 2016 which issued during the prosecution of Applicant's European App No. 11739497.3.
European Search Report dated Mar. 15, 2016 which issued during the prosecution of Applicant's European App No. 13825456.0.
An Office Action dated Mar. 28, 2016, which issued during the prosecution of U.S. Appl. No. 14/362,194.
Scurr et al., "Fenestrated Aortic Stent Grafts," Semin Intervent Radiol. Jun. 2007; 24(2): 211-220.
An International Search Report and a Written Opinion both dated Apr. 22, 2016, which issued during the prosecution of Applicant's PCT/IL2016/050049.
Fransen GA, Desgranges P, Laheij RJ, Harris PL, Becquemin JP; EUROSTAR Collaborators. Frequency, predictive factors, and consequences of stent-graft kink following endovascular AAA repair. J Endovasc Ther. Oct. 2003;10(5):913-918.
An Invitation to pay additional fees dated Apr. 12, 2016, which issued during the prosecution of Applicant's PCT/IL2016/050014.
U.S. Appl. No. 61/775,964, filed Mar. 11, 2013.
Extended European Search Report issued in Application No. 10832752.9, dated May 23, 2016.
International Search Report and Written Opinion in PCT/IL2016/05004, dated Jun. 21, 2016.
Office Action issued in related Chinese Application No. 201480026943.X, dated Jun. 30, 2016.
Final Office Action issued U.S. Appl. No. 14/241,793, dated Aug. 3, 2016.
Extended European Search Report issued in related European Application No. 14762507.3, dated Aug. 31, 2016.
Extended European Search Report issued in European Application No. 10834308.8, dated Sep. 22, 2016.
Extended European Search Report issued in European Application No. 14801036.6, dated Oct. 27, 2016.
Non-Final Office Action issued in U.S. Appl. No. 14/240,600, dated Nov. 2, 2016.
Notice of Allowance issued in U.S. Appl. No. 14/362,194, dated Nov. 10, 2016.
Office Action issued in Chinese Application No. 201510685240.4, dated Dec. 27, 2016.
Non-Final Office Action issued in U.S. Appl. No. 14/518,542, dated Jan. 12, 2017.
Patrick O'Gara, M.D., Aortic Aneurysm, Circulation, 2003.
Second Office Action issued in Chinese Application No. 201480012648.9, dated Jul. 22, 2016.
Non-Final Office Action issued in U.S. Appl. No. 14/400,699, dated Dec. 7, 2016.

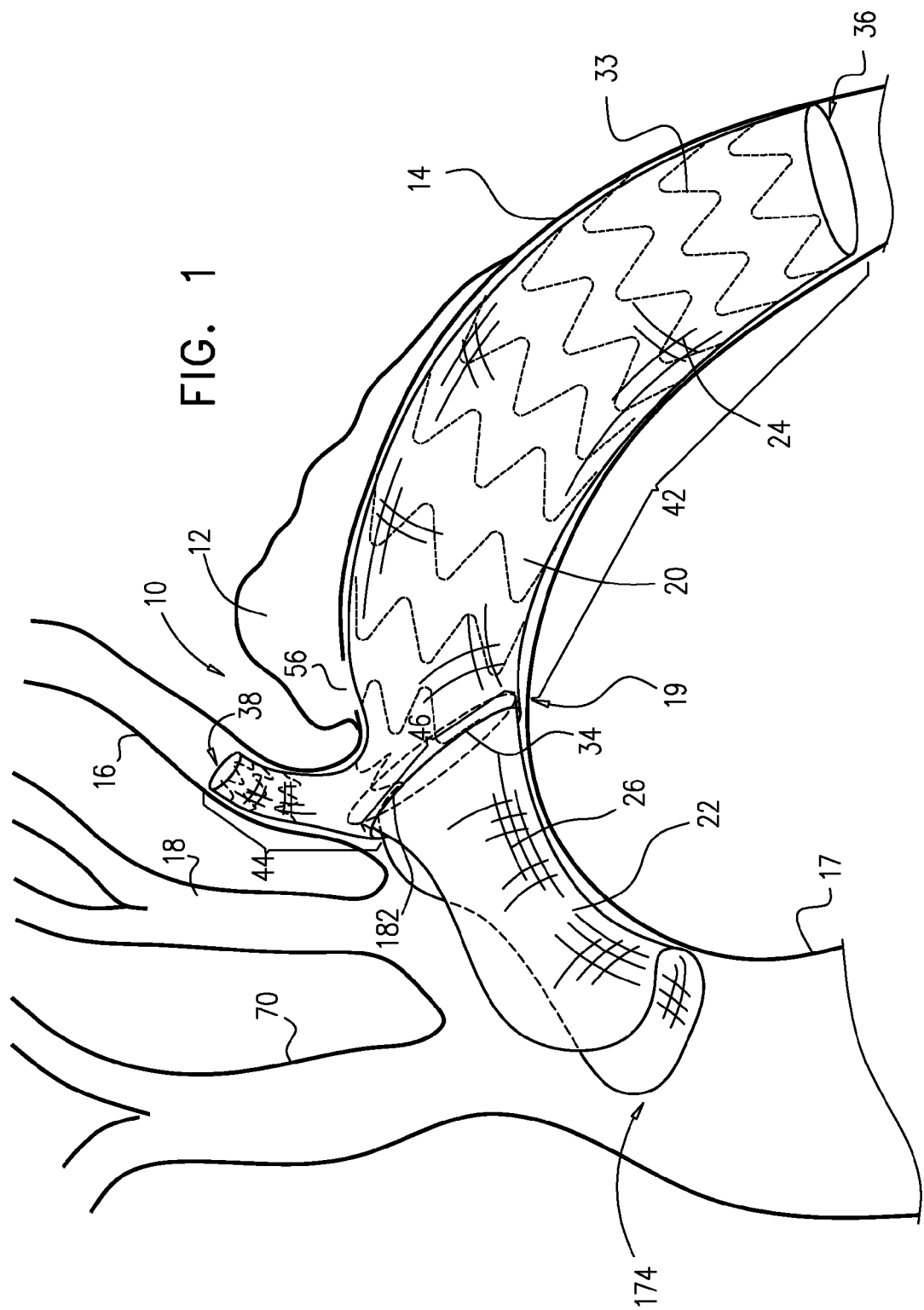

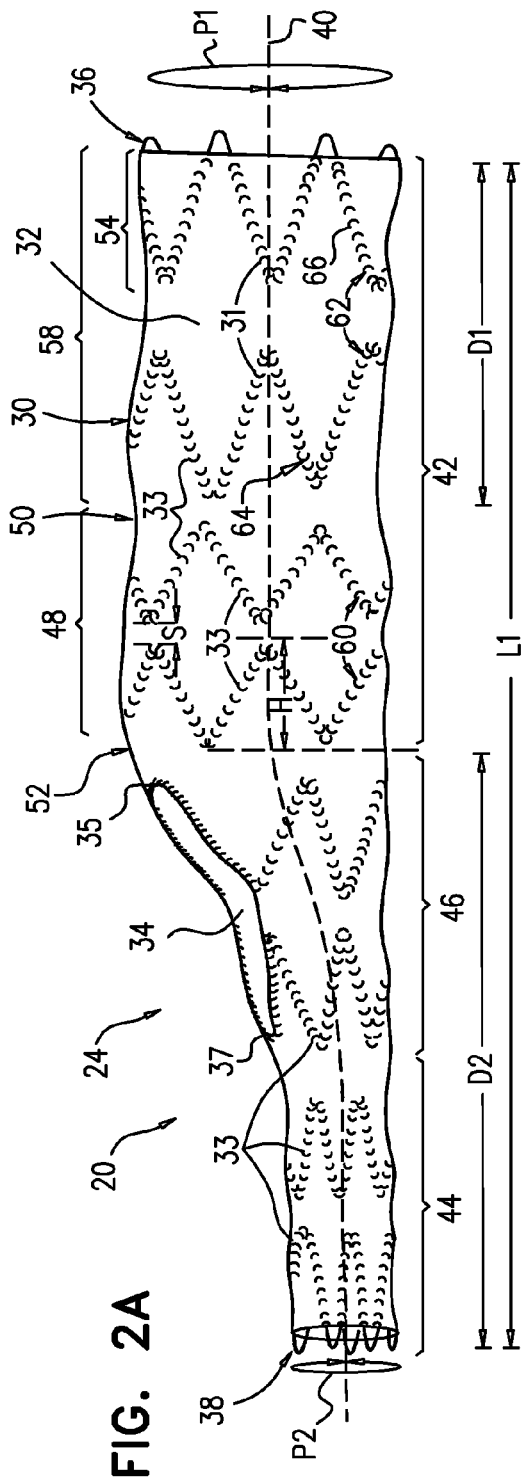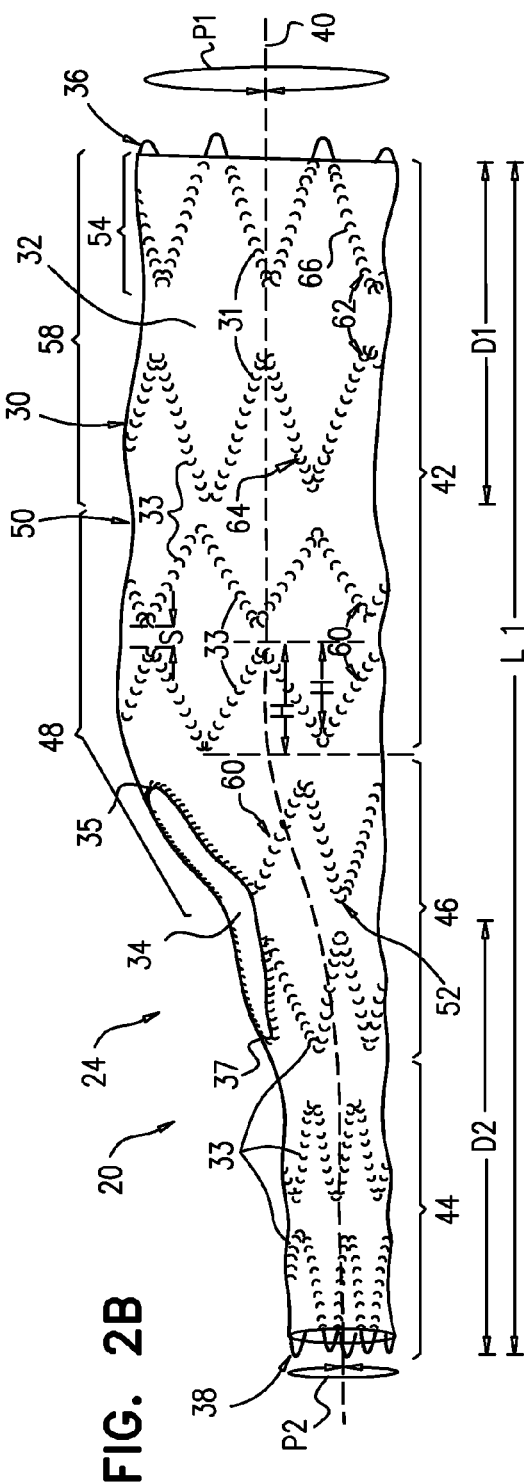
FIG. 2A
FIG. 2B

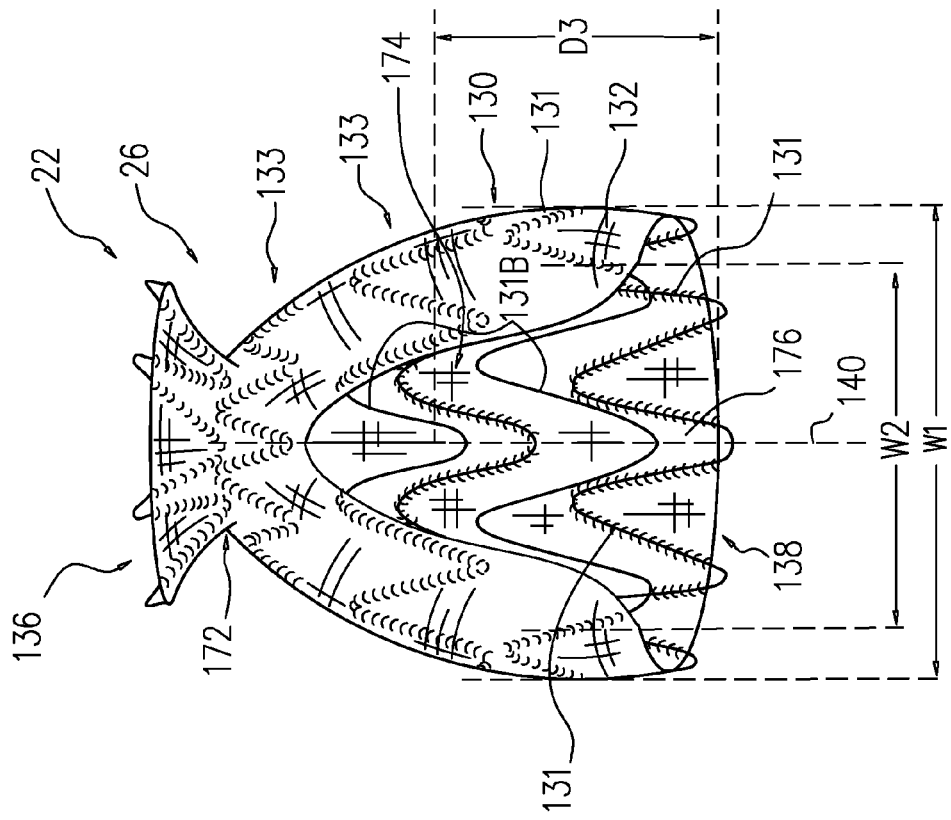

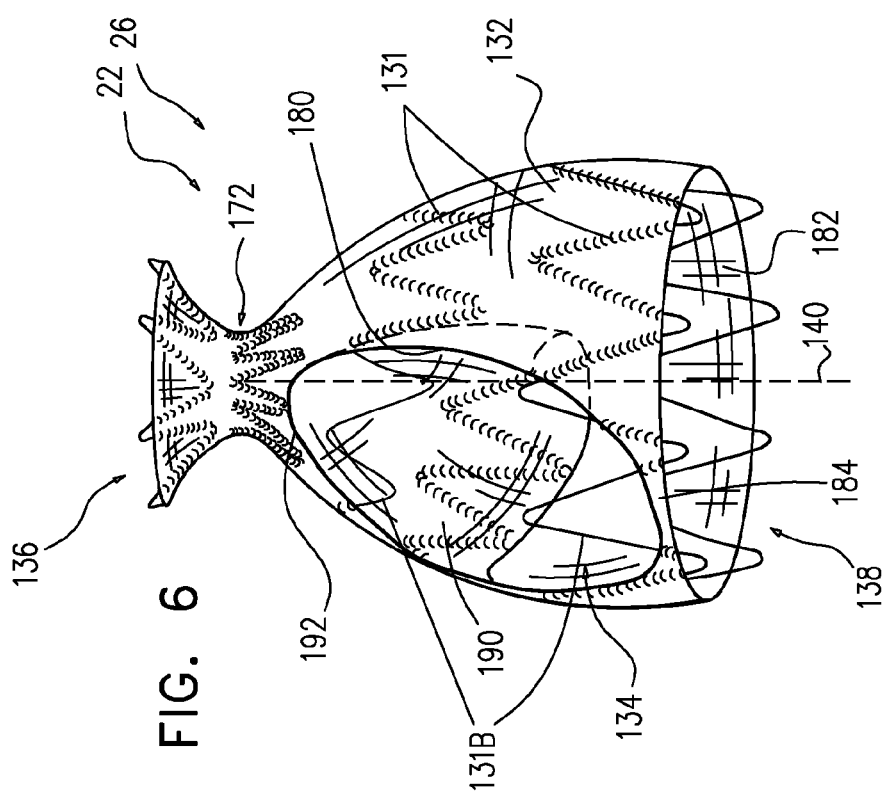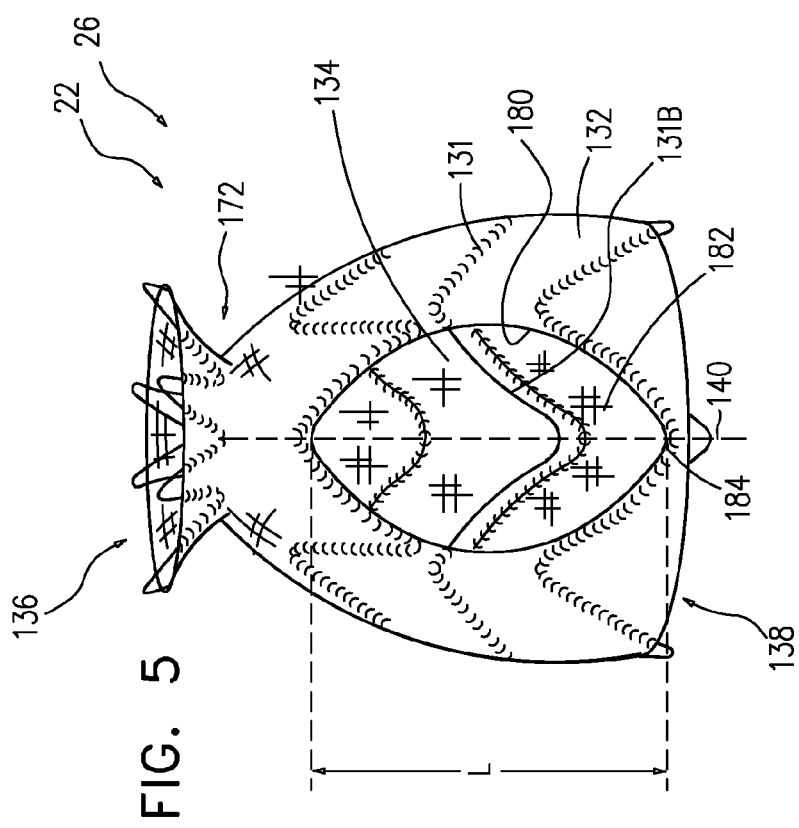

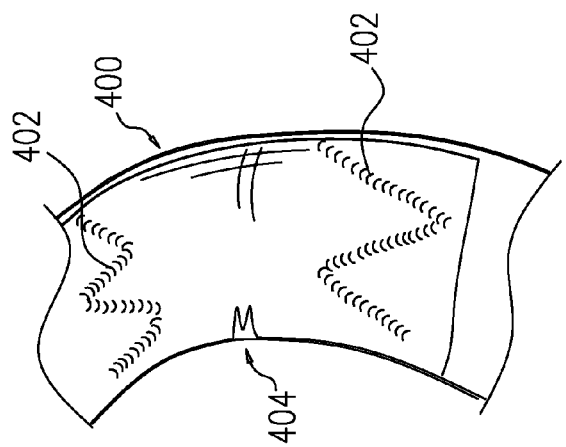
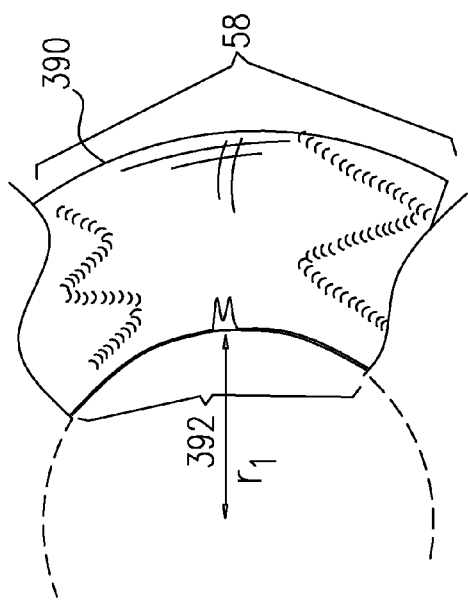
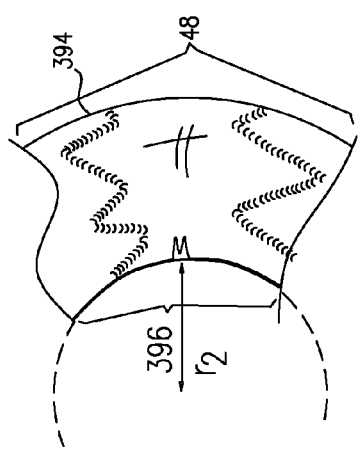

MULTI-COMPONENT STENT-GRAFT SYSTEM FOR AORTIC DISSECTIONS

CROSS-REFERENCE TO RELATED APPLICATION

The present application is the U.S. national stage of International Application PCT/IL2014/050174, filed Feb. 18, 2014, which claims priority from U.S. Provisional Application 61/775,964, filed Mar. 11, 2013, which is assigned to the assignee of the present application and is incorporated herein by reference.

FIELD OF THE APPLICATION

The present application relates generally to prostheses and surgical methods, and specifically to tubular prostheses, including endovascular grafts and stent-grafts, and surgical techniques for using the prostheses to maintain patency of body passages such as blood vessels, and treating dissections of arterial walls and/or aneurysms.

BACKGROUND OF THE APPLICATION

Blood vessels occasionally weaken or even rupture. For example, in the aortic artery, the vascular wall can weaken or tear, resulting in dangerous conditions such as aneurysm and dissection. Treatment of such conditions can be performed by implanting a prosthesis within the vascular system using minimally-invasive surgical procedures. An endoluminal prosthesis typically includes one or more stents affixed to graft material and is delivered to the treatment site by endovascular insertion. Once the endoluminal prosthesis is radially enlarged, it should remain in place indefinitely by self-attachment to the vessel wall, acting as a substitute vessel for the flow of blood or other fluids.

Aortic dissection is a tear or partial tear in the inner wall of the aorta, which causes blood to flow between the layers of the wall of the aorta, forcing the layers apart. Aortic dissections may be divided into two types in accordance with the Stanford classification: Type A dissections involve the ascending aorta and/or aortic arch, and possibly the descending aorta. Type B dissections involves the descending aorta or the arch (distal to right brachiocephalic artery origin), without involvement of the ascending aorta.

SUMMARY OF THE APPLICATION

In some applications of the present invention, a multi-component stent-graft system is provided for treating a Type B aortic dissection. The system is configured to be deployed in the thoracic aorta and the left subclavian artery, and, optionally, the left common carotid artery. The stent-grafts of the system are assembled in situ to accommodate the dimensions of the particular patient's anatomy, generally without requiring prior customization of the stent-grafts or in situ modifications to the stent-grafts, which might be expensive and/or complex. Typically, upon deployment, the multi-component stent-graft system defines a blood-flow path from the ascending aorta, over the aortic arch, and to the descending aorta. The multi-component stent-graft system additionally provides or allows blood-flow paths to the three branches of the aortic arch.

The multi-component stent-graft system comprises a main module and, for some applications, a secondary module. The main module comprises a generally tubular main stent-graft, and the secondary module comprises a non-bifurcated secondary stent-graft. The stent-grafts are configured to assume radially-compressed states for delivery, and radially-expanded states upon being deployed.

The main stent-graft typically comprises a main generally tubular support element and a main covering element that is attached to and at least partially covers the main support element. The support element typically comprises a plurality of main structural stent elements. For some applications, the main structural stent elements are arranged as a plurality of circumferential stent springs.

The main covering element and the main support element are shaped so as to together define a lateral fenestration, e.g., exactly one lateral fenestration, through the main stent-graft, when the main stent-graft is unconstrained in its radially-expanded state.

For some applications, when the main stent-graft is unconstrained in its radially-expanded state, i.e., no forces are applied to the stent-graft by a delivery tool, walls of a blood vessel, or otherwise, a first perimeter of a distal main-module end of the main stent-graft (and the main module) is greater than a second perimeter of a proximal main-module end of the main stent-graft (and the main module). For example, the first perimeter may equal at least 150% of the second perimeter, such as at least 200%, at least 250%, at least 300%, or at least 400% of the second perimeter.

For some applications, the main stent-graft is sized and configured to positioned such that (a) a distal, radially larger, descending-aorta axial portion of the stent-graft, including the distal main-module end thereof, is disposed in the aorta downstream from the bifurcation with the left subclavian artery, at least partially in the upper part of the descending aorta, (b) a proximal, radially smaller, supra-arch axial portion of the main stent-graft, including the proximal main-module end thereof, is disposed in the left subclavian artery, and (c) an arch axial portion, axially between the descending-aorta axial portion and the supra-arch axial portion, is disposed in the aortic arch.

For some applications, when the main stent-graft is unconstrained in its radially-expanded state, the main stent-graft includes a dissection-reinforcement axial portion, which (a) includes a portion of the main structural stent elements, (b) has a proximal dissection-reinforcement end that is disposed along the stent-graft no more than 20 mm proximal to the proximal fenestration end, and/or (c) extends along the stent-graft for a distance equal to between 5% and 32% of a greatest perimeter of the stent-graft distally to the distal fenestration end.

For some applications, the dissection-reinforcement axial portion has a radial strength that is at least 10% greater than an average radial strength of the entire main stent-graft. This greater strength increases the force that the dissection-reinforcement axial portion applies to a tear of the aortic dissection, thereby sealing the tear. (It is noted that providing the entire length of the main stent-graft with a high strength has at least two drawbacks: stent-grafts with higher strengths are more difficult to deploy, and are more likely to cause damage to the vasculature.) For some applications, the dissection-reinforcement axial portion is configured to be generally straight when the main stent-graft is unconstrained in the radially-expanded state.

For some applications, the main structural stent elements of the dissection-reinforcement axial portion are arranged as a plurality of circumferential stent springs of the dissection-reinforcement axial portion. For some applications, a height, measured axially along the main stent-graft, of at least one of the stent springs of the dissection-reinforcement axial portion varies by less than 10% around a circumference of the stent spring when the main stent-graft is unconstrained in the radially-expanded state.

For some applications, the portion of structural stent elements included by the dissection-reinforcement axial portion is a first portion of the structural stent elements, and when the stent-graft is unconstrained in the radially-expanded state: (a) the main stent-graft includes a distal-end axial portion, which includes a second portion of the structural stent elements, (b) the distal-end axial portion axially extends along the stent-graft from the distal main-module end for a distance equal to between 5% and 32% of a greatest perimeter of the main stent-graft distally to a distal end of the lateral fenestration, and (c) the distal-end axial portion has a radial strength that is at least a 10% greater than the average radial strength of the entire main stent-graft.

For some applications, the dissection-reinforcement axial portion includes a first plurality of the stent springs, and the main stent-graft includes a distal axial portion, which includes a second plurality of the stent springs. The distal axial portion is disposed along the main stent-graft distal and axially adjacent to the distal dissection-reinforcement end, and extends along the main stent-graft for a distance equal to between 5% and 32% of the greatest perimeter of the main stent-graft distally to the distal fenestration end. Typically, the distal axial portion extends to and reaches the distal main-module end. The stent springs have respective average heights, measured axially along the main stent-graft (the height of each stent spring is averaged circumferentially around the stent-graft). An average of the average heights of the first plurality of the stent springs is less than 75% of the average height of a proximal-most one of the second plurality of the stent springs. For these applications, the dissection-reinforcement axial portion is typically configured to be generally straight when the main stent-graft is unconstrained in the radially-expanded state.

The secondary stent-graft typically comprises a secondary generally tubular support element and a secondary covering element that is attached to and at least partially covers the secondary support element. The support element typically comprises a plurality of secondary structural stent elements. When the secondary module (and the secondary stent-graft) is unconstrained in the radially-expanded state thereof:
  the secondary module is shaped so as to define a proximal secondary-module end, a sealing interface distal to the proximal secondary-module end, and a central longitudinal axis therebetween. The sealing interface is sized and configured to form a blood-impervious seal with the lateral fenestration of the main module;
  the secondary module is shaped so as to define a distal secondary-module end; and
  the secondary covering element is shaped so as to define at least one lateral opening that begins at and extends from the proximal secondary-module end toward the sealing interface along the central longitudinal axis for a distance equal to at least 50% of a greatest width of the secondary module, measured perpendicular to the central longitudinal axis.

For some applications, at least one of the secondary structural stent elements traverses the lateral opening when the secondary module is unconstrained in the radially-expanded state thereof. Such traversal may provide additional structural strength to the secondary module at the lateral opening.

In some applications of the present invention, another configuration of secondary module is provided. In this configuration, when the secondary module is unconstrained in the radially-expanded state thereof:
  the at least one lateral opening includes at least first and second lateral openings;
  the secondary covering element is shaped so as to define the first and second lateral openings, each of which begins at and extends from the proximal secondary-module end toward the sealing interface along the central longitudinal axis for the distance equal to at least 50% of the greatest width of the secondary module;
  the first and second lateral openings face in different first and second radial directions extending from the central longitudinal axis; and
  the first and the second lateral openings at least partially axially overlap along the central longitudinal axis.

For some applications, the first and the second lateral openings axially coincide along the central longitudinal axis. For some applications, the first and the second radial directions are opposite each other; in other words the first and second lateral openings face in radially-opposite directions.

In some applications of the present invention, further alternative configurations of secondary module are provided. In these configurations, when the secondary module is unconstrained in the radially-expanded state thereof, (a) the secondary covering element is shaped so as to define at least one secondary-module lateral fenestration disposed distal to the proximal secondary-module end and proximal to the sealing interface, and (b) a greatest axial length of the secondary-module lateral fenestration equals at least 33% of the first perimeter of the distal main-module end of the main stent-graft of the main module, when the main module is unconstrained in the radially-expanded state thereof. For some applications, a greatest width of the secondary-module lateral fenestration, measured circumferentially around the secondary module, equals at least 16% of the first perimeter of the distal main-module end of the main stent-graft of the main module.

For some applications, the secondary module further comprises a flexible sheet, which (a) is blood-sealingly joined to a portion of the secondary border, which portion extends around at least 25% of a perimeter of the secondary border and includes a distal end of the secondary border when the secondary module is unconstrained in the radially-expanded state thereof, and (b) extends radially inward from the secondary border (toward or past the central longitudinal axis) when the secondary module is unconstrained in the radially-expanded state thereof. For some applications, a portion of the secondary structural stent elements are attached to the flexible sheet, which facilitates the radially-inward extension of the flexible sheet from secondary border.

There is therefore provided, in accordance with an application of the present invention, apparatus including a generally tubular stent-graft, which has distal and proximal stent-graft ends and includes:
  a generally tubular support element, which includes a plurality of structural stent elements; and
  a covering element that is attached to and at least partially covers the support element,
  wherein when the stent-graft is unconstrained in a radially-expanded state:
    the covering element and the support element are shaped so as to together define a lateral fenestration having distal and proximal fenestration ends, a first perimeter of the distal stent-graft end equals at least 200% of a second perimeter of the proximal stent-graft end, and the stent-graft includes a dissection-reinforcement axial portion, which (a) includes a portion of the structural stent elements, (b) has (i) a distal dissection-reinforcement end and (ii) a proximal dissection-reinforcement end that is disposed along the stent-graft no more than 20 mm proximal to the proximal fenestration end, (c) extends along the stent-graft for a distance equal to between 5% and 32% of a greatest perimeter of the stent-graft distally to the distal fenestration end, and (d) has a radial strength that is at least 10% greater than an average radial strength of the entire stent-graft.

For some applications:

the portion of the structural stent elements included by the dissection-reinforcement axial portion is a first portion of the structural stent elements, and when the stent-graft is unconstrained in the radially-expanded state:

the stent-graft includes a distal-end axial portion, which includes a second portion of the structural stent elements, and the distal-end axial portion axially extends along the stent-graft from the distal end of stent-graft for a distance equal to between 5% and 32% of a greatest perimeter of the stent-graft distally to the distal fenestration end, and the distal-end axial portion has a radial strength that is at least a 10% greater than the average radial strength of the entire stent-graft.

For some applications, an axial length of the dissection-reinforcement axial portion is between 1 and 3 cm when the stent-graft is unconstrained in the radially-expanded state.

For some applications, the proximal dissection-reinforcement end is disposed along the stent-graft no more proximal than the distal fenestration end when the stent-graft is unconstrained in the radially-expanded state. Alternatively, for some applications, the proximal dissection-reinforcement end is disposed along the stent-graft between the distal fenestration end and the proximal fenestration end, inclusive, when the stent-graft is unconstrained in the radially-expanded state.

For some applications, a distance between the distal dissection-reinforcement end and the distal stent-graft end equals between 32% and 160% of a largest perimeter of the stent-graft when the stent-graft is unconstrained in the radially-expanded state.

For some applications, the dissection-reinforcement axial portion extends along the stent-graft for a distance equal to between 10% and 22% of a greatest perimeter of the stent-graft distally to the distal fenestration end when the stent-graft is unconstrained in the radially-expanded state.

For some applications, the first perimeter equals at least 250% of the second perimeter.

For any of the applications described above, the dissection-reinforcement axial portion may be configured to be generally straight when the stent-graft is unconstrained in the radially-expanded state.

For any of the applications described above, the structural stent elements of the dissection-reinforcement axial portion may be arranged as a plurality of circumferential stent springs, and a height, measured axially along the stent-graft, of at least one of the stent springs may vary by less than 10% around a circumference of the stent spring when the stent-graft is unconstrained in the radially-expanded state.

For any of the applications described above, the structural stent elements of the dissection-reinforcement axial portion may be arranged as a plurality of circumferential stent springs, and for each one of the stent springs, a height, measured axially along the stent-graft, of the stent spring may vary by less than 10% around a circumference of the stent spring when the stent-graft is unconstrained in the radially-expanded state.

For any of the applications described above, the first perimeter may be between 5 and 15 cm, and the second perimeter may be between 2.5 and 5.7 cm.

For any of the applications described above, the stent-graft may be shaped so as to define exactly one lateral fenestration when the stent-graft is unconstrained in the radially-expanded state.

For any of the applications described above, the lateral fenestration may be an inferior first lateral fenestration, which faces in a first radial direction, and when the main stent-graft is unconstrained in the radially-expanded state, the main covering element and the main support element may be shaped so as to together define a superior second lateral fenestration, which faces in a second radial direction generally opposite the first radial direction.

There is further provided, in accordance with an application of the present invention, apparatus including a generally tubular stent-graft, which has distal and proximal stent-graft ends and includes:

a generally tubular support element, which includes a plurality of structural stent elements arranged as a plurality circumferential stent springs; and a covering element that is attached to and at least partially cover the support element, wherein when the stent-graft is unconstrained in a radially-expanded state:

the covering element and the support element are shaped so as to together define a lateral fenestration having distal and proximal fenestration ends, a first perimeter of the distal stent-graft end equals at least 200% of a second perimeter of the proximal stent-graft end, the stent-graft includes a dissection-reinforcement axial portion, which (a) includes a first plurality of the stent springs, (b) has (i) a distal dissection-reinforcement end and (ii) a proximal dissection-reinforcement end that is disposed along the stent-graft no more than 20 mm proximal to the proximal fenestration end, (c) extends along the stent-graft for a distance equal to between 5% and 32% of a greatest perimeter of the stent-graft distally to the distal fenestration end, and (d) is configured to be generally straight, the stent-graft includes a distal axial portion, which (a) includes a second plurality of the stent springs, (b) is disposed along the stent-graft distal and axially adjacent to the distal dissection-reinforcement end, (c) extends along the stent-graft for a distance equal to between 5% and 32% of the greatest perimeter of the stent-graft distally to the distal fenestration end, the stent springs have respective average heights, measured axially along the stent-graft, and an average of the average heights of the first plurality of the stent springs is less than 75% of the average height of a proximal-most one of the second plurality of the stent springs.

For some applications, each of the average heights of the first plurality of the stent springs is less than 75% of the average heights of the proximal-most one of the second plurality of stent springs when the stent-graft is unconstrained in the radially-expanded state.

For some applications, the average of the average heights of the first plurality of the stent springs is less than 75% of the average height of a second one of the second plurality of stent springs, other than the proximal-most one of the second plurality of stent springs when the stent-graft is unconstrained in the radially-expanded state.

For some applications, the average of the average heights of the first plurality of the stent springs is less than 75% of each of the average heights of the second plurality of stent springs when the stent-graft is unconstrained in the radially-expanded state.

For some applications, the distal axial portion is configured to be generally straight when the stent-graft is unconstrained in the radially-expanded state.

For some applications, an axial length of the dissection-reinforcement axial portion is between 1 and 3 cm when the stent-graft is unconstrained in the radially-expanded state.

For some applications, the proximal dissection-reinforcement end is disposed along the stent-graft no more proximal than the distal fenestration end when the stent-graft is unconstrained in the radially-expanded state.

For some applications, the proximal dissection-reinforcement end is disposed along the stent-graft between the distal fenestration end and the proximal fenestration end, inclusive, when the stent-graft is unconstrained in the radially-expanded state.

For some applications, an axial spacing between two of the first plurality of the stent springs equals less than 10% of an average of the average heights of the two stent springs.

For some applications, the first perimeter equals at least 300% of the second perimeter.

For some applications, the dissection-reinforcement axial portion extends along the stent-graft for a distance equal to between 10% and 32% of the greatest perimeter of the stent-graft distally to the distal fenestration end when the stent-graft is unconstrained in the radially-expanded state.

For some applications, the distal axial portion extends to and reaches the distal stent-graft end.

For any of the applications described above, the average height of at least one of the first plurality of stent springs may vary by less than 10% around a circumference of the stent spring when the stent-graft is unconstrained in the radially-expanded state.

For any of the applications described above, for each one of the first plurality of stent springs, the average height thereof may vary by less than 10% around a circumference of the stent spring when the stent-graft is unconstrained in the radially-expanded state.

For any of the applications described above, optionally:
if the distal axial portion, when the stent-graft is in the radially-expanded state, is placed and constrained in a first curved tube having a circular cross-section and an inner diameter equal to an outer diameter of the distal axial portion, the distal axial portion experiences kinking only when at least an axial portion of the first curved tube has less than a first radius of curvature, and if the dissection-reinforcement axial portion, when the stent-graft is in the radially-expanded state, is placed and constrained in a second curved tube having a circular cross-section and an inner diameter equal to an outer diameter of the dissection-reinforcement axial portion, the dissection-reinforcement axial portion experiences kinking only when at least an axial portion of the second curved tube has less than a second radius of curvature, which second radius of curvature is at least 30% less than the first radius of curvature.

For any of the applications described above, the lateral fenestration may be an inferior first lateral fenestration, which faces in a first radial direction, and when the main stent-graft is unconstrained in the radially-expanded state, the main covering element and the main support element may be shaped so as to together define a superior second lateral fenestration, which faces in a second radial direction generally opposite the first radial direction.

There is still further provided, in accordance with an application of the present invention, apparatus including a stent-graft system, which includes:

a main module, which has distal and proximal main-module ends, and includes a generally tubular main stent-graft, which includes (a) a main generally tubular support element, which includes main structural stent elements, and (b) a main covering element that is attached to and at least partially covers the support element, wherein the main covering element and the main support element are shaped so as to together define a lateral fenestration when the main module is unconstrained in a radially-expanded state thereof; and a secondary module, which includes a non-bifurcated secondary stent-graft, which includes (a) a secondary support element, which includes secondary structural stent elements, and (b) a secondary covering element that is attached to and at least partially covers the secondary support element, wherein when the secondary module is unconstrained in a radially-expanded state thereof:

the secondary module is shaped so as to define (a) a proximal secondary-module end, (b) a sealing interface distal to the proximal secondary-module end, and (c) a central longitudinal axis therebetween, wherein the sealing interface is sized and configured to form a blood-impervious seal with the lateral fenestration of the main module, and the secondary covering element is shaped so as to define at least one lateral opening that begins at and extends from the proximal secondary-module end toward the sealing interface along the central longitudinal axis for a distance equal to at least 50% of a greatest width of the secondary module, measured perpendicular to the central longitudinal axis.

For some applications, a greatest width of the at least one lateral opening, measured circumferentially around the secondary module, equals at least 90 degrees circumferentially around the proximal secondary-module end, the 90 degrees being measured at the sealing interface.

For some applications, at least one of the secondary structural stent elements traverses the at least one lateral opening when the secondary module is unconstrained in the radially-expanded state thereof.

For some applications, the at least one lateral opening extends from the proximal secondary-module end toward the sealing interface along at least 70% of a greatest width of the secondary module, measured perpendicular to the central longitudinal axis when the secondary module is unconstrained in the radially-expanded state thereof.

For some applications, the cross-sectional area of the secondary module, measured perpendicular to the central longitudinal axis, gradually tapers from the proximal secondary-module end to the sealing interface when the secondary module is unconstrained in the radially-expanded state thereof.

For any of the applications described above, when the secondary module is unconstrained in the radially-expanded state thereof:

the at least one lateral opening may include at least first and second lateral openings, the secondary covering element may be shaped so as to define the first and the second lateral openings, each of extends from the proximal secondary-module end toward the sealing interface along the central longitudinal axis for the distance equal to at least 50% of the greatest width of the secondary module, the first and the second lateral openings may face in different first and second radial directions extending from the central longitudinal axis, and the first and the second lateral openings may at least partially axially overlap along the central longitudinal axis.

For some applications, the first and the second lateral openings axially coincide along the central longitudinal axis. For some applications, the first and the second radial directions are opposite each other. For some applications, the secondary covering element is shaped so as to define two portions, which (a) extend to and reach the proximal secondary-module end, and (b) are shaped so as to define respective concave inner surfaces that face each other and the central longitudinal axis, and (c) are not joined to each other at the proximal secondary-module end.

For any of the applications described above, the at least one lateral opening may include exactly one lateral opening. For some applications, when the secondary module is unconstrained in the radially-expanded state thereof, the lateral opening faces in a first radial direction extending from the central longitudinal axis, and a portion of the secondary covering element that faces in a second radial direction opposite the first radial direction extends to and reaches the proximal secondary-module end.

For any of the applications described above, a first perimeter of the distal main-module end may equal at least 200%, e.g., at least 300%, of a second perimeter of the proximal main-module end when the main module is unconstrained in the radially-expanded state thereof.

For any of the applications described above:

the lateral fenestration may be an inferior first lateral fenestration, which faces in a first radial direction, when the main stent-graft is unconstrained in the radially-expanded state, the main covering element and the main support element may be shaped so as to together define a superior second lateral fenestration, which faces in a second radial direction generally opposite the first radial direction, the stent-graft system may further include a generally tubular tertiary stent-graft, and the main and the tertiary stent-grafts may be configured such that the tertiary stent-graft forms a blood-impervious seal with the main stent-graft around the superior second lateral fenestration when the tertiary stent-graft is disposed therethrough, and the main stent-graft is in the radially-expanded state thereof and the tertiary stent-graft is in a radially-expanded state thereof.

There is additionally provided, in accordance with an application of the present invention, apparatus including a stent-graft system, which includes:

a main module, which has distal and proximal main-module ends, and includes a generally tubular main stent-graft, which includes (a) a main generally tubular support element, which includes main structural stent elements, and (b) a main covering element that is attached to and at least partially covers the support element, wherein the main covering element and the main support element are shaped so as to together define a main-module lateral fenestration when the main module is unconstrained in a radially-expanded state thereof; and a secondary module, which includes a non-bifurcated secondary stent-graft, which includes (a) a secondary support element, which includes secondary structural stent elements, and (b) a secondary covering element that is attached to and at least partially covers the secondary support element, wherein when the secondary module is unconstrained in a radially-expanded state thereof:

the secondary module is shaped so as to define (a) a proximal secondary-module end, (b) a sealing interface distal to the proximal secondary-module end, and (c) a central longitudinal axis therebetween, wherein the sealing interface is sized and configured to form a blood-impervious seal with the main-module lateral fenestration of the main module, the secondary covering element is shaped so as to define at least one secondary-module lateral fenestration disposed distal to the proximal secondary-module end and proximal to the sealing interface, and a greatest axial length of the secondary-module lateral fenestration, measured parallel to the central longitudinal axis, equals at least 33% of a first perimeter of the distal main-module end when the main module is unconstrained in the radially-expanded state thereof.

For some applications, at least one of the secondary structural stent elements traverses the secondary-module lateral fenestration.

For some applications, the greatest axial length of the secondary-module lateral fenestration equals at least 50% of the first perimeter of the distal main-module end when the secondary module is unconstrained in the radially-expanded state thereof.

For some applications, the cross-sectional area of the secondary module gradually tapers from the proximal secondary-module end to the sealing interface when the secondary module is unconstrained in the radially-expanded state thereof.

For any of the applications described above, the at least one secondary-module lateral fenestration may include exactly one secondary-module lateral fenestration. For some applications, when the secondary module is unconstrained in the radially-expanded state thereof, the secondary-module lateral fenestration faces in a first radial direction extending from the central longitudinal axis, and a portion of the secondary covering element that faces in a second radial direction opposite the first radial direction extends to and reaches the proximal secondary-module end.

For any of the applications described above, the first perimeter of the distal main-module end may equal at least 200%, e.g., at least 300%, of a second perimeter of the proximal main-module end when the main module is unconstrained in the radially-expanded state thereof.

For any of the applications described above, the secondary module may further include a flexible sheet, which (a) is blood-sealingly joined to a portion of the secondary border, which portion extends around at least 25% of a perimeter of the secondary border and includes a distal end of the secondary border when the secondary module is unconstrained in the radially-expanded state thereof, and (b) extends radially inward from the secondary border when the secondary module is unconstrained in the radially-expanded state thereof. For some applications, a portion of the secondary structural stent elements are attached to the flexible sheet.

For any of the applications described above:
the main-module lateral fenestration may be an inferior first lateral fenestration, which faces in a first radial direction,
when the main stent-graft is unconstrained in the radially-expanded state, the main covering element and the main support element may be shaped so as to together define a superior second lateral fenestration, which faces in a second radial direction generally opposite the first radial direction,
the stent-graft system may further include a generally tubular tertiary stent-graft, and
the main and the tertiary stent-grafts may be configured such that the tertiary stent-graft forms a blood-impervious seal with the main stent-graft around the superior second lateral fenestration when the tertiary stent-graft is disposed therethrough, and the main stent-graft is in the radially-expanded state thereof and the tertiary stent-graft is in a radially-expanded state thereof.

There is yet additionally provided, in accordance with an application of the present invention; apparatus including a stent-graft system, which includes:
a main module, which has distal and proximal main-module ends, and includes a generally tubular main stent-graft, which includes (a) a main generally tubular support element, which includes main structural stent elements, and (b) a main covering element that is attached to and at least partially covers the support element, wherein the main covering element and the main support element are shaped so as to together define a main-module lateral fenestration when the main module is unconstrained in a radially-expanded state thereof; and
a secondary module, which includes a non-bifurcated secondary stent-graft, which includes (a) a secondary support element, which includes secondary structural stent elements, (b) a secondary covering element that is attached to and at least partially covers the secondary support element, and (c) a flexible sheet,
wherein when the secondary module is unconstrained in a radially-expanded state thereof:
the secondary module is shaped so as to define (a) a proximal secondary-module end, (b) a sealing interface distal to the proximal secondary-module end, and (c) a central longitudinal axis therebetween, wherein the sealing interface is sized and configured to form a blood-impervious seal with the main-module lateral fenestration of the main module,
the secondary covering element is shaped so as to define at least one secondary-module lateral fenestration disposed distal to the proximal secondary-module end and proximal to the sealing interface, and
the flexible sheet (a) is blood-sealingly joined to a portion of a secondary border of the secondary-module lateral fenestration, which portion extends around at least 25% of a perimeter of the secondary border and includes a distal end of the secondary border when the secondary module is unconstrained in the radially-expanded state thereof, and (b) extends radially inward from the secondary border when the secondary module is unconstrained in the radially-expanded state thereof.

For some applications, a portion of the secondary structural stent elements are attached to the flexible sheet.

For some applications:
the main-module lateral fenestration is an inferior first lateral fenestration, which faces in a first radial direction,
when the main stent-graft is unconstrained in the radially-expanded state, the main covering element and the main support element are shaped so as to together define a superior second lateral fenestration, which faces in a second radial direction generally opposite the first radial direction,
the stent-graft system further includes a generally tubular tertiary stent-graft, and
the main and the tertiary stent-grafts are configured such that the tertiary stent-graft forms a blood-impervious seal with the main stent-graft around the superior second lateral fenestration when the tertiary stent-graft is disposed therethrough, and the main stent-graft is in the radially-expanded state thereof and the tertiary stent-graft is in a radially-expanded state thereof.

There is also provided, in accordance with an application of the present invention, apparatus including a stent-graft system, which includes:
a main module, which has distal and proximal main-module ends, and includes a generally tubular main stent-graft, which includes (a) a main generally tubular support element, which includes main structural stent elements, and (b) a main covering element that is attached to and at least partially covers the support element, wherein the main covering element and the main support element are shaped so as to together define a lateral fenestration when the main module is unconstrained in a radially-expanded state thereof; and
a secondary module, which includes a non-bifurcated secondary stent-graft, which includes (a) a secondary support element, which includes secondary structural stent elements, and (b) a secondary covering element that is attached to and partially covers the secondary support element,
wherein when the secondary module is unconstrained in a radially-expanded state thereof:
the secondary module is shaped so as to define (a) a proximal secondary-module end, (b) a sealing interface distal to the proximal secondary-module end, and (c) an anchoring axial portion therebetween having a central longitudinal axis and an anchoring-portion length, measured along the central longitudinal axis from the distal sealing interface to the proximal secondary-module end,
the sealing interface is sized and configured to form a blood-impervious seal with the lateral fenestration of the main module,
the secondary covering element at least covers the secondary support element along a covered axial portion of the anchoring axial portion, which covered axial portion extends proximally from the distal sealing interface for an axial covering distance equal to between 10% and 50% of the anchoring-portion length, the axial covering distance measured along the central longitudinal axis, wherein the secondary support element is uncovered proximally to the secondary covering element, and
the anchoring axial portion has a greatest anchoring-portion width that is (a) greater than a greatest proximal-end width at the proximal secondary-module end and (b) at least 20% greater than a greatest sealing-interface width at a narrowest portion of the distal sealing interface, the greatest anchoring-portion, sealing-interface, and proximal-end widths measured perpendicular to the central longitudinal axis.

For some applications, the anchoring axial portion has the greatest anchoring-portion width at an axial location at an axial distance from the proximal secondary-module end equal to between 33% and 60% of the anchoring-portion length, the axial distance measured along the central longitudinal axis, when the secondary module is unconstrained in the radially-expanded state thereof.

For some applications, the greatest anchoring-portion width is at least 50% greater than the greatest sealing-interface width at the narrowest portion of the distal sealing interface, when the secondary module is unconstrained in the radially-expanded state thereof.

For some applications, the axial covering distance from the distal sealing interface is equal to between 20% and 100% of an axial distance between the distal sealing interface and an axial location of the greatest anchoring-portion width, the axial distance measured along the central longitudinal axis, when the secondary module is unconstrained in the radially-expanded state thereof. For some applications, the axial covering distance from the distal sealing interface is equal to between 30% and 60% of the axial distance between the distal sealing interface and the axial location of the greatest anchoring-portion width, when the secondary module is unconstrained in the radially-expanded state thereof.

For some applications, the axial covering distance equals between 10% and 35% of the anchoring-portion length, when the secondary module is unconstrained in the radially-expanded state thereof.

For some applications, the axial covering distance is at least 15% of the anchoring-portion length, when the secondary module is unconstrained in the radially-expanded state thereof.

For any of the applications described above, the anchoring axial portion may include a plurality of the secondary structural stent elements, each of which has two longitudinal portions that extend toward the distal sealing interface, and an intermediary longitudinal portion that curves around the proximal secondary-module end, when the secondary module is unconstrained in the radially-expanded state thereof.

For any of the applications described above, the anchoring axial portion may include a plurality of the secondary structural stent elements, some of which touch one another, and none of which are fixed to one another, when the secondary module is unconstrained in the radially-expanded state thereof.

For any of the applications described above, an uncovered axial portion of the anchoring portion may extend from the proximal secondary-module end to a proximal end of the covered axial portion, for an axial uncovered distance equal to between 30 and 120 mm, when the secondary module is unconstrained in the radially-expanded state thereof.

For any of the applications described above, the greatest proximal-end width may equal zero.

There is further provided, in accordance with an application of the present invention, a method for treating a patient including:

endovascularly introducing a generally tubular stent-graft, while in a radially-compressed state, and positioning the stent-graft such that (a) a proximal stent-graft end of the stent-graft is positioned in a branch of an aortic arch selected from the group consisting of: a left subclavian artery left subclavian artery, and a left common carotid artery, and (b) a distal stent-graft end of the stent-graft is positioned in a descending aorta, wherein the stent-graft includes (a) a generally tubular support element, which includes a plurality of structural stent elements, and (b) a covering element that is attached to and at least partially covers the support element; and thereafter, transitioning the stent-graft to a radially-expanded state, in which (a) the covering element and the support element are shaped so as to together define a lateral fenestration that is disposed in the aortic arch, with the lateral fenestration facing upstream generally toward an ascending aorta, the lateral fenestration having distal and proximal fenestration ends, (b) a first perimeter of a distal stent-graft end of the stent-graft equals at least 200% of a second perimeter of the proximal stent-graft end, and (c) the stent-graft includes a dissection-reinforcement axial portion, which (i) includes a portion of the structural stent elements, (ii) has (x) a distal dissection-reinforcement end and (y) a proximal dissection-reinforcement end that is disposed along the stent-graft no more than 20 mm proximal to the proximal fenestration end, (iii) extends along the stent-graft for an axial distance equal to between 5% and 32% of a greatest perimeter of the stent-graft distally to the distal fenestration end, and (iv) has a radial strength that is at least 10% greater than an average radial strength of the entire stent-graft.

For some applications:

the lateral fenestration is an inferior first lateral fenestration, which faces in a first radial direction, when the main stent-graft is in the radially-expanded state, the main covering element and the main support element are shaped so as to together define a superior second lateral fenestration, which faces in a second radial direction generally opposite the first radial direction, and positioning the stent-graft includes positioning the stent-graft such that (a) the proximal stent-graft end is positioned in the left common carotid artery, (b) the inferior first lateral fenestration is disposed in the aortic arch, with the inferior first lateral fenestration facing upstream generally toward the ascending aorta, and (c) the superior second lateral fenestration is axially aligned with and faces the left subclavian artery.

There is still further provided, in accordance with an application of the present invention, a method for treating a patient including:

endovascularly introducing a generally tubular stent-graft, while in a radially-compressed state, and positioning the stent-graft such that (a) a proximal stent-graft end of the stent-graft is positioned in a branch of an aortic arch selected from the group consisting of: a left subclavian artery left subclavian artery, and a left common carotid artery, and (b) a distal stent-graft end of the stent-graft is positioned in a descending aorta, wherein the stent-graft includes (a) a generally tubular support element, which includes a plurality of structural stent elements arranged as a plurality circumferential stent springs, and (b) a covering element that is attached to and at least partially covers the support element; and thereafter, transitioning the stent-graft to a radially-expanded state, in which (a) the covering element and the support element are shaped so as to together define a lateral fenestration that is disposed in the aortic arch, with the lateral fenestration facing upstream generally toward an ascending aorta, the lateral fenestration having distal and proximal fenestration ends, (b) a first perimeter of a distal stent-graft end of the stent-graft equals at least 200% of a second perimeter of the proximal stent-graft end, (c) the stent-graft includes a dissection-reinforcement axial portion, which (i) includes a first plurality of the stent springs, (ii) has (x) a distal dissection-reinforcement end and (y) a proximal dissection-reinforcement end that is disposed along the stent-graft no more than 20 mm proximal to the proximal fenestration end, (iii) extends along the stent-graft for a distance equal to between 5% and 32% of a greatest perimeter of the stent-graft distally to the distal fenestration end, and (iv) is configured to be generally straight when the stent-graft is unconstrained in the radially-constrained state, (d) the stent-graft includes a distal axial portion, which (i) includes a second plurality of the stent springs, (ii) is disposed along the stent-graft distal and axially adjacent to the distal dissection-reinforcement end, (iii) extends along the stent-graft for a distance equal to between 5% and 32% of the greatest perimeter of the stent-graft distally to the distal fenestration end, (e) the stent springs have respective average heights, measured axially along the stent-graft, and (f) an average of the average heights of the first plurality of the stent springs is less than 75% of the average height of a proximal-most one of the second plurality of the stent springs.

For some applications:
the lateral fenestration is an inferior first lateral fenestration, which faces in a first radial direction,
when the main stent-graft is in the radially-expanded state, the main covering element and the main support element are shaped so as to together define a superior second lateral fenestration, which faces in a second radial direction generally opposite the first radial direction, and
positioning the stent-graft includes positioning the stent-graft such that (a) the proximal stent-graft end is positioned in the left common carotid artery, (b) the inferior first lateral fenestration is disposed in the aortic arch, with the inferior first lateral fenestration facing upstream generally toward the ascending aorta, and (c) the superior second lateral fenestration is axially aligned with and faces the left subclavian artery.

There is additionally provided, in accordance with an application of the present invention, a method for treating a patient including:
endovascularly introducing a main module, while in a radially-compressed state thereof, and positioning the main module such that (a) a proximal main-module end of the main module is positioned in a branch of an aortic arch selected from the group consisting of: a left subclavian artery left subclavian artery, and a left common carotid artery, and (b) a distal main-module end of the main module is positioned in a descending aorta, wherein the main module includes a generally tubular main stent-graft, which includes (a) a main generally tubular support element, which includes main structural stent elements, and (b) a main covering element that is attached to and at least partially covers the support element;
thereafter, transitioning the main stent-graft to a radially-expanded state thereof, in which the main covering element and the main support element are shaped so as to together define a lateral fenestration that is disposed in the aortic arch, with the lateral fenestration facing upstream generally toward an ascending aorta;
endovascularly introducing and passing a secondary module, while in a radially-compressed state thereof, through a distal portion of the main stent-graft such that the secondary module is disposed through the lateral fenestration and is disposed partially in the aortic arch, wherein the secondary module includes a non-bifurcated secondary stent-graft, which includes (a) a secondary support element, which includes secondary structural stent elements, and (b) a secondary covering element that is attached to and at least partially covers the secondary support element; and
thereafter, transitioning the secondary module to a radially-expanded state thereof, in which the secondary module is shaped so as to define (a) a proximal secondary-module end, (b) a sealing interface distal to the proximal secondary-module end, and (c) a central longitudinal axis therebetween, such that the sealing interface forms a blood-impervious seal with the lateral fenestration of the main module, and the secondary covering element is shaped so as to define at least one lateral opening that begins at and extends from the proximal secondary-module end toward the sealing interface along the central longitudinal axis for a distance equal to at least 50% of a greatest width of the secondary module, measured perpendicular to the central longitudinal axis.

For some applications:
the lateral fenestration is an inferior first lateral fenestration, which faces in a first radial direction,
when the main stent-graft is in the radially-expanded state, the main covering element and the main support element are shaped so as to together define a superior second lateral fenestration, which faces in a second radial direction generally opposite the first radial direction, and
positioning the stent-graft includes positioning the stent-graft such that (a) the proximal stent-graft end is positioned in the left common carotid artery, (b) the inferior first lateral fenestration is disposed in the aortic arch, with the inferior first lateral fenestration facing upstream generally toward the ascending aorta, and (c) the superior second lateral fenestration is axially aligned with and faces the left subclavian artery.

There is yet additionally provided, in accordance with an application of the present invention, a method for treating a patient including:
endovascularly introducing a main module, while in a radially-compressed state thereof, and positioning the main module such that (a) a proximal main-module end of the main module is positioned in a branch of an aortic arch selected from the group consisting of: a left subclavian artery left subclavian artery, and a left common carotid artery, and (b) a distal main-module end of the main module is positioned in a descending aorta, wherein the main module includes a generally tubular main stent-graft, which includes (a) a main generally tubular support element, which includes main structural stent elements, and (b) a main covering element that is attached to and at least partially covers the support element;
thereafter, transitioning the main stent-graft to a radially-expanded state thereof, in which the main covering element and the main support element are shaped so as to together define a main-module lateral fenestration that is disposed in the aortic arch, with the main-module lateral fenestration facing upstream generally toward an ascending aorta;
endovascularly introducing and passing a secondary module, while in a radially-compressed state thereof, through a distal portion of the main stent-graft such that the secondary module is disposed through the main-module lateral fenestration and is disposed partially in the aortic arch, wherein the secondary module includes a non-bifurcated secondary stent-graft, which includes (a) a secondary support element, which includes secondary structural stent elements, and (b) a secondary covering element that is attached to and at least partially covers the secondary support element; and
thereafter, transitioning the secondary module to a radially-expanded state thereof, in which the secondary module is shaped so as to define (a) a proximal secondary-module end, (b) a sealing interface distal to the proximal secondary-module end, and (c) a central longitudinal axis therebetween, such that the sealing interface forms a blood-impervious seal with the main-module lateral fenestration of the main module, and the secondary covering element is shaped so as to define at least one secondary-module lateral fenestration disposed distal to the proximal secondary-module end and proximal to the sealing interface, wherein a greatest axial length of the secondary-module lateral fenestration, measured parallel to the central longitudinal axis, equals at least 33% of a first perimeter of the distal main-module end.

There is also provided, in accordance with an application of the present invention, a method for treating a patient including:

endovascularly introducing a main module, while in a radially-compressed state thereof, and positioning the main module such that (a) a proximal main-module end of the main module is positioned in a branch of an aortic arch selected from the group consisting of: a left subclavian artery left subclavian artery, and a left common carotid artery, and (b) a distal main-module end of the main module is positioned in a descending aorta, wherein the main module includes a generally tubular main stent-graft, which includes (a) a main generally tubular support element, which includes main structural stent elements, and (b) a main covering element that is attached to and at least partially covers the support element;

thereafter, transitioning the main stent-graft to a radially-expanded state thereof, in which the main covering element and the main support element are shaped so as to together define a main-module lateral fenestration that is disposed in the aortic arch, with the main-module lateral fenestration facing upstream generally toward an ascending aorta;

endovascularly introducing and passing a secondary module, while in a radially-compressed state thereof, through a distal portion of the main stent-graft such that the secondary module is disposed through the main-module lateral fenestration and is disposed partially in the aortic arch, wherein the secondary module includes a non-bifurcated secondary stent-graft, which includes (a) a secondary support element, which includes secondary structural stent elements, (b) a secondary covering element that is attached to and at least partially covers the secondary support element, and (c) a flexible sheet; and thereafter, transitioning the secondary module to a radially-expanded state thereof, in which (a) the secondary module is shaped so as to define (a) a proximal secondary-module end, (b) a sealing interface distal to the proximal secondary-module end, and (c) a central longitudinal axis therebetween, such that the sealing interface forms a blood-impervious seal with the main-module lateral fenestration of the main module, (b) the secondary covering element is shaped so as to define at least one secondary-module lateral fenestration disposed distal to the proximal secondary-module end and proximal to the sealing interface, and (c) the flexible sheet (i) is blood-sealingly joined to a portion of a secondary border of the secondary-module lateral fenestration, which portion extends around at least 25% of a perimeter of the secondary border and includes a distal end of the secondary border, and (ii) extends radially inward from the secondary border when the secondary module is unconstrained in the radially-expanded state thereof.

There is further provided, in accordance with an application of the present invention, a method for treating a patient including:

endovascularly introducing a main module, while in a radially-compressed state thereof, and positioning the main module such that (a) a proximal main-module end of the main module is positioned in a branch of an aortic arch selected from the group consisting of: a left subclavian artery left subclavian artery, and a left common carotid artery, and (b) a distal main-module end of the main module is positioned in a descending aorta, wherein the main module includes a generally tubular main stent-graft, which includes (a) a main generally tubular support element, which includes main structural stent elements, and (b) a main covering element that is attached to and at least partially covers the support element;

thereafter, transitioning the main stent-graft to a radially-expanded state thereof, in which the main covering element and the main support element are shaped so as to together define a lateral fenestration that is disposed in the aortic arch, with the lateral fenestration facing upstream generally toward an ascending aorta;

endovascularly introducing and passing a secondary module, while in a radially-compressed state thereof, through a distal portion of the main stent-graft such that the secondary module is disposed through the lateral fenestration and is disposed partially in the aortic arch, wherein the secondary module includes a non-bifurcated secondary stent-graft, which includes (a) a secondary support element, which includes secondary structural stent elements, and (b) a secondary covering element that is attached to and partially covers the secondary support element; and thereafter, transitioning the secondary module to a radially-expanded state thereof, in which the secondary module is shaped so as to define (a) a proximal secondary-module end, (b) a sealing interface distal to the proximal secondary-module end, and (c) an anchoring axial portion therebetween having a central longitudinal axis and an anchoring-portion length, measured along the central longitudinal axis from the distal sealing interface to the proximal secondary-module end, such that the sealing interface forms a blood-impervious seal with the lateral fenestration of the main module, the secondary covering element at least covers the secondary support element along a covered axial portion of the anchoring axial portion, which covered axial portion extends proximally from the distal sealing interface for an axial covering distance equal to between 10% and 50% of the anchoring-portion length, the axial covering distance measured along the central longitudinal axis, wherein the secondary support element is uncovered proximally to the secondary covering element, and the anchoring axial portion has a greatest anchoring-portion width that is (a) greater than a greatest proximal-end width at the proximal secondary-module end and (b) at least 20% greater than a greatest sealing-interface width at a narrowest portion of the distal sealing interface, the greatest anchoring-portion, sealing-interface, and proximal-end widths measured perpendicular to the central longitudinal axis.

The present invention will be more fully understood from the following detailed description of embodiments thereof, taken together with the drawings, in which:

BRIEF DESCRIPTION OF THE DRAWINGS

FIG. 1 is a schematic illustration of multi-component stent-graft system, in accordance with an application of the present invention;

FIGS. 2A-B are schematic illustrations of a main module of the multi-component stent-graft system of FIG. 1, in accordance with respective applications of the present invention;

FIG. 3 is a schematic illustration of a secondary module of the multi-component stent-graft system of FIG. 1, in accordance with an application of the present invention;

FIG. 4 is a schematic illustration of another configuration of the secondary module of the multi-component stent-graft system of FIG. 1, in accordance with an application of the present invention;

FIGS. 5 and 6 are schematic illustrations of alternative configurations of the secondary module of the multi-component stent-graft system of FIG. 1, in accordance with respective applications of the present invention;

FIGS. 14A-B are schematic illustrations of kinking properties of different axial portions of a main stent-graft of the multi-component stent-graft system of FIG. 1, in accordance with an application of the present invention; and FIG. 15 is a schematic illustration of kinking in a stent-graft.

DETAILED DESCRIPTION OF APPLICATIONS

Figure 7:
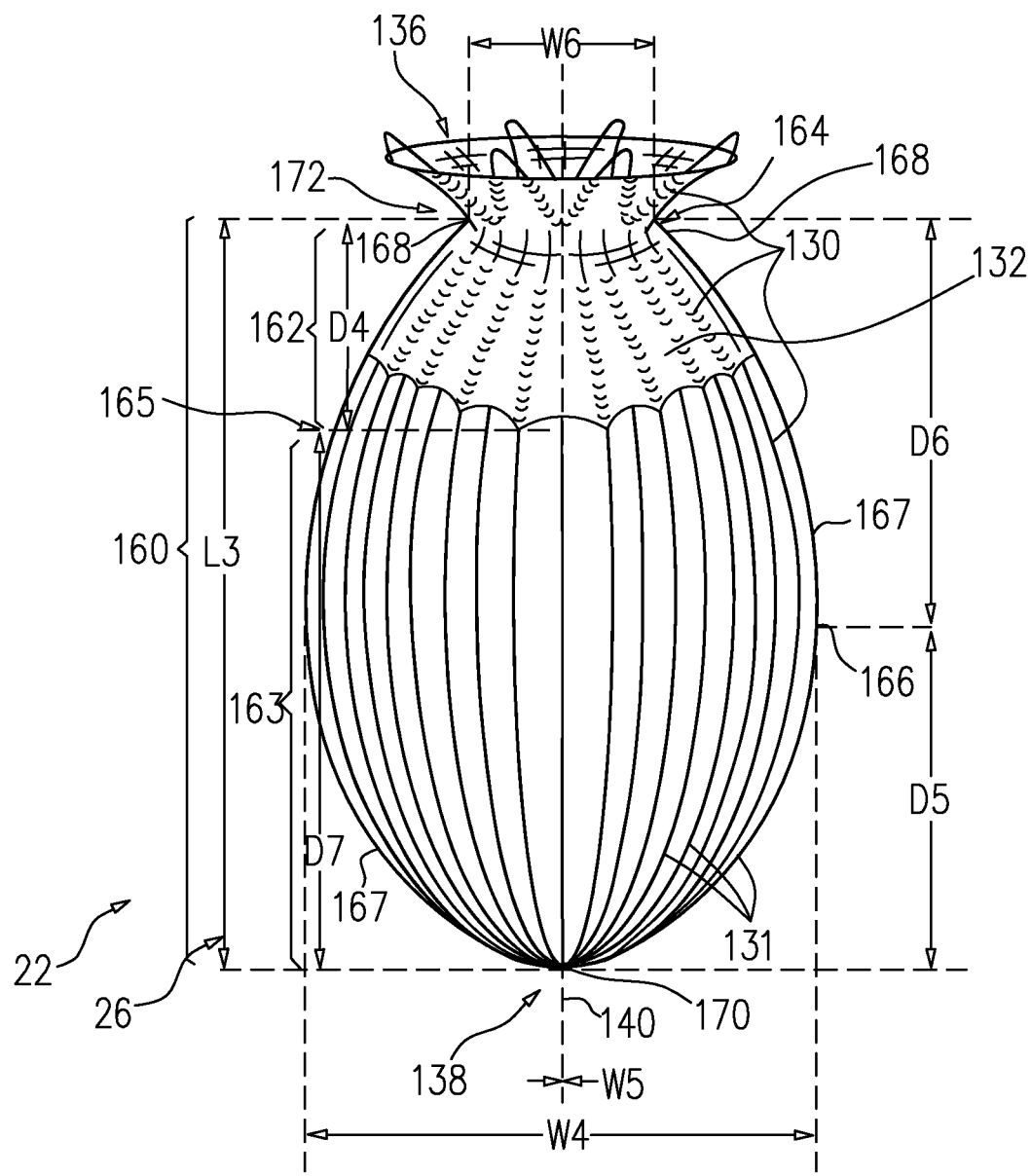
FIG. 7 is a schematic illustration of yet another configuration of the secondary module of the secondary module of the multi-component stent-graft system of FIG. 1, in accordance with an application of the present invention.

FIG. 1 is a schematic illustration of multi-component stent-graft system 10, in accordance with an application of the present invention. In some applications of the present invention, multi-component stent-graft system 10 is provided for treating a Type B aortic dissection 12. The system is configured to be deployed in a thoracic aorta 14 and a left subclavian artery 16, and, optionally, a left common carotid artery 18. The multi-component stent-graft system is configured to be deployed in a straightforward procedure. The stent-grafts of the system are assembled in situ to accommodate the dimensions of the particular patient's anatomy, generally without requiring prior customization of the stent-grafts or in situ modifications to the stent-grafts, which might be expensive and/or complex.

Typically, upon deployment, the multi-component stent-graft system defines a blood-flow path from an ascending aorta 17, over an aortic arch 19, and to the descending aorta. The multi-component stent-graft system additionally provides or allows blood-flow paths to the three branches of the aortic arch.

Multi-component stent-graft system 10 comprises a main module 20 and, for some applications, a secondary module 22. Main module 20 comprises a generally tubular main stent-graft 24, and secondary module 22 comprises a non-bifurcated secondary stent-graft 26. The stent-grafts are configured to assume radially-compressed states, such as when initially positioned in one or more outer tubes of one or more delivery tools, and to assume radially-expanded states upon being deployed from the outer tube(s). FIG. 1 shows the stent-grafts in their radially-expanded states in situ. For some applications, the stent-grafts are relaxed in their radially-expanded states. For some applications, the stent-grafts are configured to be self-expanding. For example, they may be heat-set to assume their radially-expanded states.

Exemplary Configuration of the Main Module

Reference is still made to FIG. 1, and is additionally made to FIGS. 2A-B, which are schematic illustrations of main module 20 that comprises main stent-graft 24, in accordance with respective applications of the present invention. FIGS. 2A-B show main stent-graft 24 unconstrained in its radially-expanded state, i.e., no forces are applied to the stent-graft by a delivery tool, walls of a blood vessel, or otherwise. Main stent-graft 24 typically comprises a main generally tubular support element 30 and a main covering element 32 that is attached to and at least partially covers (e.g., only partially covers) the main support element. Support element 30 typically comprises a plurality of main structural stent elements 31. For some applications, main structural stent elements 31 are arranged as a plurality of circumferential stent springs 33. For some applications, support element 30, as well as support elements 130, 230 and 330, which are described hereinbelow, comprise a super-elastic alloy, such as Nitinol. Main covering element 32 serves as a blood flow guide through at least a portion of the main stent-graft. Main covering element 32 typically comprises at least one biologically-compatible substantially blood-impervious flexible sheet, which is attached (such as by stitching) to at least a portion of the respective support element, on either side of the surfaces defined by the support element. The flexible sheet may comprise, for example, a polymeric material (e.g., a polyester, or polytetrafluoroethylene), a textile material (e.g., polyethylene terephthalate (PET)), natural tissue (e.g., saphenous vein or collagen), or a combination thereof.

Main covering element 32 and main support element 30 are shaped so as to together define a lateral fenestration 34, e.g., exactly one lateral fenestration 34, through main stent-graft 24, which lateral fenestration has distal and proximal fenestration ends 35 and 37, when main stent-graft 24 is unconstrained in its radially-expanded state. As used in the present application, including in the claims, a "fenestration" is an opening entirely surrounded by a covering element. For example, lateral opening 174, described hereinbelow with reference to FIG. 3, is not a fenestration, because the lateral opening extends from the end of module and thus is not surrounded by the covering element along a proximal edge of the lateral opening. When multi-component stent-graft system 10 is implanted as shown in FIG. 1, lateral fenestration 34 serves as an inferior lateral fenestration. Typically, at least a portion of the border of lateral fenestration 34 is defined by an undulating portion of one or more of structural stent elements 31.

For some applications, when main stent-graft 24 is unconstrained in its radially-expanded state, i.e., no forces are applied to the stent-graft by a delivery tool, walls of a blood vessel, or otherwise, a first perimeter P1 of a distal main-module end 36 of main stent-graft 24 (and main module 20) is greater than a second perimeter P2 of a proximal main-module end 38 of the main stent-graft (and the main module), and/or a first cross-sectional area of the distal main-module end 36 is greater than a second cross-sectional area of proximal main-module end 38. For applications in which main stent-graft 24 is generally cylindrical when unconstrained in its radially-expanded state, first and second perimeters P1 and P2 are first and second diameters. For example, first perimeter P1 may equal at least 150% of second perimeter P2, such as at least 200%, at least 250%, at least 300%, or at least 400%, and/or the first cross-sectional area may equal at least 225% of the second cross-sectional area, such as at least 400%, at least 625%, at least 900%, or at least 1600%.

For example, first perimeter P1 may be at least 5 cm, no more than 15 cm, and/or between 5 and 15 cm, such as at least 7.5 cm, e.g., at least 9 cm, no more than 13 cm, and/or between 7.5 (e.g., 9) and 13 cm, and second perimeter P2 may be at least 2.5 cm, no more than 5.7 cm, and/or between 2.5 and 5.7 cm, such as at least 3 cm, no more than 4.5 cm, and/or between 3 and 4.5 cm.

For some applications, when main stent-graft 24 is unconstrained in its radially-expanded state, a perimeter of lateral fenestration 34 is at least 5 cm, no more than 15 cm, and/or between 5 and 15 cm, such as at least 7.5 cm, e.g., at least 9 cm, no more than 13 cm, and/or between 7.5 cm (e.g., 9 cm) and 13 cm. For some applications, when main stent-graft 24 is unconstrained in its radially-expanded state, a perimeter of lateral fenestration 34 is at least 80%, no more than 120%, and/or between 80% and 120% of first perimeter P1, and/or at least 150%, no more than 250%, and/or between 150% and 250% of second perimeter P2.

For some applications, secondary module 22 is not necessary for providing blood flow into the lateral fenestration, and is thus optionally not provided. For example, secondary module 22 may not be necessary when lateral fenestration 34 is sufficiently large (e.g., has a perimeter of at least 9 cm and/or at least 80% of first perimeter P1).

For some applications, main stent-graft 24, when unconstrained in its radially-expanded state, has an axial length of at least 5 cm, no more than 40 cm, and/or between 5 and 30 cm, such as at least 10 cm, no more than 30 cm, and/or between 10 and 30 cm. (The axial length is measured along a central longitudinal axis 40 of the stent-graft.) For some applications, main stent-graft 24, when unconstrained in its radially-expanded state, has a greatest perimeter (at any axial location along the stent-graft) of at least 7.5 cm, no more than 19 cm, and/or between 7.5 and 19 cm, such as at least 12.5 cm, no more than 16 cm, and/or between 12.5 and 16 cm. These values are typical for adult subjects, in which the vast majority of dissections occur. For pediatric subjects, in which dissections are rare, these dimensions may be reduced by a factor of up to 1:3.

For some applications, such dimensions allow main stent-graft 24 to be positioned such that (a) a distal, radially larger, descending-aorta axial portion 42 of the stent-graft, including distal main-module end 36 thereof, is disposed in the aorta downstream from the bifurcation with the left subclavian artery, at least partially in the upper part of the descending aorta, (b) a proximal, radially smaller, supra-arch axial portion 44 of the main stent-graft, including proximal main-module end 38 thereof, is disposed in left subclavian artery 16, as shown in FIG. 1, and (c) an arch axial portion 46, axially between descending-aorta axial portion 42 and supra-arch axial portion 44, is disposed in aortic arch 19. Typically, arch axial portion 46 at least partially axially overlaps fenestration 34, since the fenestration should be disposed in the apex of the arch. For some applications, descending-aorta axial portion 42 has an average perimeter that is greater than (e.g., between 5% and 15% greater than) an average perimeter of the portion of the aorta in which it is disposed. For some applications, supra-arch axial portion 44 has an average perimeter that is greater than (e.g., between 5% and 15% greater than) the average perimeter of the portion of the left subclavian artery in which it is disposed.

For some applications, when main stent-graft 24 is unconstrained in its radially-expanded state, the main stent-graft includes a dissection-reinforcement axial portion 48, which:
  includes a portion of main structural stent elements 31;
  has a distal dissection-reinforcement end 50;
  has a proximal dissection-reinforcement end 52 that is disposed along the stent-graft no more than 20 mm proximal to proximal fenestration end 37; proximal dissection-reinforcement end 52 may be either proximal or distal to proximal fenestration end 37. For some applications, proximal dissection-reinforcement end 52 is disposed along the main stent-graft no more proximal than distal fenestration end 35 when the stent-graft is unconstrained in the radially-expanded state, such as shown in FIGS. 1 and 2A. For other applications, proximal dissection-reinforcement end 52 is disposed along the main stent-graft between distal fenestration end 35 and proximal fenestration end 37, inclusive, when the stent-graft is unconstrained in the radially-expanded state, such as shown in FIG. 2B; and/or
  extends along the stent-graft for a distance equal to at least 5%, no more than 32%, and/or between 5% and 32% of a greatest perimeter of the stent-graft distally to distal fenestration end 35, such as at least 10%, no more than 20%, and/or between 10% and 20%.

For some applications, dissection-reinforcement axial portion 48 has a radial strength that is at least 10% greater than an average radial strength of the entire main stent-graft, such as at least 15% greater, or at least 30% greater. This greater strength increases the force that dissection-reinforcement axial portion 48 applies to a tear 56 of aortic dissection 12, thereby sealing the tear. Tear 56 is generally located in an upper portion of thoracic aorta 14, and sometimes additionally in a lower portion of left subclavian artery 16 and/or at the take-off of left subclavian artery 16 from thoracic aorta 14. (It is noted that providing the entire length of the main stent-graft with a high strength has at least two drawbacks: stent-grafts with higher strengths are more difficult to deploy, and are more likely to cause damage to the vasculature.)

Typically, an arch axial portion 46 and dissection-reinforcement axial portion 48 do not include any bare main structural stent elements 31, such that main covering element 32 intervenes between the stent elements and the blood vessel wall in the vicinity of tear 56.

For some applications, an axial length of dissection-reinforcement axial portion 48 is at least 1 cm, no more than 3 cm, and/or between 1 and 3 cm when the main stent-graft is unconstrained in the radially-expanded state.

For some applications, a distance D1 between distal dissection-reinforcement end 50 and distal main-module end 36 is at least 32%, no more than 160%, and/or between 32% and 160% of a largest perimeter of the main stent-graft, when the main stent-graft is unconstrained in the radially-expanded state. Alternatively or additionally, for some applications, distance D1 is at least 3 cm, no more than 5 cm, and/or between 3 and 5 cm, when the main stent-graft is unconstrained in the radially-expanded state. Still further alternatively or additionally, for some applications, when the main stent-graft is unconstrained in the radially-expanded state: (a) distance D1 equals between at least 20%, no more than 66%, and/or between 20% and 66% of a total length L1 of main stent-graft 24, and/or (b) a distance D2 between proximal dissection-reinforcement end 52 and proximal main-module end 38 equals at least 33%, no more than 80%, and/or between 33% and 80% of total length L1.

For some applications, such as shown in FIGS. 2A-B, dissection-reinforcement axial portion 48 is configured to be generally straight when the main stent-graft is unconstrained in the radially-expanded state.

For some applications, main structural stent elements 31 of dissection-reinforcement axial portion 48 are arranged as a plurality of circumferential stent springs 33 of dissection-reinforcement axial portion 48. For some applications, a strut height H, measured axially along the main stent-graft, of at least one of stent springs 33 of dissection-reinforcement axial portion 48 varies by less than 10% around a circumference of the stent spring when the main stent-graft is unconstrained in the radially-expanded state. For some applications, for each one of stent springs 33 of dissection-reinforcement axial portion 48, height H of the stent spring varies by less than 10% around a circumference of the stent spring when the main stent-graft is unconstrained in the radially-expanded state.

For some applications, the portion of structural stent elements 31 included by dissection-reinforcement axial portion 48 is a first portion of structural stent elements 31, and when the stent-graft is unconstrained in the radially-expanded state: (a) main stent-graft 24 includes a distal-end axial portion 54, which includes a second portion of structural stent elements 31, (b) distal-end axial portion 54 axially extends along the stent-graft from distal main-module end 36 for a distance equal to at least 5%, no more than 32%, and/or between 5% and 32% of a greatest perimeter of the main stent-graft distally to distal fenestration end 35, such as at least 11%, no more than 22%, and/or between 11% and 22%, and (c) distal-end axial portion 54 has a radial strength that is at least a 10% greater than the average radial strength of the entire main stent-graft.

For some applications, dissection-reinforcement axial portion 48 includes a first plurality 60 of stent springs 33, and main stent-graft 24 includes a distal axial portion 58, which includes a second plurality 62 of stent springs 33. Distal axial portion 58 is disposed along the main stent-graft distal and axially adjacent to distal dissection-reinforcement end 50, and extends along the main stent-graft for a distance equal to at least 5%, no more than 32%, and/or between 5% and 32% of the greatest perimeter of the main stent-graft distally to the distal fenestration end 35. Typically, distal axial portion 58 extends to and reaches the distal main-module end 36. Stent springs 33 have respective average strut heights, measured axially along the main stent-graft (the height of each stent spring is averaged circumferentially around the stent-graft). An average of the average heights of first plurality 60 of stent springs 33 is less than 75% (e.g., less than 70%) of the average height of a proximal-most one 64 of second plurality 62 of stent springs 33. These smaller average heights generally allow dissection-reinforcement axial portion 48 to bend without the stent springs thereof coming into contact with one another. For these applications, dissection-reinforcement axial portion 48 is typically configured to be generally straight when the main stent-graft is unconstrained in the radially-expanded state.

For some applications, each of the average heights of first plurality 60 of stent springs 33 is less than 75% (e.g., less than 70%) of the average height of proximal-most one 64 of second plurality 62 of stent springs 33 when the main stent-graft is unconstrained in the radially-expanded state. For some applications, the average of the average heights of first plurality 60 of stent springs 33 is less than 75% (e.g., less than 70%) of the average height of a second one 66 of second plurality 62 of stent springs 33, other than proximal-most one 64 of second plurality 62 of stent springs 33 when the main stent-graft is unconstrained in the radially-expanded state. For some applications, the average of the average heights of first plurality 60 of stent springs 33 is less than 75% (e.g., less than 70%) of each of the average heights of second plurality 62 of stent springs 33 when the main stent-graft is unconstrained in the radially-expanded state.

For some applications, an axial spacing S between two of first plurality 60 of stent springs 33 of dissection-reinforcement axial portion 48 equals less than 10% of an average of the average heights H of the two stent springs 33. Such low axial spacing between the stent springs of reduces the risk of kinking of dissection-reinforcement axial portion 48. The use of a greater axial spacing S would make dissection-reinforcement axial portion 48 more prone to kinking, such as described hereinbelow with reference to FIG. 14.

For some applications, distal axial portion 58 is configured to be generally straight when the main stent-graft is unconstrained in the radially-expanded state.

Exemplary Configuration of the Secondary Module

Reference is still made to FIG. 1, and is additionally made to FIG. 3, which is a schematic illustration of secondary module 22 that comprises secondary stent-graft 26, in accordance with an application of the present invention. FIG. 3 shows secondary stent-graft 26 unconstrained in its radially-expanded state, i.e., no forces are applied to the stent-graft by a delivery tool, walls of a blood vessel, or otherwise. Secondary stent-graft 26 typically comprises a secondary generally tubular support element 130 and a secondary covering element 132 that is attached to and at least partially covers (e.g., only partially covers) the secondary support element. Support element 130 typically comprises a plurality of secondary structural stent elements 131. For some applications, secondary structural stent elements 131 are arranged as a plurality of circumferential stent springs 133. Secondary covering element 132 serves as a blood flow guide through at least a portion of the secondary stent-graft. Secondary covering element 132 typically comprises at least one biologically-compatible substantially blood-impervious flexible sheet, which is attached (such as by stitching) to at least a portion of the respective support element, on either side of the surfaces defined by the support element. The flexible sheet may comprise, for example, a polymeric material (e.g., a polyester, or polytetrafluoroethylene), a textile material (e.g., polyethylene terephthalate (PET)), natural tissue (e.g., saphenous vein or collagen), or a combination thereof.

When secondary module 22 (and secondary stent-graft 26) is unconstrained in the radially-expanded state thereof:
secondary module 22 is shaped so as to define a proximal secondary-module end 138, a sealing interface 172 distal to proximal secondary-module end 138, and a central longitudinal axis 140 therebetween. Sealing interface 172 is sized and configured to form a blood-impervious seal with lateral fenestration 34 of main module 20;
secondary module 22 is shaped so as to define a distal secondary-module end 136; and
secondary covering element 132 is shaped so as to define at least one lateral opening 174 that begins at and extends from proximal secondary-module end 138 toward sealing interface 172 along central longitudinal axis 140 for a distance D3 equal to at least 50% (e.g., at least 70%) of a greatest width W1 of secondary module 22, measured perpendicular to central longitudinal axis 140. In other words, lateral opening 174 reaches proximal secondary-module end 138, is thus not entirely surrounded by secondary covering element 132, and therefore is not a fenestration, as defined hereinabove with reference to FIGS. 1 and 2A-B.

For some applications, a greatest width W2 of at least one lateral opening 174, measured circumferentially around secondary module 22, equals at least 90 degrees circumferentially around proximal secondary-module end 138, the 90 degrees being measured at sealing interface 172 (even though the lateral opening typically does not extend to the sealing interface, and may have its greatest width W2 at proximal secondary-module end 138).

For some applications, at least one of secondary structural stent elements 131 traverses lateral opening 174 when the secondary module is unconstrained in the radially-expanded state thereof. By way of example, in FIG. 3 two secondary structural stent elements 131B are shown traversing lateral opening 174. Alternatively, a single secondary structural stent element 131B, or three or more secondary structural stent elements 131B, traverse lateral opening 174. Such traversal may provide additional structural strength to secondary module 22 at the lateral opening. For some applications of this configuration, support element 130 is shaped so as to define a complete tube, which is only partially covered by secondary covering element 132. For some other applications in which none of secondary structural stent elements 131 traverses lateral opening 174, support element 130 is shaped so as to define a partial tube circumferentially.

For some applications, a cross-sectional area of secondary module 22, measured perpendicular to central longitudinal axis 40, gradually tapers from proximal secondary-module end 138 to sealing interface 172 when the secondary module is unconstrained in the radially-expanded state thereof.

For some applications, such as shown in FIG. 3, the at least one lateral opening 174 comprises exactly one lateral opening 174. For some of these applications, when secondary module 22 is unconstrained in the radially-expanded state thereof, lateral opening 174 faces in a first radial direction extending from central longitudinal axis 140, and a portion 176 of secondary covering element 132 that faces in a second radial direction opposite the first radial direction extends to and reaches proximal secondary-module end 138. In other words, secondary module 22 is covered by secondary covering element 132 on the side circumferentially opposite lateral opening 174, such that lateral opening 174 and portion 176 face in radially-opposite directions.

Typically, upon deployment of main and secondary modules 20 and 22, the stent-grafts together provide continuous coverage covering element material along the blood flow path, which may help prevent further trauma to aorta, and sub-tears in the aorta.

Exemplary Deployment of the Multi-Component Stent-Graft System

Reference is again made to FIG. 1, which schematically shows a portion of a typical aorta, including thoracic aorta 14, which includes an upper part of ascending aorta 17, and aortic arch 19, and an upper part of a supra-renal descending aorta. Also shown are the three branches of aortic arch 19: a brachiocephalic artery 70, left common carotid artery 18, and left subclavian artery 16.

In an exemplary transluminal delivery procedure for implanting multi-component stent-graft system 10, as configured in FIGS. 1 and 2A-B, the stent-grafts of system 10 are endovascularly (typically percutaneously) introduced into the thoracic aorta, such as via one of the iliac arteries, while the stent-grafts are positioned in one or more outer tubes of a delivery tool in their radially-compressed states.

Typically, the exemplary procedure begins with the advancing of a guidewire up the descending aorta and into left subclavian artery 16. Main stent-graft 24 of main module 20 is initially positioned in its radially-compressed state within an outer tube of a delivery tool, typically near a leading end of the outer tube. The outer tube is advanced over the guidewire, until main stent-graft 24 is partially disposed in left subclavian artery 16 and partially disposed in the upper part of the descending aorta. The guidewire is withdrawn, leaving the outer tube in place. The main stent-graft is held in place as the outer tube is withdrawn, thereby delivering the main stent-graft from the outer tube. Main stent-graft 24 typically self-expands, until it assumes its radially-expanded state, upon reaching typically about 80-90% of its maximum unconstrained size, and/or being constrained from further expansion by the wall of the blood vessels, as shown in FIG. 1. Alternatively, the main stent-graft (and/or the other stent-grafts, as described hereinbelow) is delivered using an over-the-wire (OTW) approach, in which the guidewire is left in place until the stent-graft is expanded, and thereafter the guidewire is withdrawn.

Descending-aorta axial portion 42 of main stent-graft 24, including distal main-module end 36, is positioned in the upper part of the descending aorta, and supra-arch axial portion 44 of main stent-graft 24, including proximal main-module end 38, is positioned in left subclavian artery 16. Arch axial portion 46 of main stent-graft 24, including lateral fenestration 34, is disposed in aortic arch 19, with the lateral fenestration facing upstream, generally toward ascending aorta 17, in a vicinity of the bifurcation of aortic arch 19 and left subclavian artery 16. For some applications, proper rotational alignment and/or axial orientation of the lateral fenestration is achieved using fluoroscopy. For example, main stent-graft 24 may comprise one or more radiopaque markers in a vicinity of (e.g., on a periphery of) the lateral fenestration.

A guidewire (either the same guidewire used to deploy the main stent-graft, or a second guidewire) is advanced up the descending aorta, through a distal portion of main stent-graft 24, out of lateral fenestration 34, and into aortic arch 19, extending toward, or partially into, ascending aorta 17. Secondary stent-graft 26 of secondary module 22 is positioned in its radially-compressed state within an outer tube of a delivery tool (either the same outer tube used to deploy the main stent-graft, or a second outer tube), typically near a leading end of the outer tube. The outer tube is advanced over the guidewire, until secondary stent-graft 26 is partially disposed in aortic arch 19, extending toward, or partially into, ascending aorta 17, and partially disposed within radially-expanded main stent-graft 24 in the upper part of the descending aorta. The guidewire is withdrawn, leaving the outer tube in place.

The secondary stent-graft is rotationally aligned such that the at least one lateral opening 174 faces left common carotid artery 18, so as to allow blood flow to the left common carotid artery (and, for applications in which the secondary stent-graft is long enough, so as to allow blood flow into brachiocephalic artery 70). The secondary stent-graft may comprise one or more radiopaque markers to facilitate such proper rotational alignment. For example, the radiopaque markers may be positioned on one or more edges of the at least one lateral opening. Secondary module 22 is positioned so as to not block brachiocephalic artery 70 or left common carotid artery 18.

The secondary stent-graft is held in place as the outer tube is withdrawn, thereby delivering the secondary stent-graft from the outer tube. Secondary stent-graft 26 typically self-expands, until it assumes its radially-expanded state, upon reaching its maximum unconstrained size, and/or being constrained from further expansion by the wall of the blood vessels. Secondary stent-graft 26 is thus adapted for transluminal delivery in its radially-compressed state through a portion of main stent-graft 24 and lateral fenestration 34, while the main stent-graft is in its radially-expanded state.

A distal portion of secondary stent-graft 26, including distal secondary-module end 136, is positioned within main stent-graft 24, and sealing interface 172 of secondary stent-graft 26 is sealingly coupled to lateral fenestration 34 of main stent-graft 24. A proximal portion of secondary stent-graft 26, including proximal secondary-module end 138, is positioned in aortic arch 19. As mentioned, the at least one lateral opening 174 faces left common carotid artery 18. Secondary module 22 reduces blood turbulence in the aortic arch, and serves as a funnel that creates a gradual taper of the blood flow into lateral fenestration 34 of main stent-graft 24.

For some applications, main and secondary stent-grafts 24 and 26, when in their respective radially-expanded states, constrained by the respective blood vessels in which they are positioned, have some or all of the dimensional and/or strength characteristics described herein as applicable when the stent-grafts are unconstrained in their radially-expanded states. By way of example and not limitation, (a) first perimeter P1 of distal main-module end 36 of main stent-graft 24 may equal at least 200% (e.g., at least 250%, at least 300%, or at least 400%) of second perimeter P2 of proximal main-module end 38 of the main stent-graft, (b) proximal dissection-reinforcement end 52 may be disposed along the main stent-graft no more than 20 mm proximal to proximal fenestration end 37, (c) dissection-reinforcement axial portion 48 may extends along the main stent-graft for a distance equal to between 5% and 32% of the greatest perimeter of the main stent-graft distally to distal fenestration end 35, and/or dissection-reinforcement axial portion 48 may have a radial strength that is at least 10% greater than an average radial strength of the entire main stent-graft.

Alternative Configurations of the Secondary Module

Reference is now made to FIG. 4, which is a schematic illustration of another configuration of secondary module 22, in accordance with an application of the present invention. In this configuration, when secondary module 22 is unconstrained in the radially-expanded state thereof:

the at least one lateral opening 174 includes at least first and second lateral openings 174A and 174B;

secondary covering element 132 is shaped so as to define first and second lateral openings 174A and 174B, each of which begins at and extends from proximal secondary-module end 138 toward sealing interface 172 along central longitudinal axis 140 for distance D3 equal to at least 50% of greatest width W1 of secondary module 22;

first and second lateral openings 174A and 174B face in different first and second radial directions extending from central longitudinal axis 140; and first and second lateral openings 174A and 174B at least partially axially overlap along central longitudinal axis 140.

For some applications, such as shown in FIG. 4, first and second lateral openings 174A and 174B axially coincide along central longitudinal axis 140. For some applications, such as shown in FIG. 4, the first and the second radial directions are opposite each other; in other words first and second lateral openings 174A and 174B face in radially-opposite directions.

For some applications, such as shown in FIG. 4, secondary covering element 132 is shaped so as to define two portions 176A and 176B, which (a) extend to and reach proximal secondary-module end 138, and (b) are shaped so as to define respective concave inner surfaces 178A and 178B that face each other and central longitudinal axis 140, and (c) are not joined to each other at proximal secondary-module end 138.

During deployment of secondary module 22 in aortic arch 19, such as described hereinabove with reference to FIG. 1, the secondary module is rotationally aligned such that one of first and second lateral openings 174A and 174B faces left common carotid artery 18, so as to allow blood flow into the left common carotid artery (and, for applications in which the secondary stent-graft is long enough, so as to allow blood flow into brachiocephalic artery 70). The other of the lateral openings faces downward toward the wall of aortic arch 19 opposite the left common carotid artery, and may serve to prevent blood from becoming trapped below the bottom side of the secondary module, which might cause blood coagulation.

Reference is now made to FIGS. 5 and 6, which are schematic illustrations of alternative configurations of secondary module 22, in accordance with respective applications of the present invention. In these configurations, when secondary module 22 is unconstrained in the radially-expanded state thereof:

secondary module 22 is shaped so as to define proximal secondary-module end 138, sealing interface 172, and central longitudinal axis 140 therebetween. Sealing interface 172 is sized and configured to form a blood-impervious seal with lateral fenestration 34 of main module 20;

secondary module 22 is shaped so as to define distal secondary-module end 136;

secondary covering element 132 is shaped so as to define at least one secondary-module lateral fenestration 134 disposed distal to proximal secondary-module end 138 and proximal to sealing interface 172, and a greatest axial length L2 of secondary-module lateral fenestration 134, measured parallel to central longitudinal axis 140, equals at least 33% (e.g., at least 50%) of first perimeter P1 of distal main-module end 36 of main stent-graft 24 of main module 20, when the main module is unconstrained in the radially-expanded state thereof.

For some applications, a greatest width W3 of secondary-module lateral fenestration 134, measured circumferentially around secondary module 22, equals at least 16% of first perimeter P1, such as at least 25% of first perimeter P1. These dimensions of greatest axial length L2 and greatest width W3 may allow secondary-module lateral fenestration 134 to allow sufficient blood flow to both left common carotid artery 18 and brachiocephalic artery 70.

Because secondary-module lateral fenestration 134 does not reach proximal secondary-module end 138, secondary covering element 132 is shaped so as to define an additional fixation zone 184 between secondary-module lateral fenestration 134 and proximal secondary-module end 138.

For some applications, at least one of secondary structural stent elements 131 traverses secondary-module lateral fenestration 134 when secondary module 22 is unconstrained in the radially-expanded state thereof. By way of example, in FIG. 5 one secondary structural stent element 131B is shown traversing secondary-module lateral fenestration 134, and in FIG. 6 two secondary structural stent elements 131B are shown traversing secondary-module lateral fenestration 134. Alternatively, three or more secondary structural stent elements 131B traverse secondary-module lateral fenestration 134. Such traversal may provide additional structural strength to secondary module 22 at the secondary-module lateral fenestration.

Typically, at least a portion of the border of secondary-module lateral fenestration 134 is defined by an undulating portion of one or more of secondary structural stent elements 131.

For some applications, a cross-sectional area of secondary module 22 gradually tapers from proximal secondary-module end 138 to sealing interface 172 when the secondary module is unconstrained in the radially-expanded state thereof.

For some applications, such as shown in FIG. 5, the at least one secondary-module lateral fenestration 134 comprises exactly one secondary-module lateral fenestration 134. For some of these applications, when secondary module 22 is unconstrained in the radially-expanded state thereof, secondary-module lateral fenestration 134 faces in a first radial direction extending from central longitudinal axis 140, and a portion 182 of secondary covering element 132 that faces in a second radial direction opposite the first radial direction extends to and reaches proximal secondary-module end 138. In other words, secondary module 22 is covered by secondary covering element 132 on the side circumferentially opposite secondary-module lateral fenestration 134, such that secondary-module lateral fenestration 134 and portion 182 face in radially-opposite directions.

During deployment of secondary module 20 in aortic arch 19, such as described hereinabove with reference to FIG. 1, the secondary module is rotationally aligned such that secondary-module lateral fenestration 134 faces left common carotid artery 18, so as to allow blood flow into the left common carotid artery.

Reference is made to FIG. 6. For some applications, secondary module 22 further comprises a flexible sheet 190, which (a) is blood-sealingly joined to a portion of a secondary border 180 of secondary-module lateral fenestration 134, which portion extends around at least 25% of a perimeter of the secondary border and includes a distal end 192 of secondary border 180 when secondary module 22 is unconstrained in the radially-expanded state thereof, and (b) extends radially inward from secondary border 180 (toward or past central longitudinal axis 140) when secondary module 22 is unconstrained in the radially-expanded state thereof. For some applications, a portion 194 of secondary structural stent elements 131 are attached to flexible sheet 190, which facilitates the radially-inward extension of flexible sheet 190 from secondary border 180.

As mentioned above, during deployment of secondary module 20 in aortic arch 19, such as described hereinabove with reference to FIG. 1, the secondary module is rotationally aligned such that secondary-module lateral fenestration 134 faces left common carotid artery 18. Flexible sheet 190 serves to direct a portion of the blood flow into the left common carotid artery.

Reference is now made to FIG. 7, which is a schematic illustration of yet another configuration of secondary module 22, in accordance with an application of the present invention. In this configuration, secondary module 22 is shaped so as to define proximal secondary-module end 138, sealing interface 172, and an anchoring axial portion 160 therebetween having central longitudinal axis 140 and an anchoring-portion length L3, measured along the central longitudinal axis from distal sealing interface 172 to proximal secondary-module end 138. Anchoring axial portion 160 is typically configured to (a) accommodate the anatomy of aortic arch 19 without blocking blood flow in the arch or to left common carotid artery 18 or brachiocephalic artery 70, (b) provide support for anchoring the secondary module in the aortic arch, and/or (c) provide support for secondary covering element 132, as described below.

Anchoring axial portion 160 includes a plurality (e.g., at least 8) of secondary structural stent elements 131, which, for example may comprise respective wires. For some applications, each of plurality of secondary structural stent elements 131 has two longitudinal portions 168 that extend toward (e.g., reach) distal sealing interface 172, and an intermediary longitudinal portion 170 that curves around proximal secondary-module end 136, when secondary module 22 is unconstrained in the radially-expanded state thereof (by way of example, one of such secondary structural stent elements 131 is labeled with reference numeral 167 in FIG. 7). Curved portions 170 of the plurality of secondary structural stent elements 131 may or may not converge at a single point at proximal secondary-module end 136. For some applications, the plurality of secondary structural stent elements 131 of anchoring axial portion 160 includes some structural stent elements that touch one another (e.g. at or near proximal secondary-module end 138), and no structural stent elements that are fixed to one another, when the secondary module is unconstrained in the radially-expanded state thereof.

For some applications, secondary structural stent elements 131 may include a loop element, e.g. a polygonal or elliptical (e.g., circular) loop, at proximal secondary-module end 136, to which loop element respective ends of the plurality of secondary structural stent elements 131 are coupled (configuration not shown).

In this configuration, when secondary module 22 is unconstrained in the radially-expanded state thereof, secondary covering element 132 at least covers secondary support element 130 along a covered axial portion 162 of anchoring axial portion 160. Secondary structural stent elements 131 of anchoring axial portion 160 provide support for secondary covering element 132, holding the secondary covering element open so as to facilitate blood flow to sealing interface 172 and through lateral fenestration 34 of main stent-graft 24.

Covered axial portion 162 extends proximally from distal sealing interface 172 for an axial covering distance D4 equal to at least 10% (e.g., at least 15%, such as at least 20%), no more than 50% (e.g., no more than 35%), and/or between 10% and 50% (e.g., between 10% and 35%, or between 20% and 35%) of anchoring-portion length L3, axial covering distance D4 measured along central longitudinal axis 140, when secondary module 22 is unconstrained in the radially-expanded state thereof. Secondary support element 130 is uncovered proximally to secondary covering element 132. When secondary module 22 is unconstrained in the radially-expanded state thereof, an uncovered axial portion 163 of anchoring axial portion 160 extends from proximal secondary-module end 138 to a proximal end 165 of covered axial portion 162, for an axial uncovered distance D7 equal to at least 50% (e.g., at least 65%), no more than 90% (e.g., no more than 80%), and/or between 50% and 90% (e.g., between 65% and 80%) of anchoring-portion length L3, measured along central longitudinal axis 140.

Typically, when secondary module 22 is unconstrained in the radially-expanded state thereof, anchoring axial portion 160 has a greatest anchoring-portion width W4 that is (a) greater than a greatest proximal-end width W5 at the proximal secondary-module end (W5 is optionally zero, as shown, for configurations in which the plurality of secondary structural stent elements 131 converge at a single point)

and (b) at least 20%, e.g., at least 50%, at least 75%, or at least 100%, greater than a greatest sealing-interface width W6 at a narrowest portion 164 of distal sealing interface 172, greatest anchoring-portion, sealing-interface, and proximal-end widths W4, W5, and W6 measured perpendicular to central longitudinal axis 140. For some applications, anchoring axial portion 160 has greatest anchoring-portion width W4 at an axial location 166 at an axial distance D5 from proximal secondary-module end 138 equal to at least 33%, no more than 60%, and/or between 33% and 60% of anchoring-portion length L3, axial distance D5 measured along central longitudinal axis 140, when secondary module 22 is unconstrained in the radially-expanded state thereof.

For some applications, axial covering distance D4 from distal sealing interface 172 is equal to at least 20% (e.g., at least 30%), no more than 100% (e.g., no more than 60%), and/or between 20% and 100% (e.g., between 30% and 60%) of an axial distance D6 between distal sealing interface 172 and axial location 166 of greatest anchoring-portion width W4, axial distance D6 measured along central longitudinal axis 140, when secondary module 22 is unconstrained in the radially-expanded state thereof.

For some applications, when secondary module 22 is unconstrained in the radially-expanded state thereof:
  anchoring-portion length L3 equals at least 50 mm, no more than 150 mm, and/or between 50 and 150 mm;
  greatest width W4 equals at least 30 mm, no more than 60 mm, and/or between 30 and 60 mm;
  greatest proximal-end width W5 equals at least 0 mm, no more than 35 mm, and/or between 0 and 35 mm, and/or at least 0 mm, no more than 40% of W4, and/or between 0 mm and 40% of W4;
  greatest sealing-interface width W6 equals at least 25 mm, no more than 40 mm, and/or between 25 and 40 mm;
  axial covering distance D4 equals at least 10 mm, no more than 30 mm, and/or between 10 and 30 mm;
  axial distance D5 equals at least 20 mm, no more than 80 mm, and/or between 20 and 80 mm;
  axial distance D6 equals at least 30 mm, no more than 80 mm, and/or between 30 and 80 mm; and/or
  axial uncovered distance D7 equals at least 30 mm, no more than 120 mm, and/or between 30 and 120 mm.

Figure 8:
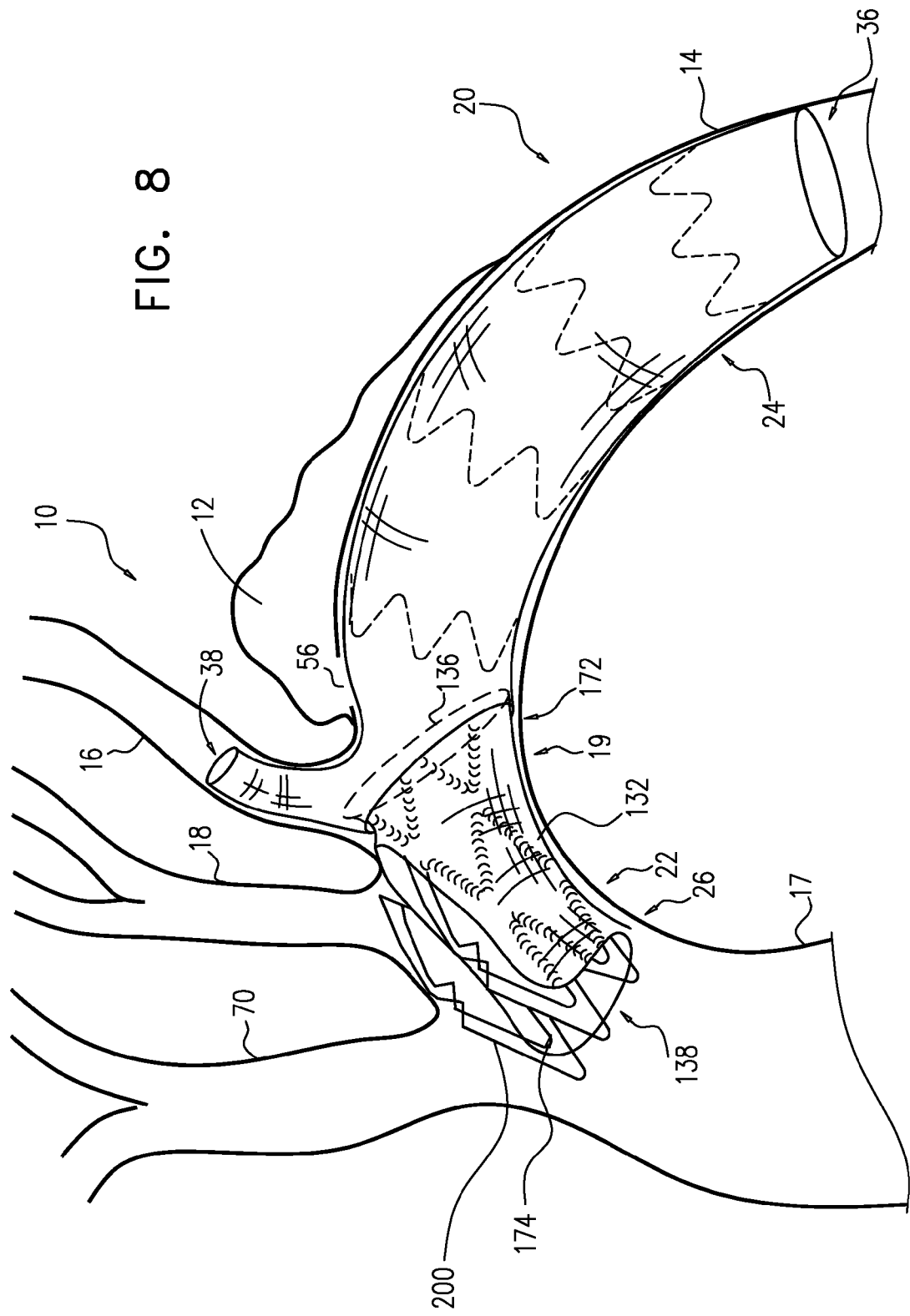
FIG. 8 is a schematic illustration of yet another configuration of the secondary module of the secondary module of the multi-component stent-graft system of FIG. 1, in accordance with an application of the present invention.

Reference is now made to FIG. 8, which is a schematic illustration of yet another configuration of secondary module 22, in accordance with an application of the present invention. FIG. 8 shows secondary module 22 deployed in aortic arch 19, sealingly coupled to lateral fenestration 34 of main module 20. In this configuration, secondary covering element 132 is shaped so as to define at least one lateral opening 174 that begins at and extends from proximal secondary-module end 138 toward sealing interface 172, such as described hereinabove with reference to FIGS. 3 and 4. Alternatively, the configuration of FIG. 8 may be implemented in combination with the configurations described hereinabove with reference to FIGS. 5, 6, and/or 7.

In this configuration, secondary module 22 comprises an extension structure 200, which is disposed radially outward of a fluid-flow path defined by secondary module 22, in a same radially direction as one of the at least one lateral opening of secondary covering element 132 (in the case of the configuration shown in FIGS. 3 and 4, at least one lateral opening 174, and in the case of FIGS. 5 and 6, at least one secondary-module lateral fenestration 134). Extension structure 200 typically comprises one or more of secondary structural stent elements 131. Extension structure 200 is shaped so as to help hold secondary module 22 properly positioned in aortic arch 19.

For some applications, at least one of secondary structural stent elements 131 traverses the lateral opening when the secondary module is unconstrained in the radially-expanded state thereof, and extension structure 200 is coupled to the lateral opening.

Figure 9:
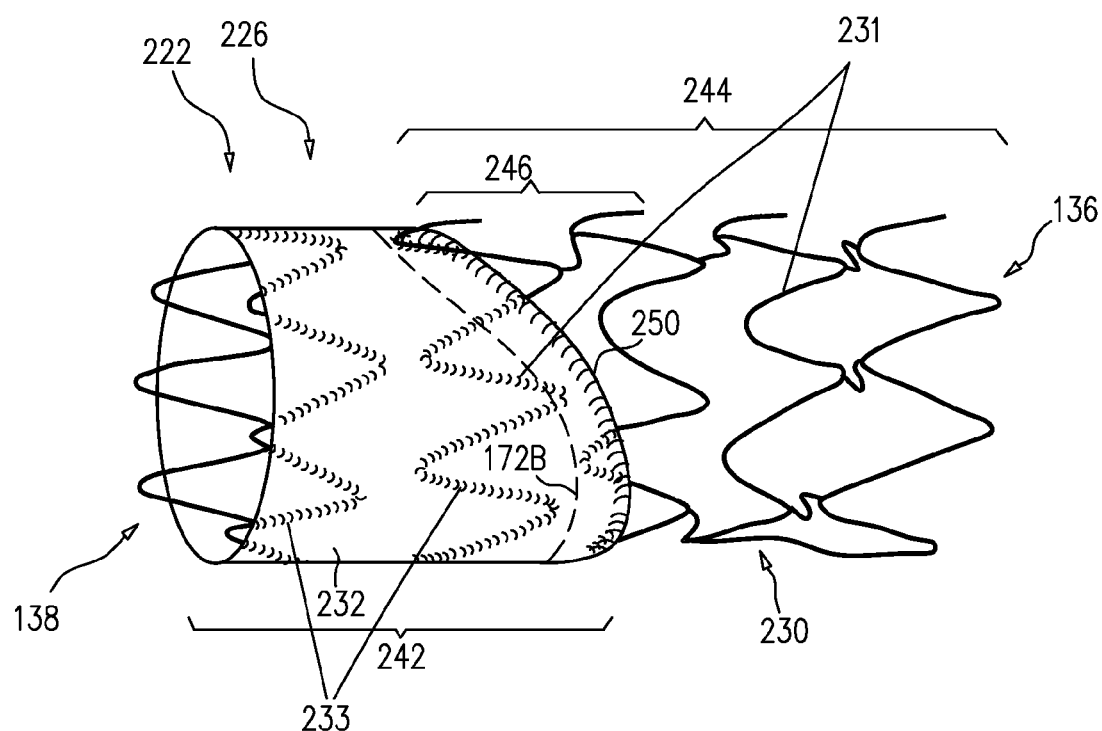
FIG. 9 is a schematic illustration of still another configuration of the secondary module of the secondary module of the multi-component stent-graft system of FIG. 1, in accordance with an application of the present invention.
Figure 10:
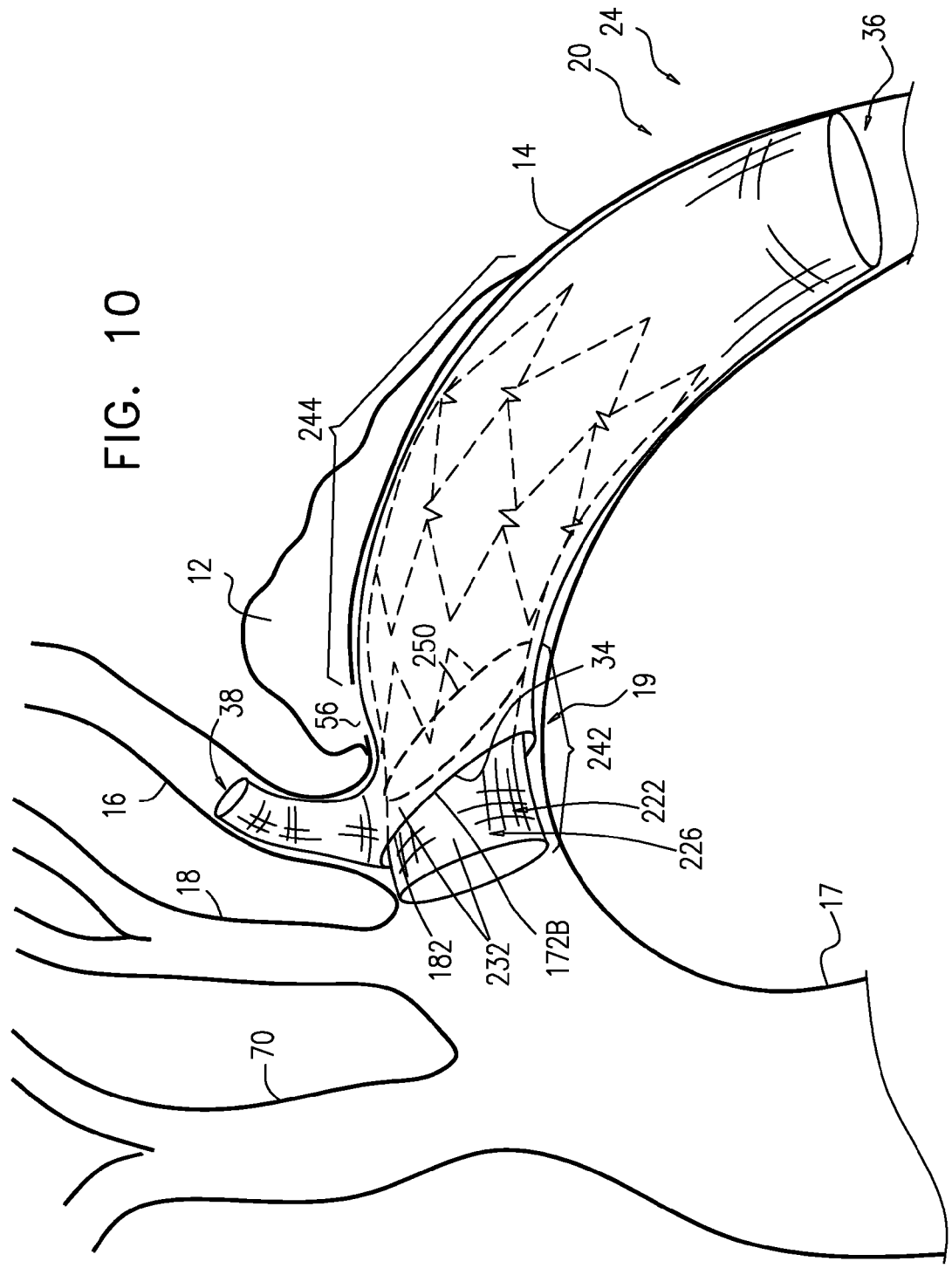
FIG. 10 is a schematic illustration of the secondary module of FIG. 9 deployed in an aortic arch, sealingly coupled to a lateral fenestration of a main module of the multi-component stent-graft system, in accordance with an application of the present invention.

Reference is now made to FIGS. 9 and 10, which are schematic illustrations of a secondary module 222, in accordance with an application of the present invention. FIG. 9 shows secondary module 222, and FIG. 10 shows secondary module 222 deployed in aortic arch 19, sealingly coupled to lateral fenestration 34 of main module 20. FIG. 9 shows secondary module 222 unconstrained in its radially-expanded state, i.e., no forces are applied to the module by a delivery tool, walls of a blood vessel, or otherwise.

Secondary module 222 comprises a non-bifurcated secondary stent-graft 226, which typically comprises a secondary generally tubular support element 230 and a secondary covering element 232 that is attached to and at least partially covers a covered axial portion 242 of support element 230 and at least partially does not cover an uncovered axial portion 244 of support element 230. For some applications, secondary covering element 232 partially covers an overlap axial portion 246 along which first and second axial portions 244 and 246 axially overlap; for example, a distal end 250 of secondary covering element 232 may be generally diagonally-shaped, such as shown in FIG. 9.

Support element 230 typically comprises a plurality of secondary structural stent elements 231. For some applications, secondary structural stent elements 231 are arranged as a plurality of circumferential stent springs 233. Secondary covering element 232 serves as a blood flow guide through at least a portion of the secondary stent-graft. Secondary covering element 232 typically comprises at least one biologically-compatible substantially blood-impervious flexible sheet, which is attached (such as by stitching) to at least a portion of the respective support element, on either side of the surfaces defined by the support element. The flexible sheet may comprise, for example, a polymeric material (e.g., a polyester, or polytetrafluoroethylene), a textile material (e.g., polyethylene terephthalate (PET)), natural tissue (e.g., saphenous vein or collagen), or a combination thereof.

As shown in FIG. 10, secondary module 222 is configured to be partially inserted into main module 20, such that uncovered axial portion 244 is positioned within main module 20, and covered axial portion 242 is partially positioned outside of and partially positioned within main module 20, through lateral fenestration 34. A portion of secondary covering element 232 passes through lateral fenestration 34, so as to form a blood-tight seal with main module 20. The portion of covered axial portion 242 positioned outside of main module 20 is short enough so as to not block blood flow left common carotid artery 18 or brachiocephalic artery 70.

Figure 11:
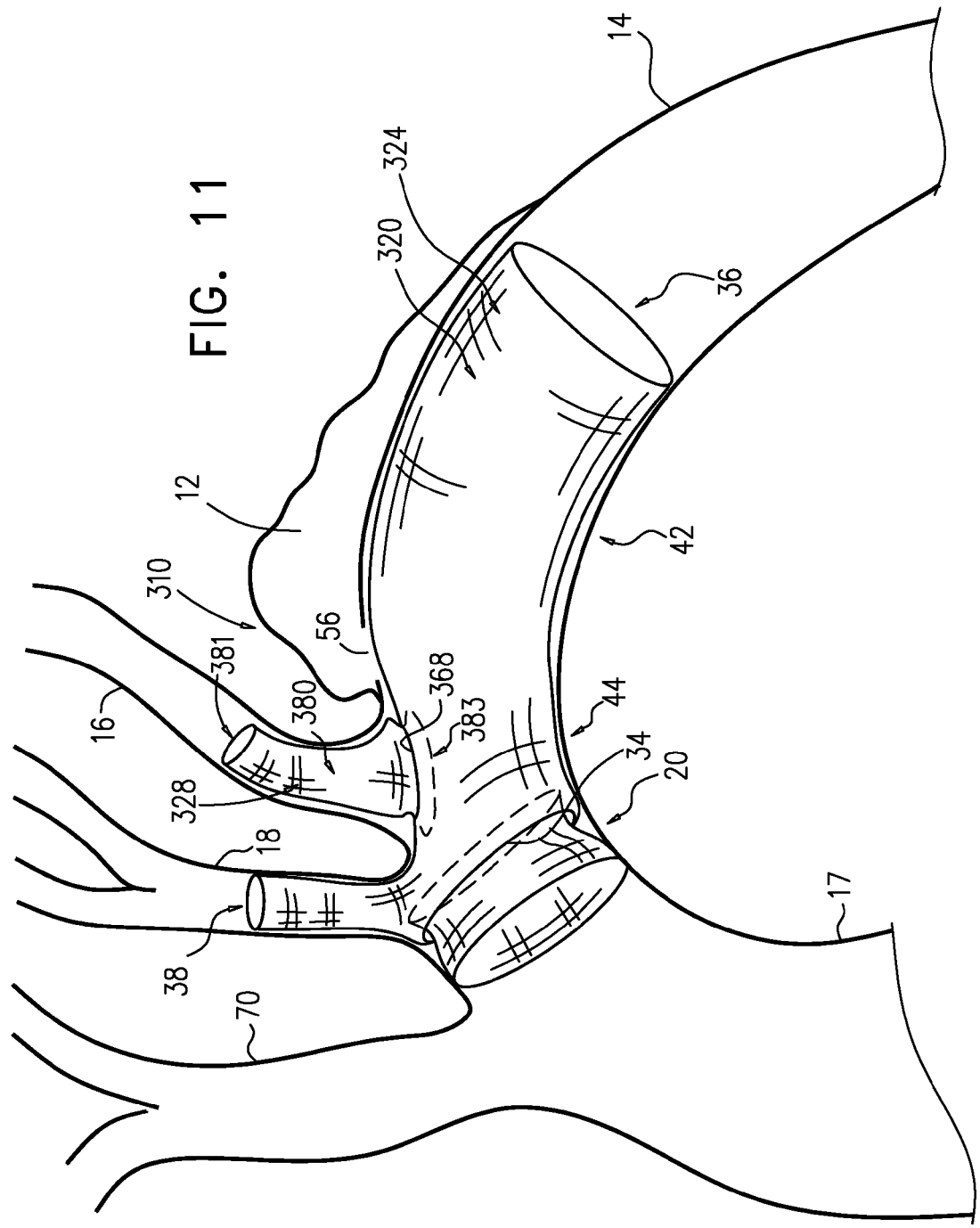
FIG. 11 is a schematic illustration of another multi-component stent-graft system, in accordance with an application of the present invention.

Reference is now made to FIGS. 11, 12, and 13A-B. FIG. 11 is a schematic illustration of a multi-component stent-graft system 310, in accordance with an application of the present invention. Multi-component stent-graft system 310 comprises a main module 320, a secondary module 322, and typically a tertiary module 328, which comprise respective stent-grafts, as described below. The stent-grafts are configured to assume radially-compressed states, such as when initially positioned in one or more outer tubes of one or more delivery tools, and to assume radially-expanded states upon being deployed from the outer tube(s). FIG. 11 shows the stent-grafts in their radially-expanded states in situ.

Figure 12:
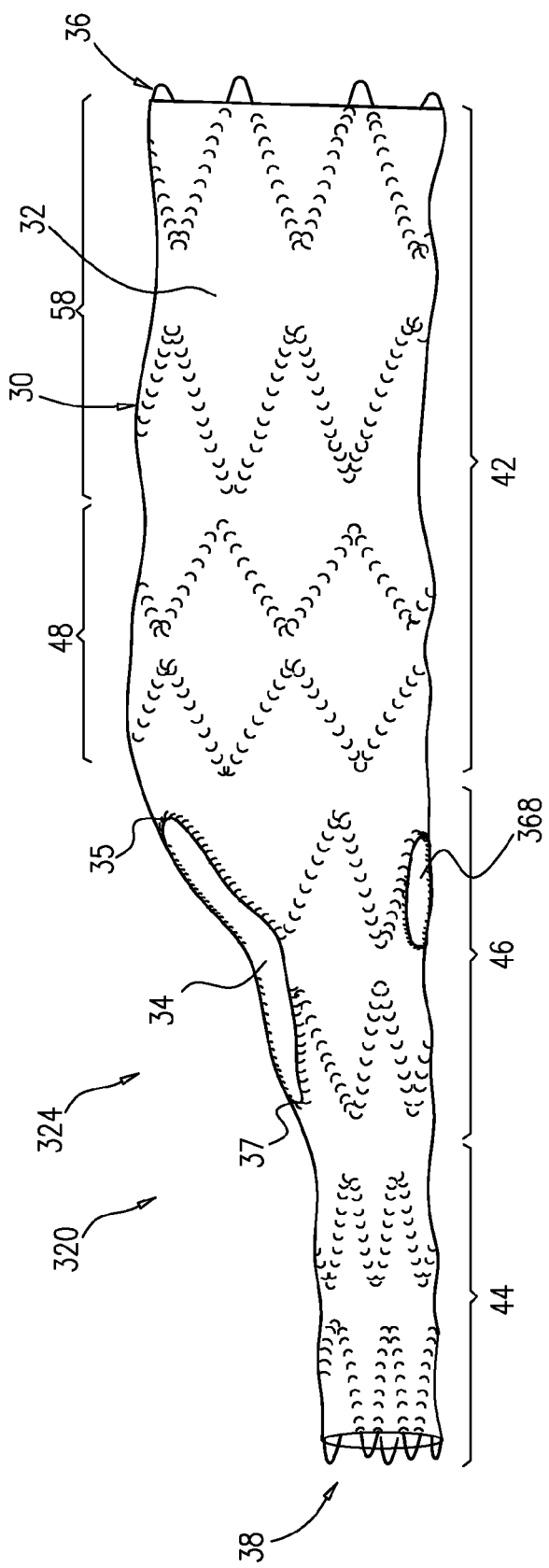
FIG. 12 is a schematic illustration of a main module of the multi-component stent-graft system of FIG. 11, in accordance with an application of the present invention.

FIG. 12 is a schematic illustration of main module 320, in accordance with an application of the present invention.

FIG. 12 shows main stent-graft 24 unconstrained in its radially-expanded state, i.e., no forces are applied to the stent-graft by a delivery tool, walls of a blood vessel, or otherwise. Other than as described hereinbelow, main module 320 may implement any or all of the features of main module 20, described hereinabove with reference to FIGS. 1 and 2A-B, including, but not limited to, dissection-reinforcement axial portion 48, descending-aorta axial portion 42, supra-arch axial portion 44, arch axial portion 46, and/or distal axial portion 58. Main module 320 comprises a generally tubular main stent-graft 324, such as described hereinabove with reference to FIGS. 2A-B regarding main stent-graft 24.

Unlike stent-graft 24, main covering element 32 and main support element 30 of main stent-graft 324 are shaped so as to together define two lateral fenestrations through main stent-graft 324: a first lateral fenestration 34, as defined by stent-graft 24, and a second lateral fenestration 368, when main stent-graft 324 is unconstrained in its radially-expanded state. Typically, when main stent-graft 324 is unconstrained in its radially-expanded state, first lateral fenestration 34 faces in a first radial direction, and second lateral fenestration 368 faces in a second radially direction generally circumferentially opposite the first radial direction. For example, if the stent-graft is viewed from one end, the first lateral fenestration may be disposed at between 11 o'clock and 1 o'clock (e.g., at 12 o'clock), and the second lateral fenestration may disposed at between 5 o'clock and 7 o'clock (e.g., at 6 o'clock).

When multi-component stent-graft system 310 is implanted as shown in FIG. 11, first lateral fenestration 34 serves as an inferior lateral fenestration, and second lateral fenestration 368 serves as a superior lateral fenestration.

Typically, a first perimeter of first (inferior) lateral fenestration 34 equals at least 200%, no more than 400%, and/or between 200% and 400% of a second perimeter of second (superior) lateral fenestration 368.

For some applications, supra-arch axial portion 44 of main stent-graft 324 is internally lined with ePTFE film, or main covering element 32 of main stent-graft 324 comprises entirely ePTFE (and thus does not comprise any polyester). Optionally, main covering element 32 along other portions of the main stent-graft comprises polyester. (This configuration may also be implemented in main stent-graft 24, described hereinabove with reference to FIGS. 1 and 2A-B.)

Other than as described hereinbelow, secondary module 322 may implement any of the configurations of secondary module 20 described hereinabove with reference to FIGS. 1, 3, 4, 5, 6, 7, 8, 9, and/or 10 mutatis mutandis. By way of example and not limitation, secondary module is shown in FIG. 11 in the configuration of secondary module 20 shown in FIGS. 1 and 3. (For applications in which secondary module is configured as described hereinabove with reference to FIG. 5 and/or FIG. 6, greatest axial length L2 of secondary-module lateral fenestration 134 may be less than described hereinabove, e.g., may equal at least 20% of first perimeter P1 of distal main-module end 36 of main stent-graft 24 of main module 20, when the main module is unconstrained in the radially-expanded state thereof. In the configuration described with reference to FIGS. 11 and 12, secondary-module lateral fenestration 134 need only be sufficiently large to allow sufficient blood flow to brachiocephalic artery 70.)

Figure 13A:
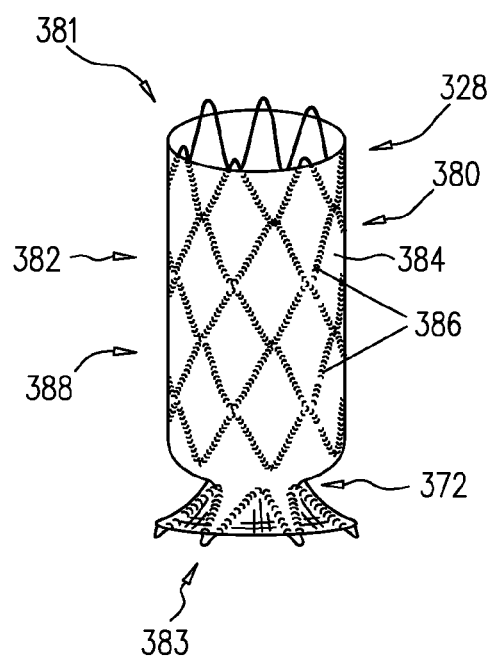
FIGS. 13A and 13B are schematic illustrations of respective configurations of a tertiary module of the multi-component stent-graft system of FIG. 11, in accordance with respective applications of the present invention.
Figure 13B:
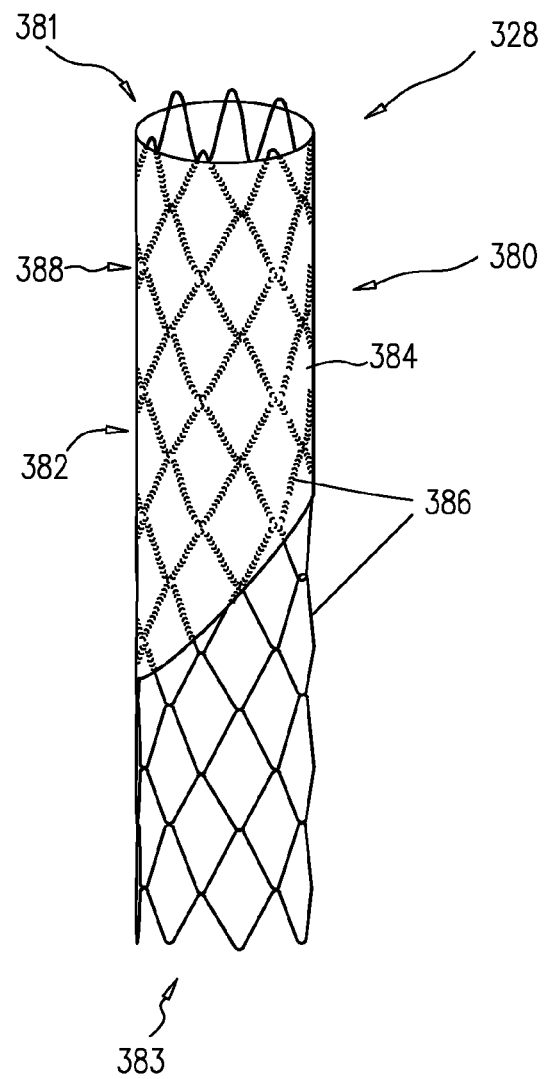

FIGS. 13A and 13B are schematic illustrations of respective configurations of tertiary module 328, in accordance with respective applications of the present invention. Tertiary module 328 comprises a generally tubular tertiary stent-graft 380, which typically comprises a tertiary generally tubular support element 382 and a tertiary covering element 384 that is attached to and at least partially covers (e.g., only partially covers) the tertiary support element. Tertiary module 328 and stent-graft 380 have distal and proximal ends 381 and 383. Support element 382 typically comprises a plurality of tertiary structural stent elements 386. For some applications, tertiary structural stent elements 386 are arranged as a plurality of circumferential stent springs 388. Tertiary covering element 384 serves as a blood flow guide through at least a portion of the tertiary stent-graft. Tertiary covering element 384 typically comprises at least one biologically-compatible substantially blood-impervious flexible sheet, which is attached (such as by stitching) to at least a portion of the respective support element, on either side of the surfaces defined by the support element. The flexible sheet may comprise, for example, a polymeric material (e.g., a polyester, or polytetrafluoroethylene), a textile material (e.g., polyethylene terephthalate (PET)), natural tissue (e.g., saphenous vein or collagen), or a combination thereof.

In the configuration shown in FIG. 13A, tertiary module 328 is shaped so as to define a sealing interface 372, which is similar to sealing interface 172 described hereinabove with reference to FIGS. 3, 4, 5, 6, and 7, and/or hereinbelow with reference to FIGS. 1, 3, 4, 5, 6, 7, 8, and 11. Sealing interface 372 is sized and configured to form a blood-impervious seal with second (superior) lateral fenestration 368 of main module 320, as shown in FIG. 11. For some applications, sealing interface 372 and/or second (superior) lateral fenestration 368 implement sealing techniques described in US Patent Application Publication 2012/0179236 to Benary et al. and/or PCT Publication WO 2013/005207 to Shalev.

In the configuration shown in FIG. 13A, tertiary module 328 includes covered and uncovered axial portions, similar to the covered and uncovered axial portions 242 and 244 described hereinabove with reference to FIG. 9. Tertiary module 328 may implement any of the features described hereinabove with reference to FIG. 9, mutatis mutandis. Tertiary module 328 is sized and configured to form a blood-impervious seat with second (superior) lateral fenestration 368 of main module 320, using the techniques described hereinabove with reference to FIG. 10, mutatis mutandis.

Reference is again made to FIG. 11. In an exemplary transluminal delivery procedure for implanting multi-component stent-graft system 310, the stent-grafts of system 310 are endovascularly (typically percutaneously) introduced into the thoracic aorta, such as via one of the iliac arteries, while the stent-grafts are positioned in one or more outer tubes of a delivery tool in their radially-compressed states.

Typically, the exemplary procedure begins with the advancing of a guidewire up the descending aorta and into left common carotid artery 18. Main stent-graft 324 of main module 320 is initially positioned in its radially-compressed state within an outer tube of a delivery tool, typically near a leading end of the outer tube. The outer tube is advanced over the guidewire, until main stent-graft 324 is partially disposed in left common carotid artery 18 and partially disposed in the upper part of the descending aorta. The guidewire is withdrawn, leaving the outer tube in place. The main stent-graft is held in place as the outer tube is withdrawn, thereby delivering the main stent-graft from the outer tube. Main stent-graft 324 typically self-expands, until it assumes its radially-expanded state, upon reaching typically about 80-90% of its maximum unconstrained size, and/or being constrained from further expansion by the wall of the blood vessels, as shown in FIG. 11. Alternatively, the main stent-graft (and/or the other stent-grafts, as described hereinbelow) is delivered using an over-the-wire (OTW) approach, in which the guidewire is left in place until the stent-graft is expanded, and thereafter the guidewire is withdrawn.

Descending-aorta axial portion 42 of main stent-graft 324, including distal main-module end 336, is positioned in the upper part of the descending aorta, and supra-arch axial portion 44 of main stent-graft 324, including proximal main-module end 338, is positioned in left common carotid artery 18. First (inferior) lateral fenestration 34 is disposed in aortic arch 19 facing upstream, generally toward ascending aorta 17, in a vicinity of the bifurcation of aortic arch 19 and left common carotid artery 18. Second (superior) lateral fenestration 368 is axially aligned with and faces left subclavian artery 16. For some applications, proper rotational alignment and/or axial orientation of the first and/or second lateral fenestrations is achieved using fluoroscopy. For example, main stent-graft 324 may comprise one or more radiopaque markers in a vicinity of (e.g., on a periphery of) the one or both of the lateral fenestrations.

A guidewire (either the same guidewire used to deploy the main stent-graft, or a second guidewire) is advanced up the descending aorta, through a proximal portion of main stent-graft 324, through second (superior) lateral fenestration 368, and into left subclavian artery 16. Tertiary stent-graft 380 of tertiary module 328 is positioned in its radially-compressed state within an outer tube of a delivery tool (either the same outer tube used to deploy the main stent-graft, or a second outer tube), typically near a leading end of the outer tube. The outer tube is advanced over the guidewire, until tertiary stent-graft 380 is partially disposed in left subclavian artery 16, and partially disposed within radially-expanded main stent-graft 324. The guidewire is withdrawn, leaving the outer tube in place.

The tertiary stent-graft is held in place as the outer tube is withdrawn, thereby delivering the tertiary stent-graft from the outer tube. Tertiary stent-graft 380 typically self-expands, until it assumes its radially-expanded state, upon reaching its maximum unconstrained size, and/or being constrained from further expansion by the wall of the left subclavian artery. Tertiary stent-graft 380 is thus adapted for transluminal delivery in its radially-compressed state through a portion of main stent-graft 324 and second (superior) lateral fenestration 368, while the main stent-graft is in its radially-expanded state.

A proximal portion of tertiary stent-graft 380, including distal end 383, is positioned within main stent-graft 324, and tertiary covering element 384 (e.g., at sealing interface 372 in the configuration shown in FIGS. 11 and 13A) of tertiary stent-graft 380 is sealingly coupled to second (superior) lateral fenestration 368 of main stent-graft 324.

A guidewire (either the same guidewire used to deploy the main stent-graft and/or tertiary stent-graft, or another guidewire) is advanced up the descending aorta, through a distal portion of main stent-graft 324, out of first (inferior) lateral fenestration 34, and into aortic arch 19, extending toward, or partially into, ascending aorta 17. Secondary stent-graft 26 of secondary module 322 is positioned in its radially-compressed state within an outer tube of a delivery tool (either the same outer tube used to deploy the main stent-graft and/or the tertiary stent-graft, or another outer tube), typically near a leading end of the outer tube. The outer tube is advanced over the guidewire, until secondary stent-graft 26 is partially disposed in aortic arch 19, extending toward, or partially into, ascending aorta 17, and partially disposed within radially-expanded main stent-graft 324 in the upper part of the descending aorta. The guidewire is withdrawn, leaving the outer tube in place.

The secondary stent-graft is rotationally aligned such that the at least one lateral opening 174 faces left common carotid artery 18, so as to allow blood flow to the left common carotid artery (and, for applications in which the secondary stent-graft is long enough, so as to allow blood flow into brachiocephalic artery 70). The secondary stent-graft may comprise one or more radiopaque markers to facilitate such proper rotational alignment. For example, the radiopaque markers may be positioned on one or more edges of the at least one lateral opening.

The secondary stent-graft is held in place as the outer tube is withdrawn, thereby delivering the secondary stent-graft from the outer tube. Secondary stent-graft 26 typically self-expands, until it assumes its radially-expanded state, upon reaching its maximum unconstrained size, and/or being constrained from further expansion by the wall of the blood vessels. Secondary stent-graft 26 is thus adapted for transluminal delivery in its radially-compressed state through a portion of main stent-graft 324 and first (inferior) lateral fenestration 34, while the main stent-graft is in its radially-expanded state.

A distal portion of secondary stent-graft 26, including distal secondary-module end 136, is positioned within main stent-graft 324, and sealing interface 172 of secondary stent-graft 26 is sealingly coupled to first (inferior) lateral fenestration 34 of main stent-graft 324. A proximal portion of secondary stent-graft 26, including proximal secondary-module end 138, is positioned in aortic arch 19. As mentioned, the at least one lateral opening 174 faces left common carotid artery 18. Secondary module 322 reduces blood turbulence in the aortic arch, and serves as a funnel that creates a gradual taper of the blood flow into first (inferior) lateral fenestration 34 of main stent-graft 324.

Alternatively, secondary module 322 is deployed before tertiary module 328 is deployed.

Reference is made to FIGS. 1, 3, 4, 5, 6, 7, 8, and 11. For some applications, sealing interface 172 is shaped so as to define a neck portion longitudinally flanked by proximal and distal portions. The neck portion is generally radially narrower than the proximal and distal portions. For some applications, sealing interface 172 and/or lateral fenestration 34 implement sealing techniques described in US Patent Application Publication 2012/0179236 to Benary et al. and/or PCT Publication WO 2013/005207 to Shalev, which are incorporated herein by reference. Alternatively, all of the configurations of secondary module 22 described with reference to FIGS. 1, 3, 4, 5, 6, 7, 8, and 11 may implement the sealing techniques described hereinabove regarding secondary module 222 with reference to FIGS. 9 and 10 (i.e., rather than defining a narrower neck portion, secondary covering element 132 of secondary stent-graft 26 may instead only partially axially cover secondary support element 130 and define sealing interface 172B).

Reference is again made to FIGS. 1 and 2A-B, as well as to FIGS. 14A-B, which are schematic illustrations of kinking properties of different axial portions of main stent-graft 24, in accordance with an application of the present invention. For some applications:

if distal axial portion 58 of main stent-graft 24, when the main stent-graft is in the radially-expanded state, is placed and constrained in a first curved tube 390 having a circular cross-section and an inner diameter equal to an outer diameter of distal axial portion 58, distal axial portion 58 experiences kinking only when at least an axial portion 392 of the first curved tube has less than a first radius of curvature r1, as shown in FIG. 14A, and if dissection-reinforcement axial portion 48 of main stent-graft 24, when the main stent-graft is in the radially-expanded state, is placed and constrained in a second curved tube 394 having a circular cross-section and an inner diameter equal to an outer diameter of dissection-reinforcement axial portion 48, dissection-reinforcement axial portion 48 experiences kinking only when at least an axial portion 396 of the second curved tube has less than a second radius of curvature r2, which second radius of curvature is at least 30%, e.g., at least 50%, less than the first radius of curvature r1, as shown in FIG. 14B.

As used in the present application, including in the claims, "kinking," means that the graft material of main covering element 32 is pinched, or folded in a blood-flow-disturbing manner. It is noted that the outer diameters of the axial portions may vary axially therealong, in which case the inner diameters of the curved tubes would also correspondingly vary. It is also noted that the first and second curved tubes are not elements of multi-component stent-graft system 10, but are rather geometric constructs used to describe certain features of the main stent-graft.

Reference is now made to FIG. 15, which is a schematic illustration of kinking in a stent-graft 400. As described hereinabove with reference to FIGS. 2A-B and 14A-B, for some applications dissection-reinforcement axial portion 48 is configured to avoid kinking. Without such configuration, for example if substantial axial spacing is provided between adjacent stent springs 402 of stent-graft 400, the stent-graft would be more prone to kinking 404, as shown in FIG. 14.

Although multi-component stent-graft systems 10 and 310 are generally described herein as being used for treating Type B aortic dissection, the scope of the present invention also includes using these systems for treating other conditions, such as aortic aneurysms.

The scope of the present invention includes embodiments described in the following applications, which are assigned to the assignee of the present application and are incorporated herein by reference. In an embodiment, techniques and apparatus described in one or more of the following applications are combined with techniques and apparatus described herein:

U.S. application Ser. No. 12/529,936, filed Sep. 4, 2009, which issued as U.S. Pat. No. 8,317,856

U.S. Provisional Application 60/892,885, filed Mar. 5, 2007

U.S. Provisional Application 60/991,726, filed Dec. 2, 2007

U.S. Provisional Application 61/219,758, filed Jun. 23, 2009

U.S. Provisional Application 61/221,074, filed Jun. 28, 2009

U.S. application Ser. No. 13/380,278, filed Dec. 22, 2011, which published as US Patent Application Publication 2012/0150274

U.S. application Ser. No. 13/384,075, filed Jan. 13, 2012, which published as US Patent Application Publication 2012/0179236

U.S. application Ser. No. 13/505,996, filed May 3, 2012, which published as US Patent Application Publication 2012/0310324

U.S. application Ser. No. 13/512,778, filed Sep. 24, 2012, which published as US Patent Application Publication 2013/0013050

U.S. application Ser. No. 13/513,397, filed Jun. 1, 2012, which published as US Patent Application Publication 2012/0330399

U.S. application Ser. No. 13/514,240, filed Jun. 6, 2012, which published as US Patent Application Publication 2013/0013051

U.S. application Ser. No. 13/577,161, filed Aug. 3, 2012, which published as US Patent Application Publication 2013/0035751

U.S. application Ser. No. 13/031,871, filed Feb. 22, 2011, which published as US Patent Application Publication 2011/0208289

U.S. Provisional Application 61/496,613, filed Jun. 14, 2011

U.S. Provisional Application 61/505,132, filed Jul. 7, 2011

U.S. Provisional Application 61/529,931, filed Sep. 1, 2011

PCT Application PCT/IL2012/000060, filed Feb. 2, 2012, which published as PCT Publication WO 2012/104842

PCT Application PCT/IL2012/000083, filed Feb. 16, 2012, which published as PCT Publication WO 2012/111006

PCT Application PCT/IL2012/000095, filed Mar. 1, 2012, which published as PCT Publication WO 2012/117395

PCT Application PCT/IL2012/000148, filed Apr. 4, 2012, which published as PCT Publication WO 2013/030818

PCT Application PCT/IL2012/000190, filed May 15, 2012, which published as PCT Publication WO 2013/171730

U.S. patent application Ser. No. 13/523,296, filed Jun. 14, 2012, which published as US Patent Application Publication 2012/0323305

PCT Application PCT/IL2012/000241, filed Jun. 19, 2012, which published as PCT Publication WO 2012/176187

PCT Application PCT/IL2012/000269, filed Jul. 2, 2012, which published as PCT Publication WO 2013/005207

PCT Application PCT/IL2012/050424, filed Oct. 29, 2012, which published as PCT Publication WO 2013/065040

PCT Application PCT/IL2012/050506, filed Dec. 4, 2012, which published as PCT Publication WO 2013/084235

U.S. Provisional Application 61/749,965, filed Jan. 8, 2013, entitled, "Minimization of stent-graft migration during implantation"

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

The invention claimed is:

1. Apparatus comprising a generally tubular stent-graft, which has distal and proximal stent-graft ends and comprises:

a generally tubular support element, which comprises a plurality of structural stent elements; and a covering element that is attached to and at least partially covers the support element, wherein when the stent-graft is unconstrained in a radially-expanded state:

the covering element and the support element are shaped so as to together define a lateral fenestration having distal and proximal fenestration ends, a first perimeter of the distal stent-graft end equals at least 200% of a second perimeter of the proximal stent-graft end, and the stent-graft includes a dissection-reinforcement axial portion, which (a) includes a portion of the structural stent elements, (b) has (i) a distal dissection-reinforcement end and (ii) a proximal dissection-reinforcement end that is disposed along the stent-graft no more than 20 mm proximal to the proximal fenestration end, (c) extends along the stent-graft for a distance, and (d) has a radial strength that is at least 10% greater than an average radial strength of the entire stent-graft, wherein the distance is equal to between 5% and 32% of a greatest perimeter of the stent-graft distally to the distal fenestration end.

2. The apparatus according to claim 1,
wherein the portion of the structural stent elements included by the dissection-reinforcement axial portion is a first portion of the structural stent elements, and
wherein when the stent-graft is unconstrained in the radially-expanded state:
the stent-graft includes a distal-end axial portion, which includes a second portion of the structural stent elements, and
the distal-end axial portion axially extends along the stent-graft from the distal end of the stent-graft for a distance, wherein the distance is equal to between 5% and 32% of a greatest perimeter of the stent-graft distally to the distal fenestration end, and
the distal-end axial portion has a radial strength that is at least a 10% greater than the average radial strength of the entire stent-graft.

3. The apparatus according to claim 1, wherein an axial length of the dissection-reinforcement axial portion is between 1 and 3 cm when the stent-graft is unconstrained in the radially-expanded state.

4. The apparatus according to claim 1, wherein the proximal dissection-reinforcement end is disposed along the stent-graft no more proximal than the distal fenestration end when the stent-graft is unconstrained in the radially-expanded state.

5. The apparatus according to claim 1, wherein the proximal dissection-reinforcement end is disposed along the stent-graft between the distal fenestration end and the proximal fenestration end, inclusive, when the stent-graft is unconstrained in the radially-expanded state.

6. The apparatus according to claim 1, wherein a distance between the distal dissection-reinforcement end and the distal stent-graft end equals between 32% and 160% of a largest perimeter of the stent-graft when the stent-graft is unconstrained in the radially-expanded state.

7. The apparatus according to claim 1, wherein the dissection-reinforcement axial portion extends along the stent-graft for a distance when the stent-graft is unconstrained in the radially-expanded state, wherein the distance is equal to between 10% and 22% of a greatest perimeter of the stent-graft distally to the distal fenestration end.

8. The apparatus according to claim 1, wherein the first perimeter equals at least 250% of the second perimeter.

9. The apparatus according to claim 1, wherein the dissection-reinforcement axial portion is configured to be generally straight when the stent-graft is unconstrained in the radially-expanded state.

10. The apparatus according to claim 1, wherein the structural stent elements of the dissection-reinforcement axial portion are arranged as a plurality of circumferential stent springs, and wherein a height, measured axially along the stent-graft, of at least one of the stent springs varies by less than 10% around a circumference of the stent spring when the stent-graft is unconstrained in the radially-expanded state.

11. The apparatus according to claim 1, wherein the stent-graft is shaped so as to define exactly one lateral fenestration when the stent-graft is unconstrained in the radially-expanded state.

12. The apparatus according to claim 1,
wherein the lateral fenestration is an inferior first lateral fenestration, which faces in a first radial direction, and
wherein, when the stent-graft is unconstrained in the radially-expanded state, the covering element and the support element are shaped so as to together define a superior second lateral fenestration, which faces in a second radial direction generally opposite the first radial direction.

13. Apparatus comprising a generally tubular stent-graft, which has distal and proximal stent-graft ends and comprises:
a generally tubular support element, which comprises a plurality of structural stent elements arranged as a plurality of circumferential stent springs; and
a covering element that is attached to and at least partially covers the support element,
wherein when the stent-graft is unconstrained in a radially-expanded state:
the covering element and the support element are shaped so as to together define a lateral fenestration having distal and proximal fenestration ends,
a first perimeter of the distal stent-graft end equals at least 200% of a second perimeter of the proximal stent-graft end,
the stent-graft includes a dissection-reinforcement axial portion, which (a) includes a first plurality of the stent springs, (b) has (i) a distal dissection-reinforcement end and (ii) a proximal dissection-reinforcement end that is disposed along the stent-graft no more than 20 mm proximal to the proximal fenestration end, (c) extends along the stent-graft for a distance, and (d) is configured to be generally straight, wherein the distance is equal to between 5% and 32% of a greatest perimeter of the stent-graft distally to the distal fenestration end,
the stent-graft includes a distal axial portion, which (a) includes a second plurality of the stent springs, (b) is disposed along the stent-graft distal and axially adjacent to the distal dissection-reinforcement end, (c) extends along the stent-graft for a distance, wherein the distance is equal to between 5% and 32% of the greatest perimeter of the stent-graft distally to the distal fenestration end,
the stent springs have respective average heights, measured axially along the stent-graft, and
an average of the average heights of the first plurality of the stent springs is less than 75% of the average height of a proximal-most one of the second plurality of the stent springs.

14. The apparatus according to claim 13, wherein each of the average heights of the first plurality of the stent springs is less than 75% of the average heights of the proximal-most one of the second plurality of stent springs when the stent-graft is unconstrained in the radially-expanded state.

15. The apparatus according to claim 13, wherein the average of the average heights of the first plurality of the stent springs is less than 75% of the average height of a second one of the second plurality of stent springs, other than the proximal-most one of the second plurality of stent springs when the stent-graft is unconstrained in the radially-expanded state.

16. The apparatus according to claim 13, wherein the average of the average heights of the first plurality of the stent springs is less than 75% of each of the average heights of the second plurality of stent springs when the stent-graft is unconstrained in the radially-expanded state.

17. The apparatus according to claim 13, wherein the distal axial portion is configured to be generally straight when the stent-graft is unconstrained in the radially-expanded state.

18. The apparatus according to claim 13, wherein an axial length of the dissection-reinforcement axial portion is between 1 and 3 cm when the stent-graft is unconstrained in the radially-expanded state.

19. The apparatus according to claim 13, wherein the proximal dissection-reinforcement end is disposed along the stent-graft no more proximal than the distal fenestration end when the stent-graft is unconstrained in the radially-expanded state.

20. The apparatus according to claim 13, wherein the proximal dissection-reinforcement end is disposed along the stent-graft between the distal fenestration end and the proximal fenestration end, inclusive, when the stent-graft is unconstrained in the radially-expanded state.

21. The apparatus according to claim 13, wherein an axial spacing between two of the first plurality of the stent springs equals less than 10% of an average of the average heights of the two stent springs.

22. The apparatus according to claim 13, wherein the first perimeter equals at least 300% of the second perimeter.

23. The apparatus according to claim 13, wherein the dissection-reinforcement axial portion extends along the stent-graft for a distance when the stent-graft is unconstrained in the radially-expanded state, wherein the distance is equal to between 10% and 32% of the greatest perimeter of the stent-graft distally to the distal fenestration end.

24. The apparatus according to claim 13, wherein the distal axial portion extends to and reaches the distal stent-graft end.

25. The apparatus according to claim 13, wherein the average height of at least one of the first plurality of stent springs varies by less than 10% around a circumference of the stent spring when the stent-graft is unconstrained in the radially-expanded state.

26. The apparatus according to claim 13,
wherein, if the distal axial portion, when the stent-graft is in the radially-expanded state, is placed and constrained in a first curved tube having a circular cross-section and an inner diameter equal to an outer diameter of the distal axial portion, the distal axial portion experiences kinking only when at least an axial portion of the first curved tube has less than a first radius of curvature, and
wherein, if the dissection-reinforcement axial portion, when the stent-graft is in the radially-expanded state, is placed and constrained in a second curved tube having a circular cross-section and an inner diameter equal to an outer diameter of the dissection-reinforcement axial portion, the dissection-reinforcement axial portion experiences kinking only when at least an axial portion of the second curved tube has less than a second radius of curvature, which second radius of curvature is at least 30% less than the first radius of curvature.

27. The apparatus according to claim 13,
wherein the lateral fenestration is an inferior first lateral fenestration, which faces in a first radial direction, and
wherein, when the stent-graft is unconstrained in the radially-expanded state, the covering element and the support element are shaped so as to together define a superior second lateral fenestration, which faces in a second radial direction generally opposite the first radial direction.

28. A method for treating a patient comprising:
endovascularly introducing a generally tubular stent-graft, while in a radially-compressed state, and positioning the stent-graft such that (a) a proximal stent-graft end of the stent-graft is positioned in a branch of an aortic arch selected from the group consisting of: a left subclavian artery, and a left common carotid artery, and (b) a distal stent-graft end of the stent-graft is positioned in a descending aorta, wherein the stent-graft includes (a) a generally tubular support element, which includes a plurality of structural stent elements, and (b) a covering element that is attached to and at least partially covers the support element; and
thereafter, transitioning the stent-graft to a radially-expanded state, in which (a) the covering element and the support element are shaped so as to together define a lateral fenestration that is disposed in the aortic arch, with the lateral fenestration facing upstream generally toward an ascending aorta, the lateral fenestration having distal and proximal fenestration ends, (b) a first perimeter of the distal stent-graft end of the stent-graft equals at least 200% of a second perimeter of the proximal stent-graft end, and (c) the stent-graft includes a dissection-reinforcement axial portion, which (i) includes a portion of the structural stent elements, (ii) has (x) a distal dissection-reinforcement end and (y) a proximal dissection-reinforcement end that is disposed along the stent-graft no more than 20 mm proximal to the proximal fenestration end, (iii) extends along the stent-graft for an axial distance, and (iv) has a radial strength that is at least 10% greater than an average radial strength of the entire stent-graft, wherein the axial distance is equal to between 5% and 32% of a greatest perimeter of the stent-graft distally to the distal fenestration end.

29. A method for treating a patient comprising:
endovascularly introducing a generally tubular stent-graft, while in a radially-compressed state, and positioning the stent-graft such that (a) a proximal stent-graft end of the stent-graft is positioned in a branch of an aortic arch selected from the group consisting of: a left subclavian artery, and a left common carotid artery, and (b) a distal stent-graft end of the stent-graft is positioned in a descending aorta, wherein the stent-graft includes (a) a generally tubular support element, which includes a plurality of structural stent elements arranged as a plurality of circumferential stent springs, and (b) a covering element that is attached to and at least partially covers the support element; and
thereafter, transitioning the stent-graft to a radially-expanded state, in which (a) the covering element and the support element are shaped so as to together define a lateral fenestration that is disposed in the aortic arch, with the lateral fenestration facing upstream generally toward an ascending aorta, the lateral fenestration having distal and proximal fenestration ends, (b) a first perimeter of the distal stent-graft end of the stent-graft equals at least 200% of a second perimeter of the proximal stent-graft end, (c) the stent-graft includes a dissection-reinforcement axial portion, which (i) includes a first plurality of the stent springs, (ii) has (x) a distal dissection-reinforcement end and (y) a proximal dissection-reinforcement end that is disposed along the stent-graft no more than 20 mm proximal to the proximal fenestration end, (iii) extends along the stent-graft for a distance, and (iv) is configured to be generally straight when the stent-graft is unconstrained in the radially-constrained state, wherein the distance is equal to between 5% and 32% of a greatest perimeter of the stent-graft distally to the distal fenestration end, (d) the stent-graft includes a distal axial portion, which (i) includes a second plurality of the stent springs, (ii) is disposed along the stent-graft distal and axially adjacent to the distal dissection-reinforcement end, (iii) extends along the stent-graft for a distance, wherein the distance is equal to between 5% and 32% of the greatest perimeter of the stent-graft distally to the distal fenestration end, (e) the stent springs have respective average heights, measured axially along the stent-graft, and (f) an average of the average heights of the first plurality of the stent springs is less than 75% of the average height of a proximal-most one of the second plurality of the stent springs.

* * * * *